United States Patent
Lan et al.

(10) Patent No.: US 11,766,446 B2
(45) Date of Patent: Sep. 26, 2023

(54) TREATMENT OF AGING-ASSOCIATED CONDITIONS BY DNA DEGRADATION

(71) Applicant: The General Hospital Corporation, Boston, MA (US)

(72) Inventors: Yuk Yuen Lan, Quincy, MA (US); Nir Hacohen, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 173 days.

(21) Appl. No.: 17/279,280

(22) PCT Filed: Sep. 25, 2019

(86) PCT No.: PCT/US2019/052947
§ 371 (c)(1),
(2) Date: Mar. 24, 2021

(87) PCT Pub. No.: WO2020/068974
PCT Pub. Date: Apr. 2, 2020

(65) Prior Publication Data
US 2022/0031725 A1    Feb. 3, 2022

Related U.S. Application Data

(60) Provisional application No. 62/736,138, filed on Sep. 25, 2018.

(51) Int. Cl.
*A01N 43/04*      (2006.01)
*A61K 31/70*      (2006.01)
*A61K 31/7068*    (2006.01)

(52) U.S. Cl.
CPC ................................ *A61K 31/7068* (2013.01)

(58) Field of Classification Search
None
See application file for complete search history.

(56) References Cited

PUBLICATIONS

Fischer, Heinz, et al. "Holocrine secretion of sebum is a unique DNase2-dependent mode of programmed cell death." Journal of Investigative Dermatology 137.3 (2017): 587-594.*
Tetz, Victor, and George Tetz. "Effect of deoxyribonuclease I treatment for dementia in end-stage Alzheimer's disease: A case report." Journal of medical case reports 10.1 (2016): 1-3.*
Xia, Shijin, et al. "An update on inflamm-aging: mechanisms, prevention, and treatment." Journal of immunology research 2016 (2016).*
International Search Report and Written Opinion for Application No. PCT/US2019/052947, dated Nov. 27, 2019.
International Preliminary Report on Patentability for Application No. PCT/US2019/052947, dated Apr. 8, 2021.
Ahn et al., STING manifests self DNA-dependent inflammatory disease. Proc Natl Acad Sci U S A. Nov. 20, 2012;109(47):19386-91. doi: 10.1073/pnas.1215006109. Epub Nov. 6, 2012.
Bakhoum et al., Chromosomal instability drives metastasis through a cytosolic DNA response. Nature. Jan. 25, 2018;553(7689):467-472. doi: 10.1038/nature25432. Epub Jan. 17, 2018.
Lan et al., Dnase2a deficiency uncovers lysosomal clearance of damaged nuclear DNA via autophagy. Cell Rep. Oct. 9, 2014;9(1):180-192. doi: 10.1016/j.celrep.2014.08.074. Epub Oct. 2, 2014.
Lan et al., Extranuclear DNA accumulates in aged cells and contributes to senescence and inflammation. Aging Cell. Apr. 2019;18(2):e12901. doi: 10.1111/acel.12901. Epub Jan. 31, 2019.
Rodero et al., Type I interferon-mediated autoinflammation due to DNase II deficiency. Nat Commun. Dec. 19, 2017;8(1):2176. doi: 10.1038/s41467-017-01932-3.
Takahashi et al., Downregulation of cytoplasmic DNases is implicated in cytoplasmic DNA accumulation and SASP in senescent cells. Nat Commun. Mar. 28, 2018;9(1):1249. doi: 10.1038/s41467-018-03555-8.
Takahashi et al., Exosomes maintain cellular homeostasis by excreting harmful DNA from cells. Nat Commun. May 16, 2017;8:15287. doi: 10.1038/ncomms15287.
GENBANK Submission; NIH/NCBI, Accession No. NM_001375.2. Fujihara et al., Sep. 15, 2018. 5 pages.
GENBANK Submission; NIH/NCBI, Accession No. NP_001366.1. Fujihara et al., Sep. 15, 2018. 3 pages.
Almine et al., IFI16 and cGAS cooperate in the activation of STING during DNA sensing in human keratinocytes. Nature Commun. Feb. 13, 2017;8:14392. doi: 10.1038/ncomms14392.
Bartkova et al., Oncogene-induced senescence is part of the tumorigenesis barrier imposed by DNA damage checkpoints. Nature. Nov. 30, 2006;444(7119):633-7. doi: 10.1038/nature05268.
Baruch et al., Aging. Aging-induced type I interferon response at the choroid plexus negatively affects brain function. Science. Oct. 3, 2014;346(6205):89-93. doi: 10.1126/science.1252945. Epub Aug. 21, 2014.
Coppe et al., A human-like senescence-associated secretory phenotype is conserved in mouse cells dependent on physiological oxygen. PLoS One. Feb. 12, 2010;5(2):e9188. doi: 10.1371/journal.pone.0009188.
De Vos et al., Repetitive disruptions of the nuclear envelope invoke temporary loss of cellular compartmentalization in laminopathies. Hum Mol Genet. Nov. 1, 2011;20(21):4175-86. doi: 10.1093/hmg/ddr344. Epub Aug. 10, 2011.
Di Leonardo et al., DNA damage triggers a prolonged p53-dependent G1 arrest and longterm induction of Cip1 in normal human fibroblasts. Genes Dev. Nov. 1, 1994;8(21):2540-51. doi: 10.1101/gad.8.21.2540.
Dou et al., Cytoplasmic chromatin triggers inflammation in senescence and cancer. Nature. Oct. 19, 2017;550(7676):402-6. doi: 10.1038/nature24050. Epub Oct. 4, 2017.

(Continued)

*Primary Examiner* — Patrick T Lewis
(74) *Attorney, Agent, or Firm* — Wolf, Greenfield & Sacks, P.C.

(57) ABSTRACT

Provided herein, in some embodiments, are methods for treating age-associated conditions, including systemic inflammation and disease, via enhanced DNA degradation.

14 Claims, 36 Drawing Sheets
Specification includes a Sequence Listing.

(56) References Cited

PUBLICATIONS

Duan et al., Differential roles for the interferon-inducible IFI16 and AIM2 innate immune sensors for cytosolic DNA in cellular senescence of human fibroblasts. Mol Cancer Res. May 2011;9(5):589-602. doi: 10.1158/1541-7786.MCR-10-0565. Epub Apr. 6, 2011.

Fagiolo et al., Increased cytokine production in mononuclear cells of healthy elderly people. Eur J Immunol. Sep. 1993;23(9):2375-8. doi: 10.1002/eji.1830230950.

Gluck et al., Innate immune sensing of cytosolic chromatin fragments through cGAS promotes senescence. Nat Cell Biol. Sep. 2017;19(9):1061-70. doi: 10.1038/ncb3586. Epub Jul. 31, 2017.

Goldman et al., Accumulation of mutant lamin A causes progressive changes in nuclear architecture in Hutchinson-Gilford progeria syndrome. Proc Natl Acad Sci U S A. Jun. 15, 2004;101(24):8963-8. doi: 10.1073/pnas.0402943101. Epub Jun. 7, 2004.

Gorbea et al., Depletion of the 26S proteasome adaptor Ecm29 increases Toll-like receptor 3 signaling. Sci Signal. Oct. 1, 2013;6(295):ra86. doi: 10.1126/scisignal.2004301.

Hartlova et al., DNA damage primes the type I interferon system via the cytosolic DNA sensor STING to promote anti-microbial innate immunity. Immunity. Feb. 17, 2015;42(2):332-43. doi: 10.1016/j.immuni.2015.01.012.

Hatch et al., Catastrophic nuclear envelope collapse in cancer cell micronuclei. Cell. Jul. 3, 2013;154(1):47-60. doi: 10.1016/j.cell.2013.06.007.

Herzner et al., Sequence-specific activation of the DNA sensor cGAS by Y-form DNA structures as found in primary HIV-1 cDNA. Nat Immunol. Oct. 2015;16(10):1025-33. doi: 10.1038/ni.3267. Epub Sep. 7, 2015.

High et al., Gene Therapy. N Engl J Med. Aug. 1, 2019;381(5):455-64. doi: 10.1056/NEJMra1706910.

Ingusci et al., Gene Therapy Tools for Brain Diseases. Front Pharmacol. Jul. 1, 2019;10:724. doi: 10.3389/fphar.2019.00724. eCollection 2019.

Ivanov et al., Lysosome-mediated processing of chromatin in senescence. J Cell Biol. Jul. 8, 2013;202(1):129-43. doi: 10.1083/jcb.201212110. Epub Jul. 1, 2013.

Kallunki et al., How to Choose the Right Inducible Gene Expression System for Mammalian Studies? Cells. Jul. 30, 2019;8(8):796. doi: 10.3390/cells8080796.

Katlinskaya et al., Suppression of Type I Interferon Signaling Overcomes Oncogene-Induced Senescence and Mediates Melanoma Development and Progression. Cell Rep. Apr. 5, 2016;15(1):171-80. doi: 10.1016/j.celrep.2016.03.006. Epub Mar. 24, 2016.

Kerur et al., IFI16 acts as a nuclear pathogen sensor to induce the inflammasome in response to Kaposi Sarcoma-associated herpesvirus infection. Cell Host Microbe. May 19, 2011;9(5):363-75. doi: 10.1016/j.chom.2011.04.008.

Langmead et al., Fast gapped-read alignment with Bowtie 2. Nat Methods. Mar. 4, 2012;9(4):357-9. doi: 10.1038/nmeth.1923.

Le et al., Ionizing radiation-induced long-term expression of senescence markers in mice is independent of p53 and immune status. Aging Cell. Jun. 2010;9(3):398-409. doi: 10.1111/j.1474-9726.2010.00567.x. Epub Mar. 13, 2010.

Leng et al., EBSeq: an empirical Bayes hierarchical model for inference in RNA-seq experiments. Bioinformatics. Apr. 15, 2013;29(8):1035-43. doi: 10.1093/bioinformatics/btt087. Epub Feb. 21, 2013.

Li et al., RSEM: accurate transcript quantification from RNA-Seq data with or without a reference genome. BMC Bioinformatics. Aug. 4, 2011;12:323. doi: 10.1186/1471-2105-12-323.

Li et al., The cGAS-cGAMP-STING pathway connects DNA damage to inflammation, senescence, and cancer. J Exp Med. May 7, 2018;215(5):1287-99. doi: 10.1084/jem.20180139. Epub Apr. 5, 2018.

Liang et al., Crosstalk between the cGAS DNA sensor and Beclin-1 autophagy protein shapes innate antimicrobial immune responses. Cell Host & Microbe. Feb. 12, 2014;15(2):228-38. doi: 10.1016/i.chom.2014.01.009.

Liberzon et al., The Molecular Signatures Database Hallmark Gene Set Collection. Cell Syst. Dec. 23, 2015;1(6):417-425. doi: 10.1016/j.cels.2015.12.004.

Lu et al., Gene regulation and DNA damage in the ageing human brain. Nature. Jun. 24, 2004;429(6994):883-91. doi: 10.1038/nature02661. Epub Jun. 9, 2004.

Moss, Gene therapy review. Radiol Technol. Nov.-Dec. 2014;86(2):155-80; quiz 181-4.

Nougayrede et al., *Escherichia coli* induces DNA double-strand breaks in eukaryotic cells. Science. Aug. 11, 2006;313(5788):848-51. doi: 10.1126/science.1127059.

Parrinello et al., Oxygen sensitivity severely limits the replicative lifespan of murine fibroblasts. Nat Cell Biol. Aug. 2003;5(8):741-7. doi: 10.1038/ncb1024.

Picelli et al., Full-length RNA-seq from single cells using Smart-seq2. Nat Protoc. Jan. 2014;9(1):171-81. doi: 10.1038/nprot.2014.006. Epub Jan. 2, 2014.

Raab et al., ESCRT III repairs nuclear envelope ruptures during cell migration to limit DNA damage and cell death. Science. Apr. 15, 2016;352(6283):359-62. doi: 10.1126/science.aad7611. Epub Mar. 24, 2016.

Reich et al. GenePattern 2.0. Nat Genet. May 2006;38(5):500-1. doi: 10.1038/ng0506-500.

Roubenoff et al., Cytokines, insulin-like growth factor 1, sarcopenia, and mortality in very old community-dwelling men and women: The Framingham Heart Study. Am J Med. Oct. 15, 2003;115(6):429-35. doi: 10.1016/j.amjmed.2003.05.001.

Rube et al., Accumulation of DNA damage in hematopoietic stem and progenitor cells during human aging. PLoS One. Mar. 7, 2011;6(3):e17487. doi: 10.1371/journal.pone.0017487.

Rusinova et al., Interferome v2.0: An updated database of annotated interferon-regulated genes. Nucleic Acids Res. Jan. 2013;41(Database issue):D1040-6. doi: 10.1093/nar/gks1215. Epub Nov. 29, 2012.

Sedelnikova et al., Senescing human cells and ageing mice accumulate DNA lesions with unrepairable double-strand breaks. Nat Cell Biol. Feb. 2004;6(2):168-70. doi: 10.1038/ncb1095. Epub Feb. 2, 2004.

Singh et al., Inflammatory markers in population studies of aging. Ageing Res Rev. Jul. 2011;10(3):319-29. doi: 10.1016/j.arr.2010.11.002. Epub Dec. 8, 2010.

Speese et al., Nuclear envelope budding enables large ribonucleoprotein particle export during synaptic Wnt signaling. Cell. May 11, 2012;149(4):832-46. doi: 10.1016/j.cell.2012.03.032.

Subramanian et al., Gene set enrichment analysis: A knowledge-based approach for interpreting genome wide expression profiles. Proc Natl Acad Sci U S A. Oct. 25, 2005;102(43):15545-50. doi: 10.1073/pnas.0506580102. Epub Sep. 30, 2005.

Vargas et al., Transient nuclear envelope rupturing during interphase in human cancer cells. Nucleus. Jan.-Feb. 2012;3(1):88-100. doi: 10.4161/nucl.18954.

Wang et al., DNA damage response and cellular senescence in tissues of aging mice. Aging Cell. Jun. 2009;8(3):311-23. doi: 10.1111/j.1474-9726.2009.00481.x. Epub Apr. 9, 2009.

Wang et al., NanoStringDiff: a novel statistical method for differential expression analysis based on NanoString nCounter data. Nucleic Acids Res. Nov. 16, 2016;44(20):e151. doi: 10.1093/nar/gkw677. Epub Jul. 28, 2016.

Wang et al., WEB-based GEne SeT AnaLysis Toolkit (WebGestalt): update 2013. Nucleic Acids Res. Jul. 2013;41(Web Server issue):W77-83. doi: 10.1093/nar/gkt439. Epub May 23, 2013.

Yang et al., cGAS is essential for cellular senescence. Proc Natl Acad Sci U S A. Jun. 6, 2017;114(23):E4612-E4620. doi: 10.1073/pnas.1705499114. Epub May 22, 2017.

Yu et al., DNA-damage-induced type I interferon promotes senescence and inhibits stem cell function. Cell Rep. May 5, 2015;11(5):785-97. doi: 10.1016/j.celrep.2015.03.069. Epub Apr. 23, 2015.

\* cited by examiner

| Enriched in AT | FDR q-val |
|---|---|
| ANDROGEN_RESPONSE | 0.0551 |
| COAGULATION | 0.0471 |
| PANCREAS_BETA_CELLS | 0.0591 |
| INTERFERON_ALPHA_RESPONSE | 0.0490 |
| TNFA_SIGNALING_VIA_NFKB | 0.0966 |
| XENOBIOTIC_METABOLISM | 0.0979 |
| IL6_JAK_STAT3_SIGNALING | 0.0841 |
| IL2_STAT5_SIGNALING | 0.0807 |
| INFLAMMATORY_RESPONSE | 0.0926 |
| KRAS_SIGNALING_UP | 0.1075 |
| ESTROGEN_RESPONSE_LATE | 0.1297 |

| Enriched in PS | FDR q-val |
|---|---|
| IL6_JAK_STAT3_SIGNALING | 0.0746 |
| COAGULATION | 0.0517 |
| PANCREAS_BETA_CELLS | 0.0687 |
| KRAS_SIGNALING_UP | 0.1136 |

FIG. 3B

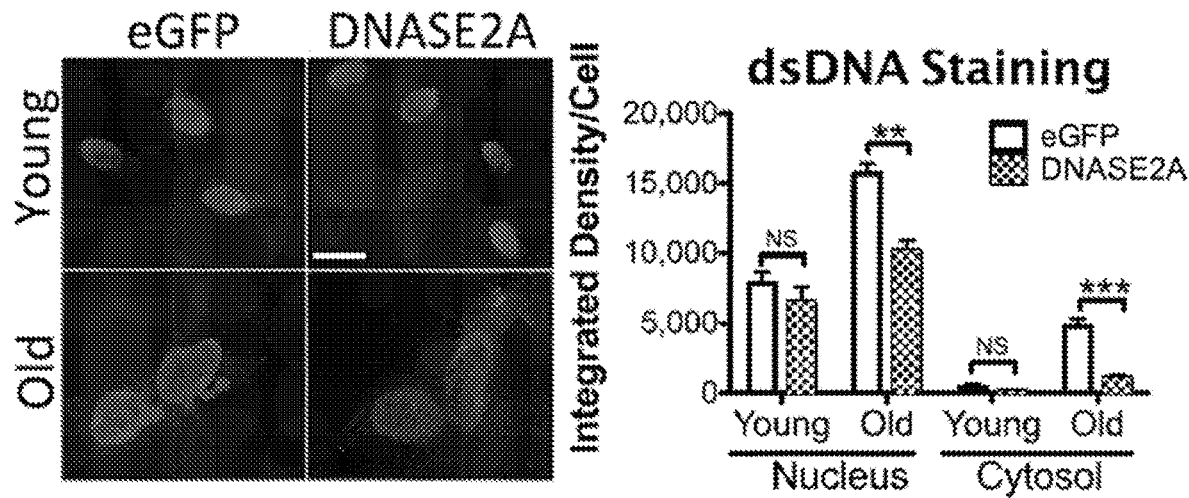
FIG. 4C
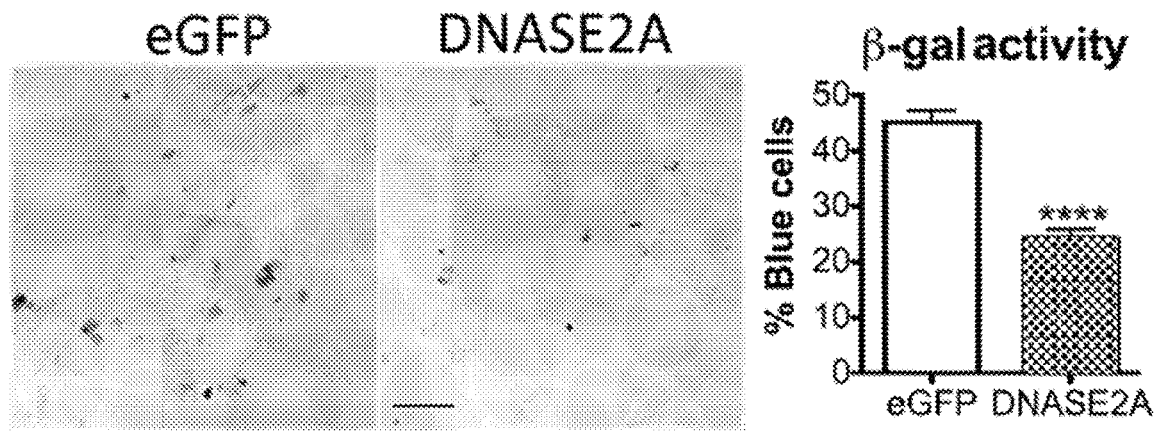
FIG. 4D
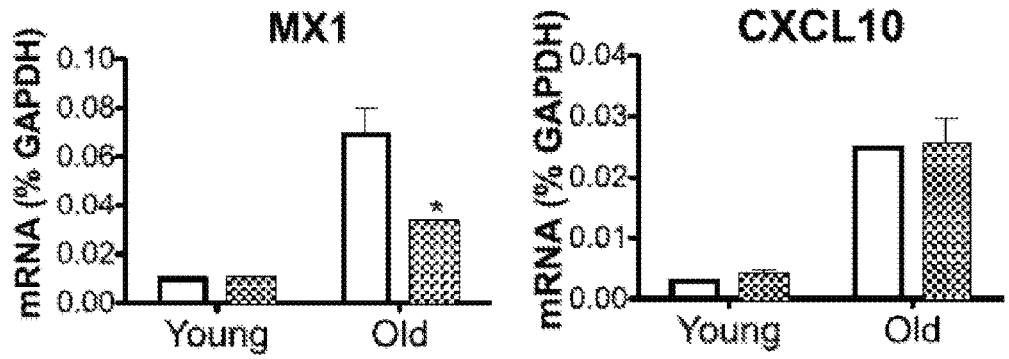

| UP-REGULATED GENES | MEAN RATIO | GENE NAME |
|---|---|---|
| *Innate immunity, inflammation* | | |
| CASP1 | 1.92 | Caspase 1 |
| CCL1 | 2.73 | C-C motif chemokine ligand 1 |
| CREM | 1.45 | CAMP Responsive Element Modulator |
| DCTN5 | 1.42 | Dynactin Subunit 5 |
| DDX58 | 1.85 | DExD/H-Box Helicase 58 |
| FAS | 2.29 | Fas Cell Surface Death Receptor |
| GBP1 | 1.82 | guanylate binding protein 1 |
| GBP3 | 1.50 | Guanylate Binding Protein 3 |
| IFI27 | 3.90 | Interferon Alpha Inducible Protein 27 |
| IFIT2 | 3.03 | Interferon Induced Protein With Tetratricopeptide Repeats 2 |
| IFIT5 | 1.69 | Interferon Induced Protein With Tetratricopeptide Repeats 5 |
| IFITM3 | 1.57 | Interferon Induced Transmembrane Protein 3 |
| IFNAR2 | 1.56 | Interferon Alpha And Beta Receptor Subunit 2 |
| IL33 | 2.91 | Interleukin 33 |
| IL4R | 1.74 | Interleukin 4 Receptor |
| IL6 | 2.96 | Interleukin 6 |
| LILRA3 | 3.33 | leukocyte immunoglobulin like receptor A3 |
| MAP3K8 | 4.14 | Mitogen-Activated Protein Kinase Kinase Kinase 8 |
| NFKB2 | 1.69 | Nuclear Factor Kappa B Subunit 2 |
| NLRP3 | 3.67 | NLR Family Pyrin Domain Containing 3 |
| OLR1 | 5.40 | oxidized low density lipoprotein receptor 1 |
| PTPN1 | 1.41 | Protein Tyrosine Phosphatase, Non-Receptor Type 1 |
| STAT1 | 1.67 | Signal Transducer And Activator Of Transcription 1 |
| STAT2 | 1.74 | Signal Transducer And Activator Of Transcription 2 |
| STAT3 | 1.45 | Signal Transducer And Activator Of Transcription 3 |
| STAT6 | 1.67 | Signal Transducer And Activator Of Transcription 6 |
| TIRAP | 2.75 | TIR domain containing adaptor protein |
| TLR8 | 2.43 | Toll Like Receptor 8 |
| TNFRSF1A | 1.33 | TNF Receptor Superfamily Member 1A |
| *Growth and differentiation* | | |
| C15orf48 | 2.89 | Chromosome 15 open reading frame 48 |
| CD2AP | 1.63 | CD2 Associated Protein |
| CDC37 | 1.54 | Cell Division Cycle 37 |
| DUSP6 | 2.56 | Dual specificity phosphatase 6 |
| FGD4 | 2.70 | FYVE, RhoGEF and PH domain containing 4 |
| GADD45A | 1.40 | Growth Arrest And DNA Damage Inducible Alpha |
| GCOM1 | 2.89 | GRINL1A complex locus 1 |
| GSTT1 | 1.91 | Glutathione S-transferase theta 1 |
| HIST2H2BE | 2.62 | Histone Cluster 2 H2B Family Member E |
| HK2 | 2.24 | Hexokinase 2 |
| MAPK3 | 1.40 | Mitogen-Activated Protein Kinase 3 |
| SLFN5 | 1.62 | Schlafen Family Member 5 |
| *Other functions* | | |
| ATP13A3 | 1.46 | ATPase 13A3 |
| C12orf23 | 1.68 | Transmembrane protein 263 |
| C17orf48 | 1.96 | ADP-ribose/CDP-alcohol diphosphatase, manganese dependent |
| C6orf192 | 2.14 | Solute carrier family 18 member B1 |
| CASS4 | 2.28 | Cas scaffolding protein family member 4 |
| CYBRD1 | 1.37 | Cytochrome B Reductase 1 |
| DSP | 2.41 | Desmoplakin |
| EDN1 | 2.44 | Endothelin 1 |
| FBN2 | 1.82 | Fibrillin 2 |
| FRMD3 | 7.03 | FERM domain containing 3 |
| GPR68 | 1.94 | G protein-coupled receptor 68 |
| GSTM3 | 1.82 | Glutathione S-transferase mu 3 |
| MCOLN2 | 2.56 | mucolipin 2 |
| PLAT | 3.62 | Plasminogen activator, tissue type |
| PLAU | 1.58 | Plasminogen Activator, Urokinase |
| RAB7L1 | 1.84 | RAB7, member RAS oncogene family-like 1 |
| RBM43 | 2.26 | RNA binding motif protein 43 |
| RNF149 | 1.43 | Ring Finger Protein 149 |

FIG. 7A

| DOWN-REGULATED GENES | MEAN RATIO | GENE NAME |
|---|---|---|
| *Innate Immunity, Inflammation* | | |
| HMGB1 | 0.59 | High mobility group box 1 |
| HMGB2 | 0.47 | High mobility group box 2 |
| HMGB3 | 0.52 | High mobility group box 3 |
| *Growth and differentiation* | | |
| AXL | 0.59 | AXL receptor tyrosine kinase |
| BRIP1 | 0.64 | BRCA1 interacting protein C-terminal helicase 1 |
| CD24 | 0.43 | CD24 molecule |
| CKB | 0.57 | Creatine kinase B |
| HIRA | 0.62 | Histone cell cycle regulator |
| PTGER2 | 0.64 | Prostaglandin E receptor 2 (subtype EP2) |
| SEMA3D | 0.49 | Semaphorin 3D |
| VCAN | 0.52 | Versican |
| *Other functions* | | |
| ATP1B1 | 0.75 | ATPase Na+/K+ transporting subunit beta 1 |
| CCDC109B | 0.43 | Mitochondrial calcium uniporter dominant negative beta subunit |
| GEM | 0.58 | GTP binding protein overexpressed in skeletal muscle |
| PTMA | 0.59 | Prothymosin, alpha |
| SLC1A3 | 0.37 | Solute carrier family 1 member 3 |

FIG. 7A cont.

| UP (35) | DOWN (31) |
|---|---|
| ABTB2 | WARS |
| IFI30 | PSMA4 |
| GPER1 | RPL17 |
| HIST1H2BD | PSMA2 |
| HIST2H2AA4 | PSMA6 |
| GMPR | MDK |
| ATF3 | GEM |
| HIST2H2BE | IRF2 |
| DPP4 | CCDC109B |
| HIST1H4H | CEP57 |
| HIST2H2AC | FAM129A |
| ANKHD1-EIF4EBP3 | AGPAT5 |
| TRIM22 | TIMM21 |
| ZMAT3 | MCM6 |
| SCD5 | MASTL |
| IFIT2 | CDC45 |
| SLFN12 | C1orf112 |
| FAM46A | EXO1 |
| TRIM38 | KNTC1 |
| DUSP6 | C21orf58 |
| CREBL2 | RFC3 |
| TRADD | RFC4 |
| GAN | ASF1B |
| PIK3CB | BRI3BP |
| BMPR2 | POLE2 |
| DCAF6 | AKAP7 |
| MACF1 | MCM10 |
| SAMHD1 | HIST1H4C |
| GLS | PRIM1 |
| B3GNT2 | ATAD5 |
| PTPRA | HIST2H2AC |
| SYTL3 | |
| SYTL3 | |
| PML | |
| RBMS2 | |

FIG. 7B

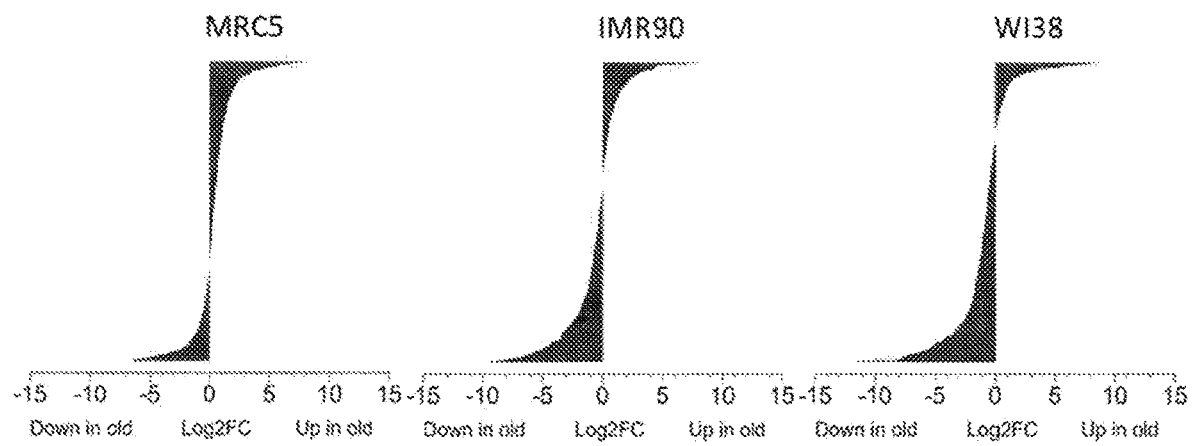

FIG. 7E

| Enriched in Old | FDR q-val |
|---|---|
| HALLMARK_TNFA_SIGNALING_VIA_NFKB | 0.00000 |
| HALLMARK_P53_PATHWAY | 0.00000 |
| HALLMARK_INFLAMMATORY_RESPONSE | 0.00000 |
| HALLMARK_KRAS_SIGNALING_UP | 0.01031 |
| HALLMARK_HEME_METABOLISM | 0.01080 |
| HALLMARK_INTERFERON_ALPHA_RESPONSE | 0.01064 |
| HALLMARK_INTERFERON_GAMMA_RESPONSE | 0.01337 |
| HALLMARK_APOPTOSIS | 0.01204 |
| HALLMARK_MYOGENESIS | 0.01797 |
| HALLMARK_KRAS_SIGNALING_DN | 0.02107 |
| HALLMARK_IL2_STAT5_SIGNALING | 0.04706 |
| HALLMARK_HYPOXIA | 0.04957 |
| HALLMARK_ESTROGEN_RESPONSE_EARLY | 0.07067 |
| HALLMARK_UV_RESPONSE_UP | 0.07519 |
| HALLMARK_NOTCH_SIGNALING | 0.08591 |
| HALLMARK_IL6_JAK_STAT3_SIGNALING | 0.11277 |
| HALLMARK_COAGULATION | 0.17488 |
| HALLMARK_PEROXISOME | 0.16768 |
| HALLMARK_XENOBIOTIC_METABOLISM | 0.22617 |
| HALLMARK_ADIPOGENESIS | 0.24059 |
| HALLMARK_EPITHELIAL_MESENCHYMAL_TRANSITION | 0.33919 |
| HALLMARK_ANGIOGENESIS | 0.34802 |
| HALLMARK_TGF_BETA_SIGNALING | 0.39715 |
| HALLMARK_UV_RESPONSE_DN | 0.91599 |
| HALLMARK_PROTEIN_SECRETION | 0.91273 |

FIG. 7F

| STING Genes |
|---|
| IL1A |
| IGHE |
| ZDHHC1 |
| PLA2G6 |
| F3 |
| IKBKB |
| DDX58 |
| HRH4 |
| NLRC3 |
| TSLP |
| SAMHD1 |
| DTX4 |
| TRIM32 |
| BAX |
| IL4R |
| MAVS |
| MT-ND1 |
| SCP2 |
| TRAF3 |
| TRIM56 |
| STAT6 |
| PPM1A |
| HRH1 |
| UBE2D1 |
| NEXN |
| MRI1 |
| TREX1 |
| TMEM173 |
| TRIM21 |
| TBK1 |
| TFG |
| IRF3 |
| WASL |
| DDX41 |
| IFI16 |
| TRAF6 |
| KITLG |
| TICAM1 |
| UBE2D3 |
| ISG20 |
| ULK1 |
| PRKDC |
| TPT1 |
| MB21D1 |
| XRCC6 |
| XRCC5 |
| SSR2 |
| TRAF2 |
| NFKBIA |
| CCL5 |
| SLC6A4 |
| FCER2 |
| POMC |
| IL10 |

FIG. 7G

SEQUENCE LISTING

```
<160> NUMBER OF SEQ ID NOS: 62

<210> SEQ ID NO 1
<211> LENGTH: 1938
<212> TYPE: DNA
<213> ORGANISM: Homo sapiens

<400> SEQUENCE: 1
agtcctggcc tctgatgtaa cccagcgccc cgcagtcccg acacagattc ctggatctca      60
gccccatagc agctatgatc ccgctgctgc tggcagcgct gctgtgcgtc cccgccgggg     120
ccctgacctg ctacggggac tccgggcagc ctgtagactg gttcgtggtc tacaagctgc     180
cagctcttag agggtccggg gaggcggcgc agagagggct gcagtacaag tatctggacg     240
agagctccgg aggctggcgg gacggcaggg cactcatcaa cagcccggag ggggccgtgg     300
gccgaagcct gcagccgctg taccggagca acaccagcca gctcgccttc ctgctctaca     360
```

```
atgaccaacc gcctcaaccc agcaaggctc aggactcttc catgcgtggg cacacgaagg    420
gtgtcctgct ccttgaccac gatgggggct tctggctggt ccacagtgta cctaacttcc    480
ctccaccggc ctcctctgct gcatacagct ggcctcatag cgcctgtacc tacgggcaga    540
ccctgctctg tgtgtctttt cccttcgctc agttctcgaa gatgggcaag cagctgacct    600
acacctaccc ctgggtctat aactaccagc tggaagggat ctttgcccag gaattccccg    660
acttggagaa tgtggtcaag gccaccacg ttagccaaga accctggaac agcagcatca    720
cactcacatc ccaggccggg gctgttttcc agagctttgc caagttcagc aaatttggag    780
atgacctgta ctccggctgg ttggcagcag cccttggtac caacctgcag gtccagttct    840
ggcacaaaac tgtaggcatc ctgccctcta actgctcgga tatctggcag gttctgaatg    900
tgaaccagat agctttccct ggaccagccg cccaagctt caacagcaca gaggaccact    960
ccaaatggtg cgtgtcccca aagggccct ggacctgcgt gggtgacatg aatcggaacc   1020
agggagagga gcaacgggt gggggcacac tgtgtgccca gctgccagcc ctctggaaag   1080
ccttccagcc gctggtgaag aactaccagc cctgtaatgg catggccagg aagcccagca   1140
gagcttataa gatctaaccc ttatggccag gtgcagtggc tcacgtatgt aatcccagca   1200
ctttgggaag ccaaggaggg aggatcactt gaactcagga attcgagacc agcctgggct   1260
acatagtgag accacatctc tactagaact taaaaaagt tagccaggca cggtgataaa   1320
tgcctgtagt cccagccact gaagccagag gatcgattga accagggaga tcatggtcac   1380
agtgaactat gattacgcca acctgggtca catagcaaga ctctgtttca aaaaaaaagg   1440 ggggggcgggg gacgggtggg tgcagtggct cacatctgta accccagcac tttgggaggc   1500
tgagatgggc agatcacttg aggtcaggag ttcgagacca gcctggccaa catggtgaaa   1560
ccccatatcc attaaaaata tttaaaaatt agccagacat ggtggcacgc gtctgtggtc   1620
ctagctcctc gggaggctga ggcaggagaa tcgcttgaac tcgggaggca gaggttgtca   1680
tgagctgagc taacaccacg gcacttcagc ctgggtgaca gaatgagact ctgtgtcaaa   1740
aaaataaaaa ataaaaaatc taagggctca ggaaccagtt tggacttgat tttgaatccc   1800
agttcatccc cttcctagct gtatgacctt gattgtgtgc cttaaccgct ctgtgacaca   1860
gtctacctgt ctgcaaaatg ggaaacataa tacctgccat caggattgtt gaggagtaaa   1920
taaatggaaa ttggtgga                                                 1938
```

<210> SEQ ID NO 2
<211> LENGTH: 360
<212> TYPE: PRT
<213> ORGANISM: Homo sapiens

<400> SEQUENCE: 2

Met Ile Pro Leu Leu Leu Ala Ala Leu Leu Cys Val Pro Ala Gly Ala
1               5                  10                  15

Leu Thr Cys Tyr Gly Asp Ser Gly Gln Pro Val Asp Trp Phe Val Val
            20                  25                  30

Tyr Lys Leu Pro Ala Leu Arg Gly Ser Gly Glu Ala Ala Gln Arg Gly
        35                  40                  45

Leu Gln Tyr Lys Tyr Leu Asp Glu Ser Ser Gly Gly Trp Arg Asp Gly
    50                  55                  60

Arg Ala Leu Ile Asn Ser Pro Glu Gly Ala Val Gly Arg Ser Leu Gln
65                  70                  75                  80

Pro Leu Tyr Arg Ser Asn Thr Ser Gln Leu Ala Phe Leu Leu Tyr Asn

```
                   85                  90                  95
Asp Gln Pro Pro Gln Pro Ser Lys Ala Gln Asp Ser Ser Met Arg Gly
                100                 105                 110
His Thr Lys Gly Val Leu Leu Asp His Asp Gly Gly Phe Trp Leu
            115                 120                 125
Val His Ser Val Pro Asn Phe Pro Pro Ala Ser Ser Ala Ala Tyr
        130                 135                 140
Ser Trp Pro His Ser Ala Cys Thr Tyr Gly Gln Thr Leu Leu Cys Val
145                 150                 155                 160
Ser Phe Pro Phe Ala Gln Phe Ser Lys Met Gly Lys Gln Leu Thr Tyr
                165                 170                 175
Thr Tyr Pro Trp Val Tyr Asn Tyr Gln Leu Glu Gly Ile Phe Ala Gln
                180                 185                 190
Glu Phe Pro Asp Leu Glu Asn Val Val Lys Gly His His Val Ser Gln
                195                 200                 205
Glu Pro Trp Asn Ser Ser Ile Thr Leu Thr Ser Gln Ala Gly Ala Val
                210                 215                 220
Phe Gln Ser Phe Ala Lys Phe Ser Lys Phe Gly Asp Asp Leu Tyr Ser
225                 230                 235                 240
Gly Trp Leu Ala Ala Leu Gly Thr Asn Leu Gln Val Gln Phe Trp
                245                 250                 255
His Lys Thr Val Gly Ile Leu Pro Ser Asn Cys Ser Asp Ile Trp Gln
                260                 265                 270
Val Leu Asn Val Asn Gln Ile Ala Phe Pro Gly Pro Ala Gly Pro Ser
                275                 280                 285
Phe Asn Ser Thr Glu Asp His Ser Lys Trp Cys Val Ser Pro Lys Gly
                290                 295                 300
Pro Trp Thr Cys Val Gly Asp Met Asn Arg Asn Gln Gly Glu Glu Gln
305                 310                 315                 320
Arg Gly Gly Gly Thr Leu Cys Ala Gln Leu Pro Ala Leu Trp Lys Ala
                325                 330                 335
Phe Gln Pro Leu Val Lys Asn Tyr Gln Pro Cys Asn Gly Met Ala Arg
                340                 345                 350
Lys Pro Ser Arg Ala Tyr Lys Ile
                355                 360

<210> SEQ ID NO 3
<211> LENGTH: 22
<212> TYPE: DNA
<213> ORGANISM: Homo sapiens

<400> SEQUENCE: 3
aaagatgtgc ttcgagatgt gt                                               22

<210> SEQ ID NO 4
<211> LENGTH: 23
<212> TYPE: DNA
<213> ORGANISM: Homo sapiens

<400> SEQUENCE: 4
cactttgtca gttaccaacg tca                                              23

<210> SEQ ID NO 5
<211> LENGTH: 19
<212> TYPE: DNA
<213> ORGANISM: Homo sapiens
```

<400> SEQUENCE: 5
ccatgcaggt gagcttcgt                                                    19

<210> SEQ ID NO 6
<211> LENGTH: 21
<212> TYPE: DNA
<213> ORGANISM: Homo sapiens

<400> SEQUENCE: 6
gaatctgcga gagacaccat c                                                 21

<210> SEQ ID NO 7
<211> LENGTH: 20
<212> TYPE: DNA
<213> ORGANISM: Homo sapiens

<400> SEQUENCE: 7
tgcccagact acgacttgtg                                                   20

<210> SEQ ID NO 8
<211> LENGTH: 21
<212> TYPE: DNA
<213> ORGANISM: Homo sapiens

<400> SEQUENCE: 8
agtgtccgtg tttcaccttc c                                                 21

<210> SEQ ID NO 9
<211> LENGTH: 23
<212> TYPE: DNA
<213> ORGANISM: Homo sapiens

<400> SEQUENCE: 9
tggattcgac ttagacttga cct                                               23

<210> SEQ ID NO 10
<211> LENGTH: 22
<212> TYPE: DNA
<213> ORGANISM: Homo sapiens

<400> SEQUENCE: 10
tggcggtgtc ataatgtctt tc                                                22

<210> SEQ ID NO 11
<211> LENGTH: 23
<212> TYPE: DNA
<213> ORGANISM: Homo sapiens

<400> SEQUENCE: 11
taaccctggc tttggaatca aaa                                               23

<210> SEQ ID NO 12
<211> LENGTH: 23
<212> TYPE: DNA
<213> ORGANISM: Homo sapiens

<400> SEQUENCE: 12
tgggtacaag gtaaaatggc ttt                                               23

<210> SEQ ID NO 13
<211> LENGTH: 22
<212> TYPE: DNA
<213> ORGANISM: Homo sapiens

<400> SEQUENCE: 13
ggtcaccgct ccaaatatgt ag                                    22

<210> SEQ ID NO 14
<211> LENGTH: 21
<212> TYPE: DNA
<213> ORGANISM: Homo sapiens

<400> SEQUENCE: 14
cagtagtcca agttcgtgcg a                                     21

<210> SEQ ID NO 15
<211> LENGTH: 20
<212> TYPE: DNA
<213> ORGANISM: Homo sapiens

<400> SEQUENCE: 15
agcggcagag ttaggtgaaa                                       20

<210> SEQ ID NO 16
<211> LENGTH: 20
<212> TYPE: DNA
<213> ORGANISM: Homo sapiens

<400> SEQUENCE: 16
tgagtgcctt cttgatgtgc                                       20

<210> SEQ ID NO 17
<211> LENGTH: 21
<212> TYPE: DNA
<213> ORGANISM: Homo sapiens

<400> SEQUENCE: 17
gtttccgaag tggacatcgc a                                     21

<210> SEQ ID NO 18
<211> LENGTH: 20
<212> TYPE: DNA
<213> ORGANISM: Homo sapiens

<400> SEQUENCE: 18
ctgcacaggt tgttctcagc                                       20

<210> SEQ ID NO 19
<211> LENGTH: 22
<212> TYPE: DNA
<213> ORGANISM: Homo sapiens

<400> SEQUENCE: 19
ttgatgacga tgaaatgcct ga                                    22

<210> SEQ ID NO 20
<211> LENGTH: 20
<212> TYPE: DNA
<213> ORGANISM: Homo sapiens

<400> SEQUENCE: 20
caggtcacca gactcctcac                                       20

<210> SEQ ID NO 21
<211> LENGTH: 22
<212> TYPE: DNA

-continued

<213> ORGANISM: Homo sapiens

<400> SEQUENCE: 21
aaattcggta catcctcgac gg                                    22

<210> SEQ ID NO 22
<211> LENGTH: 23
<212> TYPE: DNA
<213> ORGANISM: Homo sapiens

<400> SEQUENCE: 22
ggaaggttca ggttgttttc tgc                                   23

<210> SEQ ID NO 23
<211> LENGTH: 21
<212> TYPE: DNA
<213> ORGANISM: Homo sapiens

<400> SEQUENCE: 23
ccaagtgctg ccgtcatttt c                                     21

<210> SEQ ID NO 24
<211> LENGTH: 21
<212> TYPE: DNA
<213> ORGANISM: Homo sapiens

<400> SEQUENCE: 24
ggctcgcagg gatgatttca a                                     21

<210> SEQ ID NO 25
<211> LENGTH: 20
<212> TYPE: DNA
<213> ORGANISM: Homo sapiens

<400> SEQUENCE: 25
tcgccttcct gctctacaat                                       20

<210> SEQ ID NO 26
<211> LENGTH: 20
<212> TYPE: DNA
<213> ORGANISM: Homo sapiens

<400> SEQUENCE: 26
cccatcttcg agaactgagc                                       20

<210> SEQ ID NO 27
<211> LENGTH: 21
<212> TYPE: DNA
<213> ORGANISM: Homo sapiens

<400> SEQUENCE: 27
gtggtgctgt cgctcttgat a                                     21

<210> SEQ ID NO 28
<211> LENGTH: 21
<212> TYPE: DNA
<213> ORGANISM: Homo sapiens

<400> SEQUENCE: 28
ccccagaaaa tggttcacgc t                                     21

<210> SEQ ID NO 29
<211> LENGTH: 20

```
<212> TYPE: DNA
<213> ORGANISM: Homo sapiens

<400> SEQUENCE: 29
ttctgcttgt catccccttt                                               20

<210> SEQ ID NO 30
<211> LENGTH: 20
<212> TYPE: DNA
<213> ORGANISM: Homo sapiens

<400> SEQUENCE: 30
cttctgccat gcctgtatca                                               20

<210> SEQ ID NO 31
<211> LENGTH: 21
<212> TYPE: DNA
<213> ORGANISM: Homo sapiens

<400> SEQUENCE: 31
cgagcaaggt ccttccatag t                                             21

<210> SEQ ID NO 32
<211> LENGTH: 20
<212> TYPE: DNA
<213> ORGANISM: Homo sapiens

<400> SEQUENCE: 32
ggtgtcggga ttccgatgac                                               20

<210> SEQ ID NO 33
<211> LENGTH: 23
<212> TYPE: DNA
<213> ORGANISM: Homo sapiens

<400> SEQUENCE: 33
agtcttccaa tcctactgtt gct                                           23

<210> SEQ ID NO 34
<211> LENGTH: 19
<212> TYPE: DNA
<213> ORGANISM: Homo sapiens

<400> SEQUENCE: 34
tccccgtcac ctccaatcc                                                19

<210> SEQ ID NO 35
<211> LENGTH: 21
<212> TYPE: DNA
<213> ORGANISM: Homo sapiens

<400> SEQUENCE: 35
tgctctgcct atcctctgag t                                             21

<210> SEQ ID NO 36
<211> LENGTH: 23
<212> TYPE: DNA
<213> ORGANISM: Homo sapiens

<400> SEQUENCE: 36
tcacatcctt ttcgaggttg tag                                           23

<210> SEQ ID NO 37
```

```
<211> LENGTH: 21
<212> TYPE: DNA
<213> ORGANISM: Homo sapiens

<400> SEQUENCE: 37
actgagaggc tccgagaaat g                                              21

<210> SEQ ID NO 38
<211> LENGTH: 19
<212> TYPE: DNA
<213> ORGANISM: Homo sapiens

<400> SEQUENCE: 38
gaaccccgca tcttggctt                                                 19

<210> SEQ ID NO 39
<211> LENGTH: 21
<212> TYPE: DNA
<213> ORGANISM: Homo sapiens

<400> SEQUENCE: 39
gggttttcgt ggttcacatc c                                              21

<210> SEQ ID NO 40
<211> LENGTH: 21
<212> TYPE: DNA
<213> ORGANISM: Homo sapiens

<400> SEQUENCE: 40
ctagacgctg gctcctcagt a                                              21

<210> SEQ ID NO 41
<211> LENGTH: 19
<212> TYPE: DNA
<213> ORGANISM: Homo sapiens

<400> SEQUENCE: 41
tgtccgtcag aacccatgc                                                 19

<210> SEQ ID NO 42
<211> LENGTH: 21
<212> TYPE: DNA
<213> ORGANISM: Homo sapiens

<400> SEQUENCE: 42
aaagtcgaag ttccatcgct c                                              21

<210> SEQ ID NO 43
<211> LENGTH: 19
<212> TYPE: DNA
<213> ORGANISM: Homo sapiens

<400> SEQUENCE: 43
ctccgtggcc ttagctgtg                                                 19

<210> SEQ ID NO 44
<211> LENGTH: 22
<212> TYPE: DNA
<213> ORGANISM: Homo sapiens

<400> SEQUENCE: 44
tttggagtac gctggatagc ct                                             22
```

```
<210> SEQ ID NO 45
<211> LENGTH: 22
<212> TYPE: DNA
<213> ORGANISM: Homo sapiens

<400> SEQUENCE: 45
acaactttgg tatcgtggaa gg                                              22

<210> SEQ ID NO 46
<211> LENGTH: 19
<212> TYPE: DNA
<213> ORGANISM: Homo sapiens

<400> SEQUENCE: 46
gccatcacgc cacagtttc                                                  19

<210> SEQ ID NO 47
<211> LENGTH: 20
<212> TYPE: DNA
<213> ORGANISM: Mus musculus

<400> SEQUENCE: 47
gaactctttc ggtcgtaccc                                                 20

<210> SEQ ID NO 48
<211> LENGTH: 20
<212> TYPE: DNA
<213> ORGANISM: Mus musculus

<400> SEQUENCE: 48
cgaatctgca ccgtagttga                                                 20

<210> SEQ ID NO 49
<211> LENGTH: 19
<212> TYPE: DNA
<213> ORGANISM: Mus musculus

<400> SEQUENCE: 49
cctggtgatg tccgacctg                                                  19

<210> SEQ ID NO 50
<211> LENGTH: 19
<212> TYPE: DNA
<213> ORGANISM: Mus musculus

<400> SEQUENCE: 50
ccatgagcgc atcgcaatc                                                  19

<210> SEQ ID NO 51
<211> LENGTH: 21
<212> TYPE: DNA
<213> ORGANISM: Mus musculus

<400> SEQUENCE: 51
tctacgcagt gcttctttgc c                                               21

<210> SEQ ID NO 52
<211> LENGTH: 23
<212> TYPE: DNA
<213> ORGANISM: Mus musculus

<400> SEQUENCE: 52 aaggggatc ttcagcttta gta                                              23
```

<210> SEQ ID NO 53
<211> LENGTH: 21
<212> TYPE: DNA
<213> ORGANISM: Mus musculus

<400> SEQUENCE: 53
gcgcccagac agaagtcata g                                           21

<210> SEQ ID NO 54
<211> LENGTH: 22
<212> TYPE: DNA
<213> ORGANISM: Mus musculus

<400> SEQUENCE: 54
agccttgcct ttgttcagta tc                                          22

<210> SEQ ID NO 55
<211> LENGTH: 22
<212> TYPE: DNA
<213> ORGANISM: Mus musculus

<400> SEQUENCE: 55
ccagcttcaa atctcacagc ag                                          22

<210> SEQ ID NO 56
<211> LENGTH: 24
<212> TYPE: DNA
<213> ORGANISM: Mus musculus

<400> SEQUENCE: 56
cttctttggg tattgcttgg gatc                                        24

<210> SEQ ID NO 57
<211> LENGTH: 22
<212> TYPE: DNA
<213> ORGANISM: Mus musculus

<400> SEQUENCE: 57
tcgagaccat ttactgcaac ag                                          22

<210> SEQ ID NO 58
<211> LENGTH: 21
<212> TYPE: DNA
<213> ORGANISM: Mus musculus

<400> SEQUENCE: 58
cattgccggt ggaaattcct t                                           21

<210> SEQ ID NO 59
<211> LENGTH: 19
<212> TYPE: DNA
<213> ORGANISM: Mus musculus

<400> SEQUENCE: 59
gctcagctgg ggactctac                                              19

<210> SEQ ID NO 60
<211> LENGTH: 19
<212> TYPE: DNA
<213> ORGANISM: Mus musculus

<400> SEQUENCE: 60
ggtctggccg aaggtttga                                              19

```
<210> SEQ ID NO 61
<211> LENGTH: 21
<212> TYPE: DNA
<213> ORGANISM: Mus musculus

<400> SEQUENCE: 61
aggtcggtgt gaacggattt g                                          21

<210> SEQ ID NO 62
<211> LENGTH: 23
<212> TYPE: DNA
<213> ORGANISM: Mus musculus

<400> SEQUENCE: 62
tgtagaccat gtagttgagg tca                                        23
```

TREATMENT OF AGING-ASSOCIATED CONDITIONS BY DNA DEGRADATION

RELATED APPLICATIONS

This application is a national stage filing under 35 U.S.C. § 371 of International Patent Application No. PCT/US2019/052947, filed Sep. 25, 2019, entitled "TREATMENT OF AGING-ASSOCIATED CONDITIONS BY DNA DEGRADATION," which was published under PCT Article 21(2) in English and which claims the benefit under 35 U.S.C. § 119(e) of U.S. Provisional Application No. 62/736,138, filed Sep. 25, 2018, entitled "DNASE2A-Mediated Clearance of Intrinsic DNA in Age-Related Inflammation and Disease Risks," the entire contents of each of which are incorporated by reference herein.

FIELD OF THE INVENTION

The present disclosure relates to methods for treating or protecting against aging-associated conditions by enhancing DNA degradation.

BACKGROUND

Systemic inflammation is central to aging-associated conditions. However, the intrinsic factors that induce inflammation are not well understood. Aging is associated with increased risk of many different pathological conditions, including heart disease, cancer, diabetes, and cognitive decline.

SUMMARY

The present disclosure is based, at least in part, on the finding that targeting DNA degradation may be an effective means for slowing or alleviating cellular effects related to aging-associated conditions, such as inflammation and tissue degeneration. Accordingly, aspects of the disclosure relate to methods for treating an aging-associated condition in a subject, comprising increasing expression, bioavailability, and/or bioactivity of a DNase enzyme in the subject.

Further aspects of the disclosure relate to methods for protecting against an aging-associated condition in a subject comprising increasing expression, bioavailability, and/or bioactivity of a DNase enzyme in the subject.

In some embodiments, the increased expression, bioavailability, and/or bioactivity of a DNase enzyme in the subject is facilitated by systemic or local administration of a DNase enzyme. In some embodiments, the increased expression, bioavailability, and/or bioactivity of a DNase enzyme in the subject is facilitated by gene therapy. In some embodiments, the increased expression, bioavailability, and/or bioactivity of a DNase enzyme in the subject is facilitated by administration of a small molecule to the subject.

In some embodiments, the DNase enzyme is a lysosomal nuclease enzyme. In some embodiments, the DNase enzyme is DNASE2A.

In some embodiments, the DNase enzyme is a derivative of DNASE2A. In some embodiments, the derivative of DNASE2A is functionally enhanced relative to DNASE2A.

In some embodiments, the aging-associated condition is aging-associated inflammation. In some embodiments, the aging-associated condition is cellular senescence. In some embodiments, the aging-associated condition is a laminopathy. In some embodiments, the aging-associated condition is an interferonopathy. In some embodiments, the aging-associated condition is ataxia telangiectasia (A-T). In some embodiments, the aging-associated condition is Hutchison-Gilford progeria.

In some embodiments, the aging-associated inflammation and/or cellular senescence is induced or enhanced by treatment with a chemotherapeutic agent. In some embodiments, the chemotherapeutic agent is a DNA damaging agent. In some embodiments, the DNA damaging agent is cytarabine (ara-C).

In some embodiments, the subject is identified as having elevated levels of extranuclear DNA relative to a control. In some embodiments, the subject is identified as having elevated levels of SA-β-gal activity relative to a control. In some embodiments, the subject is identified as having elevated levels of one or more autophagy genes, optionally ATG5, BECLIN1, P62, or PTEN; one or more autophagosome marker, optionally LC3; one or more lysosomal protein, optionally LAMP1; and/or one or more inflammatory genes, optionally MX1, CXCL10, or IL-6 relative to a control.

In some embodiments, the method for treating an aging-associated condition comprises identifying a subject as having elevated levels of extranuclear DNA relative to a control, and increasing expression, bioavailability, and/or bioactivity of a DNase enzyme in the subject.

In some embodiments, the method for treating an aging-associated condition comprises identifying a subject as having elevated levels of SA-β-gal activity relative to a control, and increasing expression, bioavailability, and/or bioactivity of a DNase enzyme in the subject.

In some embodiments, the method for treating an aging-associated condition comprises identifying a subject as having elevated levels of one or more autophagy genes, optionally ATG5, BECLIN1, P62, or PTEN; one or more autophagosome marker, optionally LC3; one or more lysosomal protein, optionally LAMP1; and/or one or more inflammatory genes, optionally MX1, CXCL10, or IL-6 relative to a control, and increasing expression, bioavailability, and/or bioactivity of a DNase enzyme in the subject.

In some embodiments, the control is a sample from a subject who does not have an aging-associated condition. In some embodiments, the subject is a human.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations of thereof herein, is meant to encompass the items listed thereafter and equivalents thereof as well as additional items.

BRIEF DESCRIPTION OF THE DRAWINGS

The following drawings form part of the present specification and are included to further demonstrate certain aspects of the present disclosure, which may be better understood by reference to one or more of these drawings in combination with the detailed description of specific embodiments presented herein. The accompanying drawings are not intended to be drawn to scale. The drawings are illustrative only and are not required for enablement of the disclosure. For purposes of clarity, not every component may be labeled in every drawing. In the drawings:

FIG. 1A shows immunofluorescence (IF) staining of anti-dsDNA in young and old WI38 cells. Insets, enlarged cells; scale bar, 50 μm. Quantitation shows manual cell count with extranuclear DNA in percentage (left panel) and signal intensity per cell in nucleus and cytosol (right panel). FIG. 1B shows a TUNEL assay detecting DNA fragmentation in young and old MRC5 cells without or with Ara-C treatment. Scale bar, 50 μm. FIG. 1C shows IF staining and quantitation of anti-dsDNA in young and old MRC5 cells untreated or treated with Ara-C. Scale bar, 20 μm. FIG. 1D shows IF staining and quantitation of anti-dsDNA in young and old MRC5 cells untreated or treated with leptomycin B (LMB, 20 nM, 24 hr). Insets show enlarged cells. Scale bar, 50 μm. FIG. 1E shows dual staining of dsDNA and NUP98 in old MRC5 cells. Dotted squares highlight DNA patterns indicated; scale bar, 20 μm. Results are representative of 3 (FIG. 1A) or 2 (FIGS. 1B-1E) independent experiments. Ara-C treatment: 10 μM, 24 hr. DAPI was used as a counterstain in FIGS. 1B-1E. Quantitation was based on 5 random fields at 10× or 20× in representative experiment. Values in quantitation are mean±SEM. p-value of significance by t test, *p<0.05, p<0.01, *p<0.005, ****p<0.0001.

FIG. 2A provides a graph depicting expression of IFNI-inducible and inflammatory genes in young and old WI38 cells by RT-qPCR. UT: untreated. AraC: treated with AraC at 10 μM, 24 hr. FIG. 2B provides a heat map showing significantly upregulated (top) or downregulated (bottom) genes in old versus young MRC5 cells by NanoString in three biological replicates. FIG. 2C provides a heat map showing DEGs in old cells that overlap with IFNI-regulated genes restricted to fibroblasts (35 upregulated on top and 31 downregulated genes on bottom). FIG. 2D shows enriched GSEA-ranked gene sets in old compared with young cells across IMR90, MRC5, and WI38 cell lines based on RNA-seq data. Enrichment in old cells is at the low end of the ranking; FDR for significance. FIG. 2E provides a heat map showing unsupervised clustering of young and old cells based on STING-related genes. FIG. 2F provides graphs showing gene expression of MX1, CXCL10, and IL-6 in young and old MRC5 cells by RT-qPCR. Cells were either: untreated or treated with bafilomycin A (BAF, 20 nM) or rapamycin (RAPA, 1 nM) for 8 hr. Significance is relative to untreated cells. FIG. 2G provides graphs showing transcript expression of MX1 and IFIT1 in young and old MRC5 cells measured by RT-qPCR after knocking down cGAS, STING, or TBK1 by transfected siRNAs. Significance is relative to siNEG, nontargeting control. Results in FIG. 2A, FIG. 2F, and FIG. 2G are representative of 2 independent experiments, with p-values of significance by t test.

FIGS. 3A-3G provide data showing DNA accumulation and sensing in aging-associated conditions. FIG. 3A shows IF staining and quantitation of anti-dsDNA in healthy (H), ataxia (AT), and progeria (PS) skin fibroblasts. Numbers represent different fibroblasts of each genotype. One-way ANOVA among samples, p=0.0038, and significance of grouped genotype by t test as indicated. FIG. 3B shows a list of enriched hallmark gene sets in AT (top) and PS (bottom) by GSEA with FDR<0.25. FIG. 3C provides graphs showing TNF-α, MX1, and IL-6 transcript expression of H, AT, and PS fibroblasts assessed by RT-qPCR, p<0.0001 among samples by 1-way ANOVA for all 3 genes. Asterisks indicate significance of individual cells versus H1 for TNF-α, H4 and H5 for MX1, and all healthy cells for IL-6 by Tukey's test. FIG. 3D provides an immunoblot showing DNA-sensing mediators in H, AT, and PS cells. Double bands in total STING are visible in some AT cells. β-ACTIN was used as a loading control. FIG. 3E provides data showing IF staining and quantitation of pIRF3 and pTBK1 in H, AT, and PS cells. DAPI was used as a counterstain. Significance among samples for both phospho-proteins, p<0.0001, 1-way ANOVA; and individual cells versus H1 and H4 by Tukey's test as indicated. FIGS. 3F-3G provide data showing H, AT, and PS cells with STING knocked down by transfected siRNAs and assessed for MX1 and IL-6 expressions by RT-qPCR (FIG. 3F), and p16 expression by IF staining (FIG. 3G). Two-way ANOVA by genotype and siSTING in FIG. 3G, **p<0.0001. DAPI was used as a counterstain. Asterisks denote significance of siSTING versus siNEG control in individual cells by t test. Results in FIG. 3A, FIG. 3C, FIG. 3D, FIG. 3E, FIG. 3F, and FIG. 3G are representative of 2 independent experiments.

FIGS. 4A-4E provide data showing that DNA burden impacts age-related inflammation. FIG. 4A shows digestion of 50 μg calf thymus DNA by cell lysates (l) from 2 million young or old MRC5 cells. Degraded DNA fragments were visualized on 0.7% agarose gel by ethidium bromide. Recombinant DNASE2 (10 μg/ml) was used as a positive control. L: DNA ladder. The arrows denote saturated amounts of DNA. FIG. 4B provides graphs showing MX1 and CXCL10 mRNA expression assessed by RT-qPCR in young and old MRC5 cells after knocking down DNASE2A using transfected siRNAs; t test significance relative to siNEG, nontargeting control. FIGS. 4C-4E provide data showing young and old MRC5 cells transduced with a DNASE2A open reading frame (ORF) for constitutive overexpression, and examined for anti-dsDNA staining by IF (FIG. 4C), SA-β-gal activity (FIG. 4D), and expression of inflammatory and cell-cycle genes by RT-qPCR (FIG. 4E). EGFP: negative control; scale bar, 20 μm in FIG. 4C and 50 μm in FIG. 4D. Significance was based on eGFP values by t test. All data are representative of at least 2 independent experiments.

FIG. 5A provides contour plots showing FSC (forward scatter) for cell size and SSC (side scatter) for granularity in Dnase2a$^{+/+}$ and Dnase2a$^{-/-}$ MLFs. FIG. 5B provides a graph showing cell proliferation of Dnase2a$^{+/+}$ and Dnase2a$^{-/-}$ MLFs by manual count with trypan blue, **p<0.0001 by phenotype, 2-way ANOVA. FIG. 5C shows SA-β-gal activity and quantitation of Dnase2a$^{+/+}$ and Dnase2a$^{-/-}$ MLFs without or with Ara-C treatment (10 μM, 24 hr); scale bar, 50 μm. FIG. 5D shows representative SA-β-gal staining of Dnase2a$^{+/+}$ and Dnase2a$^{-/-}$ mouse tissues as indicated. Quantitation was based on 5 random fields of 5× or 10× images of representative pairs of mice; scale bar, 100 μm in kidney and liver, 200 μm in brain. FIG. 5E provides an immunoblot of HP1β and p16 in Dnase2a$^{+/+}$ and Dnase2a$^{-/-}$ kidney tissues. β-ACTIN was used as a loading control. FIG. 5F provides graphs showing transcript expression of cell-cycle genes and SASP factors in kidney tissues of Dnase2a$^{+/+}$ (n=4), Dnase2a$^{-/-}$ (n=4), and Dnase2a; Sting double KO (DKO) (n=3) mice by RT-qPCR. FIG. 5G provides a graph showing quantitation of SA-β-gal activity in Dnase2a$^{+/+}$, Dnase2a$^{-/-}$, and DKO MLFs, untreated or treated with Ara-C (10 μM, 24 hr). Numbers indicate single clones of each genotype. p<0.0001, for genotype and Ara-C-treatment by 2-way ANOVA, and t test between Dnase2a$^{-/-}$ and DKO MLFs as indicated. FIG. 5H provides a graph showing cell growth over serial passage in Dnase2a$^{+/+}$, Dnase2a$^{-/-}$, and DKO MLFs where an equal number of cells are re-plated at each split. Effect by genotype between Dnase2a$^{-/-}$ and DKO, *p<0.0001, 2-way ANOVA. Data are representative of 2 independent experiments in FIG. 5A-FIG. 5C, FIG. 5G, and FIG. 5H, and 3 pairs of age and sex-matched littermates in FIGS. 5D-5E. p-value of significance by t test or as indicated.

FIG. 7A shows a list of 59 significant up- or down-regulated genes in old vs. young MRC5 cells among 413 innate and inflammatory genes in the NanoString panel. FIG. 7B shows Type I IFN genes that overlap with DEGs in old cells, 35 up-regulated and 31 down-regulated. FIG. 7E shows horizontal bar plots of overlapping genes in FIG. 7B based on log 2 fold change expression in old vs. young in cell lines indicated. Genes follow the order from high to low fold change in MRC5. FIG. 7F shows enriched GSEA-ranked gene sets in old cells across the 3 cell lines of IMR90, MRC5 and WI38, FDR<0.25 highlighted. FIG. 7G shows a list of STING-related genes with DEGs in old cells highlighted.

DETAILED DESCRIPTION OF THE INVENTION

Figure 1A:
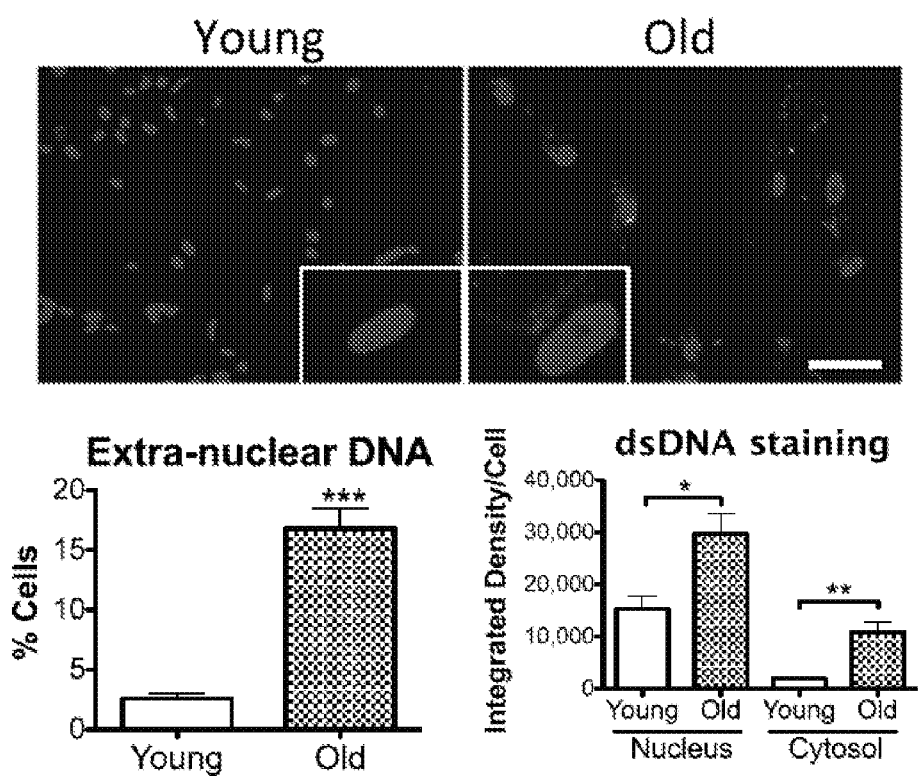
FIGS. 1A-1E provide data showing that old cells accumulate nuclear DNA in the cytosol.

Aspects of the present disclosure relate to methods for treating aging-associated conditions in a subject by DNA degradation. It was determined that damaged nuclear DNA is an intrinsic trigger that induces persistent inflammation in aging cells. Along with cumulative damage, aging cells accumulate extra-nuclear DNA that activates innate cytosolic DNA sensors leading to hyper-inflammation. Similar DNA accumulation is found in cells from patients with disorders associated with aging. Young cells or cells from heathy donors do not exhibit excess intrinsic nuclear DNA. The present disclosure relates to methods of reducing DNA levels and inflammatory responses by DNA degradation, such as through increased expression, bioavailability, and/or bioactivity of a DNase enzyme in a subject.

Such methods may be useful for clinical purposes, such as for treating or protecting against aging-associated conditions, including systemic inflammation, and may have biological implications in autoimmunity, chemotherapy, and cancer initiation and progression. Methods described herein may also be useful for non-clinical applications, such as research purposes, including, e.g., studying the mechanism of damaged nuclear DNA as a driver of aging-associated conditions and/or related biological processes such as trafficking, sensing, and degradation, and developing new therapies for aging-associated conditions based on such studies.

Aging-Associated Conditions

Methods disclosed herein relate to treatment of, or protection against, aging-associated conditions. As used herein, an "aging-associated condition" refers to a condition that is more likely to occur, or more frequently occurs, in a cell or organism as the cell or organism ages. In some embodiments, the aging-associated condition is aging-associated inflammation and/or cellular senescence. In some embodiments, an aging-associated condition is a disorder that is associated with inflammation, including systemic inflammation, and/or cellular senescence.

As used herein, "inflammation" refers to a response by the immune system to stimuli. Inflammation can be acute or chronic. As used herein "systemic inflammation" refers to inflammation throughout a large portion, or all of, the body of an organism. As used herein, "aging-associated inflammation" refers to inflammation that is associated with, is more likely to occur, or more frequently occurs, in a cell or organism as the cell or organism ages.

As used herein, "cellular senescence" refers to a state in which cells can no longer divide. Senescence is a distinguishing feature of aging cells in which the cells may exhibit unrepaired or persistent double-stranded breaks (DSBs) and dramatic chromatin changes with fragments budding off the nucleus and being processed into autophagic vesicles. In some embodiments, cells undergoing senescence or that have undergone senescence exhibit elevated levels of extranuclear DNA and/or exhibit a pro-inflammatory secretory phenotype.

Heightened inflammation is observed in aging tissues, and in the blood of older adults in large epidemiologic studies, with consistently higher basal levels of C-reactive protein and abundant pro-inflammatory cytokines like IL-6, IFN-β, and TNF-α (Fagiolo et al., 1993; Roubenoff et al., 2003; Singh & Newman, 2011). Such alteration is often viewed as noncell autonomous, for example senescent cells, which increase with aging, may modulate inflammation through secretion of cytokines (e.g., senescence-associated secretory phenotype, SASP (Coppé et al., 2010)).

Without wishing to be bound by any theory, in some embodiments, inflammation may be triggered by activation of a cell-autonomous pathway through which damaged nuclear DNA is trafficked to the cytosol where it activates innate cytosolic DNA sensors. Nuclear DNA released to the cytosol after cumulative damage may contribute to persistent inflammation in aging cells. Senescent cells, which increase with aging, may modulate inflammation through secretion of cytokines and can result in a senescence-associated secretory phenotype ("SASP"). Secreted pro-inflammatory cytokines may include but are not limited to IL-6, IFN-β, and TNF-α.

As shown in Example 1, it was demonstrated herein that older cells harbored higher levels of extranuclear DNA compared to younger cells. Extranuclear DNA was exported by a leptomycin B-sensitive process, degraded through the autophago-some-lysosomal pathway and triggered innate immune responses through the DNA-sensing cGAS-STING pathway. Patient cells from the aging diseases ataxia and progeria also displayed extranuclear DNA accumulation, increased pIRF3 and pTBK1, and STING-dependent p16 expression. Removing extranuclear DNA in old cells using DNASE2A reduced innate immune responses and senescence-associated (SA) β-gal enzyme activity. Cells and tissues of Dnase2a−/− mice with defective DNA degradation exhibited slower growth, higher activity of β-gal, or increased expression of HP-10 and p16 proteins, while Dnase2a−/−; Sting−/− cells and tissues were rescued from these phenotypes, supporting a role for extranuclear DNA in senescence.

Without wishing to be bound by any theory, in some embodiments, damaged DNA in older cells may be caused by replication errors, radiation, oxygen, bacterial infection, and/or oncogenes. Toxic DSBs are associated with senescence and inflammation in aged human tissues (Lu et al., 2004). Without wishing to be bound by any theory, in some embodiments, weakened or altered nuclear envelope in old cells can facilitate export of DNA from the nucleus.

Aspects of the present disclosure encompass any type of cell, including cells that are capable of senescence. Examples of cells capable of senescence include, but are not limited to, epithelial cells, fibroblasts, leukocytes, monocytes, dendritic cells, B cells, T cells, NK cells, smooth muscle cells, osteoblasts, chondrocytes, endothelial cells, myoblasts, and glial cells. In some embodiments, an increase in expression of autophagy genes in a cell may be a marker of senescence. Autophagy genes include but are not limited to ATG5, BECLIN1, P62, or PTEN. In some embodiments, an increase in expression of certain protein products, such as autophagosome markers or lysosomal proteins, may be a marker for senescence. Autophagosome markers include but are not limited to the autophagosome marker LC3. Lysosomal proteins include but are not limited to the lysosomal protein LAMP1. In some embodiments, an increase in expression of one or more inflammatory genes in a cell may be a marker of senescence. Inflammatory genes include but are not limited to MX1, CXCL10, or IL-6.

In some embodiments, cells associated with the disclosure have elevated levels of gene expression in the inflammatory response, the IFN-α response, IL-6-JAK-STAT3 signaling, and/or TNF-α signaling pathways.

Aging-associated conditions include disorders. In some embodiments, the disorder is a type of laminopathy. As used herein, "laminopathy" refers to a disorder caused by one or more mutations in one or more genes encoding proteins of the nuclear lamina or a disorder caused by any other disruption to the nuclear lamina. Laminopathies can result in: deteriorated nuclear architecture; defective or incomplete nuclear perimeter; and/or increased cytosolic DNA due to a weakened or altered nuclear envelope that facilitates nuclear DNA escape. Laminopathies can exhibit clinical symptoms including but not limited to progeria or premature aging. In some embodiments, a mutation in the gene that encodes LAMIN A (LMNA) can result in symptoms of progeria or premature aging. In some embodiments, the laminopathy is classified as Hutchison-Gilford progeria (HGPS).

In some embodiments, the disorder is a neurodegenerative disorder. As used herein, "a neurodegenerative disorder" refers to a disorder exhibiting progressive degeneration and/or death of neurons in the central nervous system. Non-limiting examples of neurodegenerative disorders include Parkinson's disease (PD), Alzheimer's disease (AD), Huntington's disease (HD), prion disease, motor neurone diseases (MND), spinocerebellar ataxia (SCA), and spinal muscular atrophy (SMA).

In some embodiments, the disorder is ataxia telangiectasia. As used herein, "ataxia telangiectasia" refers to a neurodegenerative syndrome caused by gene defects in ATM, which is involved in double-stranded DNA break repair. Ataxia telangiectasia can result in excess cytosolic DNA as a result of increased DNA damage. Ataxia telangiectasia can produce clinical symptoms of premature aging.

In some embodiments, the disorder is a type of interferonopathy. As used herein, "interferonopathy" refers to a genetic disorder caused by Mendelian mutations resulting in the disturbance of the homeostatic control of the interferon-mediated immune response. An interferonopathy can result in a loss of degradation components causing an increase in interferon-mediated autoinflammation. An interferonopathy can produce clinical symptoms of aging-associated conditions.

It should be appreciated that aging-associated conditions may be exhibited in subjects of advanced age. However, aging-associated conditions may also be exhibited in subjects who are not of an advanced age, including young subjects, for example in the context of a disorder that causes premature aging. Examples of disorders that cause premature aging include Hutchinson-Gilford syndrome and Werner syndrome.

Other aging-associated conditions include heart disease, cancer, diabetes, cognitive decline, arthritis, and osteoporosis.

It should also be appreciated that aging, including premature aging, in a subject could be induced or enhanced by an external factor applied to the subject, such as environmental factors or medical treatments. Aspects of the disclosure encompass subjects in whom aging, including premature aging, is induced or enhanced by environmental factors or medical treatments. In some embodiments, aging, including premature aging, may be induced or enhanced by treatment with a chemotherapeutic agent and/or treatment with radiation therapy. Chemotherapeutic agents include DNA damaging agents. In some embodiments, the chemotherapeutic agent is cytarabine (Ara-C).

As used herein, "treating" an aging-associated condition in a subject refers to ameliorating at least one symptom of the aging-associated condition, or slowing the advancement of at least one aspect of the aging-associated condition. As used herein, the term "protecting against" an aging-associated condition in a subject refers to the prevention or delay in development of an aging-associated condition in a subject.

In some embodiments, the subject is a mammal. In some embodiments, the subject is a human or a non-human primate. In some embodiments, the subject is a human patient diagnosed with an aging-associated condition. In some embodiments, the subject is a companion animal, such as a dog or a cat. In some embodiments, the subject is a farm animal, such as a horse, cow, sheep, goat, or pig. In some embodiments, the subject is a rodent, such as a mouse or a rat.

In some embodiments, the method comprises treating a subject after the subject has developed symptoms of an aging-associated condition. In some embodiments, the method comprises treating a subject after the subject has been diagnosed with an aging-associated condition. In some embodiments, the method comprises protecting against an aging-associated condition in a subject prior to the subject developing symptoms of an aging-associated condition and/or prior to the subject being diagnosed with an aging-associated condition.

In some embodiments, methods comprise the application or administration of a composition including one or more active agents to a subject who has an aging-associated condition, or to a subject who exhibits at least one symptom of an aging-associated condition, with the purpose to cure, heal, alleviate, relieve, alter, remedy, ameliorate, improve, or affect the aging-associated condition, or at least one symptom of the aging-associated condition. In some embodiments, the aging-associated condition develops, progresses, or is worsened as a result of prior treatment with a chemotherapeutic agent.

DNA Degradation

Methods described herein are based, at least in part, on the identification that excess damaged nuclear DNA leads to elevated cytosolic DNA, and that cytosolic DNA is more abundant in old cells compared to young cells. Accordingly, aspects of the disclosure relate to methods for treating a subject for an aging-associated condition, or protecting a subject against an aging-associated condition, by increasing DNA degradation in a subject or by triggering autophagy in a subject. In some embodiments, DNA degradation is increased in a subject by increasing expression, bioavailability, and/or bioactivity of a DNase enzyme in the subject.

As used herein, a "DNase" refers to an enzyme with the ability to cleave or degrade DNA by catalyzing the hydrolytic cleavage of phosphodiester linkages in the DNA backbone. Methods described herein are based, at least in part, on the ability of DNase enzymes to cleave and degrade damaged nuclear DNA.

In some embodiments, the DNase is a lysosomal nuclease enzyme. As used herein, a "nuclease" refers to an enzyme that cleaves the chains of nucleotides in nucleic acids into smaller units. As used herein, a "lysosomal nuclease enzyme" refers to a nuclease that is localized to or functionally active within the lysosome of a cell.

In some embodiments, the lysosomal nuclease enzyme is deoxyribonuclease II alpha (DNASE2A) or a functional fragment or derivative thereof. A functional fragment of DNASE2A could include any portion of DNASE2A that retains at least part of a functional feature of full-length DNASE2A, such as the DNase ability of full-length DNASE2A.

As used herein, a "derivative" or "variant" of DNASE2A refers to an enzyme that encompasses one or more modifications or substitutions compared with the wildtype DNASE2A enzyme. In some embodiments, a derivative or variant DNASE2A enzyme may have increased bioavailability or bioactivity in a subject relative to a wildtype DNASE2A enzyme. In some embodiments, a derivative or variant DNASE2A may be functionally enhanced relative to a wildtype DNASE2A enzyme. As used herein, a derivative or variant DNASE2A that is "functionally enhanced" refers to a DNASE2A that exhibits an increase or improvement in one or more activities relative to a wildtype DNASE2A enzyme. In some embodiments, activities that may be functionally enhanced include but are not limited to increased substrate binding affinity, increased specificity in substrate binding, increased active site availability, and/or increased activity under cytosolic pH.

In some embodiments, enhancing degradation of DNA is accomplished by increasing expression of a DNase enzyme, such as DNASE2A, or a fragment or derivative thereof. Increasing expression of a DNase enzyme can include increasing endogenous and/or exogenous expression of a DNase enzyme. For example, expression of an endogenous enzyme can be increased by overexpressing the enzyme, such as by manipulating regulatory regions that control expression of the enzyme. In some embodiments, increasing expression of an endogenous enzyme is accomplished by modifying the promoter of the enzyme. Modifying the promoter could involve substituting an endogenous promoter with a different promoter, or mutating or editing the endogenous promoter. In some embodiments, the copy number of an endogenous enzyme is increased. In some embodiments, an enzyme is expressed exogenously in a cell. Exogenous expression can include, for example, expression on a plasmid and/or integration into a chromosome. In some embodiments, increased expression of a DNase enzyme can increase the rate of cytosolic DNA degradation.

In some embodiments, enhancing degradation of DNA is accomplished by increasing the bioavailability of a DNase enzyme. As used herein, "bioavailability" refers to the pharmacological absorption of an agent, such as an enzyme, administered to a subject. In some embodiments, increasing the bioavailability of a DNase enzyme can increase the rate of cytosolic DNA degradation within a subject.

In some embodiments, enhancing degradation of DNA is accomplished by increasing bioactivity of a DNase enzyme. As used herein, "bioactivity" refers to enzymatic activity and/or enzymatic efficiency. In some embodiments, increased bioactivity of a DNase enzyme can increase the rate of cytosolic DNA degradation.

Increased expression, bioavailability, and/or bioactivity of a DNase enzyme in a subject may be accomplished by systemic or local administration of a DNase enzyme using any method known to one of ordinary skill in the art.

In some embodiments, increased expression, bioavailability, and/or bioactivity of a DNase enzyme in a subject is facilitated by gene therapy. As used herein, "gene therapy" refers to introducing a gene into a cell of a subject. Expression of the gene in a cell can be stable or can be inducible. It should be appreciated that any method for gene therapy known to one of ordinary skill in the art may be compatible with aspects of the disclosure. For example, non-limiting examples of methods associated with gene therapy are disclosed in and incorporated by reference from: Moss (2014) *Radiol Technol*. November-December; 86(2):155-80; High et al. (2019) *N Engl J Med*. August 1; 381(5):455-464; and Ingusci et al. (2019) *Front Pharmacol*. July 1; 10:724. Inducible gene expression systems for mammalian studies are further described in and incorporated by reference from Kallunki et al. (2019) *Cell* July 30; 8(8). pii: E796. In some embodiments, gene therapy is mediated by the use of adeno-associated virus (AAV). In some embodiments, a DNase enzyme is expressed in a gene therapy vector, such as an AAV vector. In some embodiments, the AAV serotype is AAV1, AAV2, AAV3, AAV4, AAV5, AAV6, AAV7, AAV8, AAV9, AAV10, or AAV11.

In some embodiments, increased expression, bioavailability, and/or bioactivity of a DNase enzyme in a subject is facilitated by administration of a small molecule to a subject. One of ordinary skill in the art would be able to screen small molecules and identify those that increase expression, bioavailability, and/or bioactivity of a DNase enzyme. One of ordinary skill in the art would also be able to optimize a formulation comprising a small molecule and would be able to optimize dosing of a small molecule for administration to a subject.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of sepsis. Alternatively, sustained continuous release formulations of therapeutic agent may be appropriate. Various formulations and devices for achieving sustained release are known in the art.

Aspects of the present disclosure provide, in some embodiments, a pharmaceutical composition comprising a DNase enzyme, or a small molecule, and a pharmaceutically acceptable carrier. Suitable carriers may be readily selected by one of ordinary skill in the art. For example, in some embodiments, a suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water.

In some embodiments, methods for treating a subject for an aging-associated condition involve triggering autophagy in the subject. In some embodiments, autophagy is triggered by fasting. In some embodiments, autophagy is triggered by reducing carbohydrate consumption.

Identification of Subjects

Methods described herein can be used to select a subject with an aging-associated condition. For example, in some embodiments, subjects may be identified based on having elevated levels of extranuclear DNA. In other embodiments, subjects may be identified as having elevated or reduced levels of certain enzymatic activity, gene expression, or protein expression. As used herein, "elevated levels" refers to levels that are higher in a sample from a test subject relative to a control. As used herein, "reduced levels" refers to levels that are lower in a sample from a test subject relative to a control.

In some embodiments, a subject is identified as having elevated levels of extranuclear DNA relative to a control. It should be appreciated that levels of extranuclear DNA could be measured using any method known to one of ordinary skill in the art. In some embodiments, a subject is identified as having elevated levels of senescence-associated β-gal enzyme (SA-β-gal) activity. It should be appreciated that levels of SA-β-gal activity could be measured using any method known to one of ordinary skill in the art.

In some embodiments, a subject is identified as having elevated levels of one or more autophagy genes, including but not limited to ATG5, BECLIN1, P62, or PTEN relative to a control. It should be appreciated that levels of one or more autophagy genes could be measured by any method known to one of ordinary skill in the art. In some embodiments, a subject is identified as having elevated levels of one or more autophagosome markers, including but not limited to autophagosome marker LC3 relative to a control. It should be appreciated that levels of autophagosome markers, such as LC3, could be measured by any method known to one of ordinary skill in the art.

In some embodiments, a subject is identified as having elevated levels of one or more lysosomal proteins, including but not limited to lysosomal protein LAMP1 relative to a control. It should be appreciated that levels of lysosomal proteins, such as LAMP1, could be measured by any method known to one of ordinary skill in the art.

In some embodiments, a subject is identified as having elevated levels of one or more inflammatory genes, including but not limited to MX1, CXCL10, or IL-6 relative to a control. It should be appreciated that levels of inflammatory genes, such as MX1, CXCL10, or IL-6, could be measured by any method known to one of ordinary skill in the art.

In some embodiments, a control is a sample from a subject who does not have or is not suspected of having an aging-associated condition. In some embodiments, a control is a sample from a healthy subject. A control subject may also represent a population of healthy subjects, who preferably would have matched features (e.g., age, gender, ethnic group) to the subject being analyzed by a method described herein.

In some embodiments, a control is a predetermined value. In some embodiments, a predetermined value is based on a predictive value or a value that is based on data from one or more other subjects. In some embodiments, a predetermined value is based on data from a population of subjects. Such a predetermined value can represent the fraction and/or the level in a population of subjects that do not have or are not at risk for an aging-associated condition (e.g., the average fraction and/or the average level in the population of healthy subjects). It can also represent the fraction and/or level in a population of subjects that have the target condition or disease.

The predetermined value can take a variety of forms. For example, it can be a single cut-off value, such as a median or mean. In some embodiments, such a predetermined value can be established based upon comparative groups, such as where one defined group is known to have an aging-associated condition and another defined group is known to not have an aging-associated condition. Alternatively, the predetermined value can be a range, for example, a range representing the fraction and/or the levels in a control population.

The control level as described herein can be determined by any technology known in the art. In some examples, the control level can be obtained by performing a conventional method (e.g., the same assay for obtaining the fraction and/or the level in a test sample as described herein) on a control sample as also described herein. In other examples, the fraction and/or the level can be obtained from members of a control population and the results can be analyzed to obtain the control level (a predetermined value) that represents the fraction and/or the level in the control population.

By comparing the fraction and/or the level of one or more components in a sample from a subject to a control as described herein, it can be determined whether the subject has or is at risk for having an aging-associated condition. When the control represents the value range of the fraction and/or the level of a component in a population of subjects having an aging-associated condition, the value of the fraction and/or the level of the component in a sample of a subject falling in the range may indicate that the subject has or is at risk for having an aging-associated condition.

In some embodiments, if a subject is identified as having or being at risk for an aging-associated condition, then the subject is treated for the aging-associated condition by increasing expression, bioavailability, and/or bioactivity of a DNase enzyme in the subject.

For example, in some embodiments, methods comprise identifying a subject as having elevated levels of extra-nuclear DNA relative to a control, and increasing expression, bioavailability, and/or bioactivity of a DNase enzyme in the subject.

In other embodiments, methods comprise identifying a subject as having elevated levels of SA-β-gal activity relative to a control, and increasing expression, bioavailability, and/or bioactivity of a DNase enzyme in the subject.

In other embodiments, methods comprise identifying a subject as having elevated levels of: (i) one or more autophagy genes, optionally ATG5, BECLIN1, P62, or PTEN; (ii) one or more autophagosome marker, optionally LC3; (iii) one or more lysosomal protein, optionally LAMP1; and/or (v) one or more inflammatory genes, optionally MX1, CXCL10, or IL-6 relative to a control; and increasing expression, bioavailability, and/or bioactivity of a DNase enzyme in the subject.

If a subject is identified as not responsive to a treatment, a higher dose and/or frequency of dosage of the therapeutic agent can be administered to the subject. In some embodiments, the dosage or frequency of dosage of the therapeutic agent is maintained, lowered, or ceased in a subject identified as responsive to the treatment or not in need of further treatment. Alternatively, a different treatment can be applied to the subject who is found as not responsive to the first treatment.

Sequences:
A representative sequence for Human
Deoxyribonuclease 2, Lysosomal (DNASE2A) DNA is
provided by NCBI Reference Sequence: NM_001375.3
(SEQ ID NO: 1)
AGTCCTGGCCTCTGATGTAACCCAGCGCCCCGCAGTCCCGACACAGATTC

CTGGATCTCAGCCCCATAGCAGCTATGATCCCGCTGCTGCTGGCAGCGCT

GCTGTGCGTCCCCGCCGGGGCCCTGACCTGCTACGGGGACTCCGGGCAGC

CTGTAGACTGGTTCGTGGTCTACAAGCTGCCAGCTCTTAGAGGGTCCGGG

GAGGCGGCGCAGAGAGGGCTGCAGTACAAGTATCTGGACGAGAGCTCCGG

AGGCTGGCGGGACGGCAGGGCACTCATCAACAGCCCGGAGGGGGCCGTGG

GCCGAAGCCTGCAGCCGCTGTACCGGAGCAACACCAGCCAGCTCGCCTTC

CTGCTCTACAATGACCAACCGCCTCAACCCAGCAAGGCTCAGGACTCTTC

CATGCGTGGGCACACGAAGGGTGTCCTGCTCCTTGACCACGATGGGGGCT

TCTGGCTGGTCCACAGTGTACCTAACTTCCCTCCACCGGCCTCCTCTGCT

GCATACAGCTGGCCTCATAGCGCCTGTACCTACGGGCAGACCCTGCTCTG

TGTGTCTTTTCCCTTCGCTCAGTTCTCGAAGATGGGCAAGCAGCTGACCT

ACACCTACCCCTGGGTCTATAACTACCAGCTGGAAGGGATCTTTGCCCAG

GAATTCCCCGACTTGGAGAATGTGGTCAAGGGCCACCACGTTAGCCAAGA

ACCCTGGAACAGCAGCATCACACTCACATCCCAGGCCGGGGCTGTTTTCC

AGAGCTTTGCCAAGTTCAGCAAATTTGGAGATGACCTGTACTCCGGCTGG

TTGGCAGCAGCCCTTGGTACCAACCTGCAGGTCCAGTTCTGGCACAAAAC

TGTAGGCATCCTGCCCTCTAACTGCTCGGATATCTGGCAGGTTCTGAATG

TGAACCAGATAGCTTTCCCTGGACCAGCCGGCCCAAGCTTCAACAGCACA

GAGGACCACTCCAAATGGTGCGTGTCCCCAAAAGGGCCCTGGACCTGCGT

GGGTGACATGAATCGGAACCAGGGAGAGGAGCAACGGGGTGGGGGCACAC

TGTGTGCCCAGCTGCCAGCCCTCTGGAAAGCCTTCCAGCCGCTGGTGAAG

AACTACCAGCCCTGTAATGGCATGGCCAGGAAGCCCAGCAGAGCTTATAA

GATCTAACCCTTATGGCCAGGTGCAGTGGCTCACGTATGTAATCCCAGCA

CTTTGGGAAGCCAAGGAGGGAGGATCACTTGAACTCAGGAATTCGAGACC

AGCCTGGGCTACATAGTGAGACCACATCTCTACTAGAACTTAAAAAAAGT

TAGCCAGGCACGGTGATAAATGCCTGTAGTCCCAGCCACTGAAGCCAGAG

GATCGATTGAACCAGGGAGATCATGGTCACAGTGAACTATGATTACGCCA

ACCTGGGTCACATAGCAAGACTCTGTTTCAAAAAAAAGGGGGGCGGGG

GACGGGTGGGTGCAGTGGCTCACATCTGTAACCCCAGCACTTTGGGAGGC

TGAGATGGGCAGATCACTTGAGGTCAGGAGTTCGAGACCAGCCTGGCCAA

CATGGTGAAACCCCATATCCATTAAAAATATTTAAAAATTAGCCAGACAT

GGTGGCACGCGTCTGTGGTCCTAGCTCCTCGGGAGGCTGAGGCAGGAGAA

TCGCTTGAACTCGGGAGGCAGAGGTTGTCATGAGCTGAGCTAACACCACG

GCACTTCAGCCTGGGTGACAGAATGAGACTCTGTGTCAAAAAAATAAAA

-continued

ATAAAAAATCTAAGGGCTCAGGAACCAGTTTGGACTTGATTTTGAATCCC

AGTTCATCCCCTTCCTAGCTGTATGACCTTGATTGTGTGCCTTAACCGCT

CTGTGACACAGTCTACCTGTCTGCAAAATGGGAAACATAATACCTGCCAT

CAGGATTGTTGAGGAGTAAATAAATGGAAATTGGTGGA

A representative sequence for Human
Deoxyribonuclease 2, Lysosomal (DNASE2A) protein
is provided by NCBI Reference Sequence: NP_001366.1
(SEQ ID NO: 2)

MIPLLLAALLCVPAGALTCYGDSGQPVDWFVVYKLPALRGSGEAAQRGLQ

YKYLDESSGGWRDGRALINSPEGAVGRSLQPLYRSNTSQLAFLLYNDQPP

QPSKAQDSSMRGHTKGVLLLDHDGGFWLVHSVPNFPPPASSAAYSWPHSA

CTYGQTLLCVSFPFAQFSKMGKQLTYTYPWVYNYQLEGIFAQEFPDLENV

VKGHHVSQEPWNSSITLTSQAGAVFQSFAKFSKFGDDLYSGWLAAALGTN

LQVQFWHKTVGILPSNCSDIWQVLNVNQIAFPGPAGPSFNSTEDHSKWCV

SPKGPWTCVGDMNRNQGEEQRGGGTLCAQLPALWKAFQPLVKNYQPCNGM

ARKPSRAYKI

It should be appreciated that other sequences corresponding to DNase enzymes are also compatible with aspects of the disclosure. One of ordinary skill in the art would be able to identify a given enzyme as a DNase enzyme, such as a DNASE2A enzyme, using routine methods in the art. For example, in some instances, DNase enzymes are annotated in databases commonly used in the art. One of ordinary skill in the art would also be able to identify an enzyme as being a DNase enzyme, such as a DNASE2A enzyme, based on domains within the sequence of the enzyme and/or based on homology to known DNase enzymes.

In some embodiments, a DNASE2A enzyme comprises a sequence corresponding to SEQ ID NOs 1 or 2. In some embodiments, a DNASE2A enzyme comprises a sequence that is at least 50%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NOs 1 or 2, including all values in between.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the invention described herein may be more fully understood, the following examples are set forth. The examples described in this application are offered to illustrate the systems and methods provided herein and are not to be construed in any way as limiting their scope.

Example 1: Extranuclear DNA Accumulates in Aged Cells and Contributes to Senescence and Inflammation Cellular replicative senescence was used as a model of aging. Effects of extranuclear DNA on inflammation and senescence were analyzed. In young and old human diploid fibroblasts (based on their replication age/population doubling (PD)), levels of extranuclear DNA, transcriptional profiles, and sensing of intrinsic DNA in modulating innate immune responses were compared. The investigation was then extended to clinical conditions of premature aging syndromes. A therapeutic approach of removing autonomous DNA to reduce inflammation in old cells was further tested. Finally, using mice deficient in DNASE2A, a role for autonomous DNA and the STING pathway in promoting senescence was observed. It was demonstrated that excess DNA contributes to inflammation and senescence, and components of the DNA sensing and degradation machinery were revealed that could be targeted for modulation of aging-related innate immune responses.

Results

Older Cells Accumulate DNA Outside the Nucleus

Figure 1B:
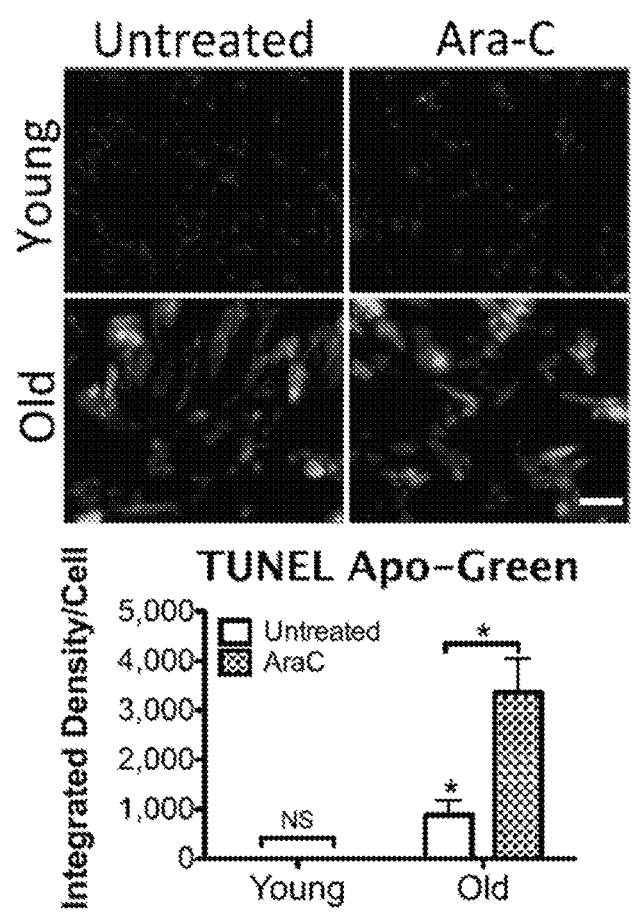
Figure 1C:
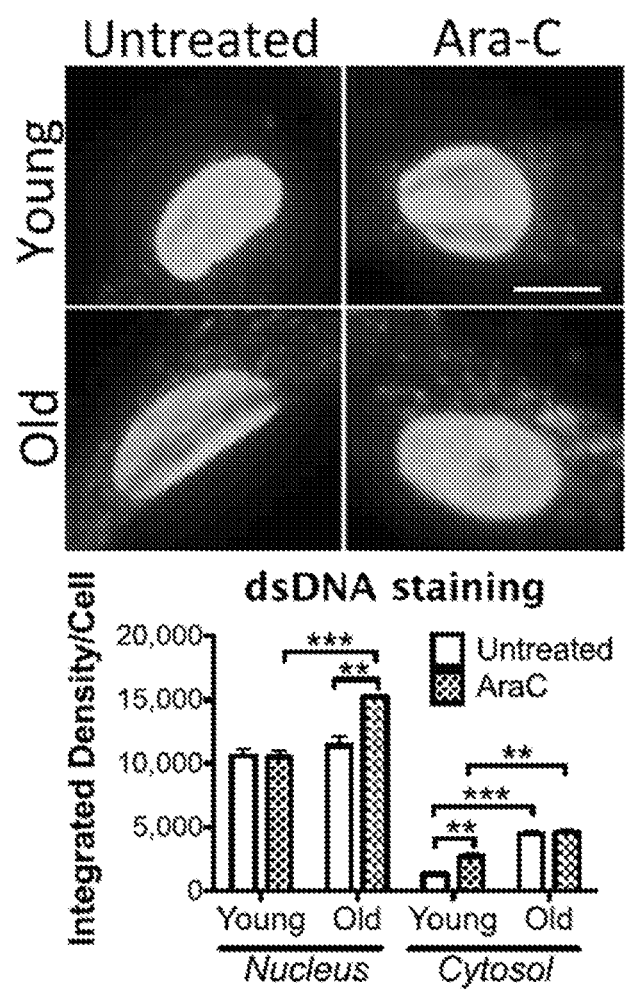
Figure 6A:
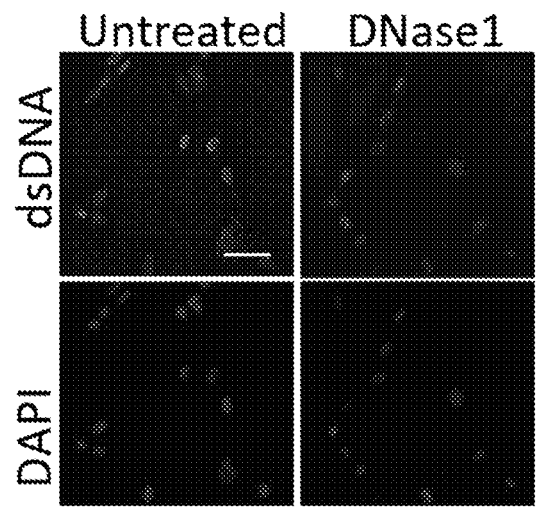
FIG. 6A shows old MRC5 cells post fixation and permeabilization, untreated or treated with DNase1 (500 U/ml) before staining with anti-dsDNA antibody. DAPI, counterstain; scale bar, 100 μm.

It was investigated whether cytosolic DNA would be more abundant in old compared to young cells. Using anti-double-stranded DNA (dsDNA) antibodies to detect DNA by IF, it was found that 16.8% of old WI38 cells (human lung fibroblasts at PD68-70, approaching senescence) exhibited extranuclear DNA in contrast to 2.6% in young cells (PD25-30). DNA was observed in the cytosol of old cells at much higher intensity than in young cells (FIG. 1A). These observations were confirmed in another fibroblast line, MRC5 (FIG. 1C, untreated). DNase1 digestion after fixation and permeabilization removed most of the cytosolic signals in old cells (FIG. 6A), thus verifying that the signal in the cytosol was due to DNA.

To confirm the presence of damaged DNA, TUNEL staining was used to label DNA nicks. Nicked DNA was strongly visible in old cells, prominently in the cytosol, but undetectable in young cells (FIG. 1B, untreated), and was more intense in old cells upon induction of DNA damage by the DNA damaging agent cytarabine/Ara-C, which causes DSBs (FIG. 1B, Ara-C-treated). Ara-C treatment also led to more extranuclear DNA in young cells (mostly speckles) and more nuclear DNA in old cells (FIG. 1C), suggesting there may be a saturation of DNA export to the cytosol.

Nuclear Origin and Export of Damaged DNA in Aging Cells

Figure 1D:
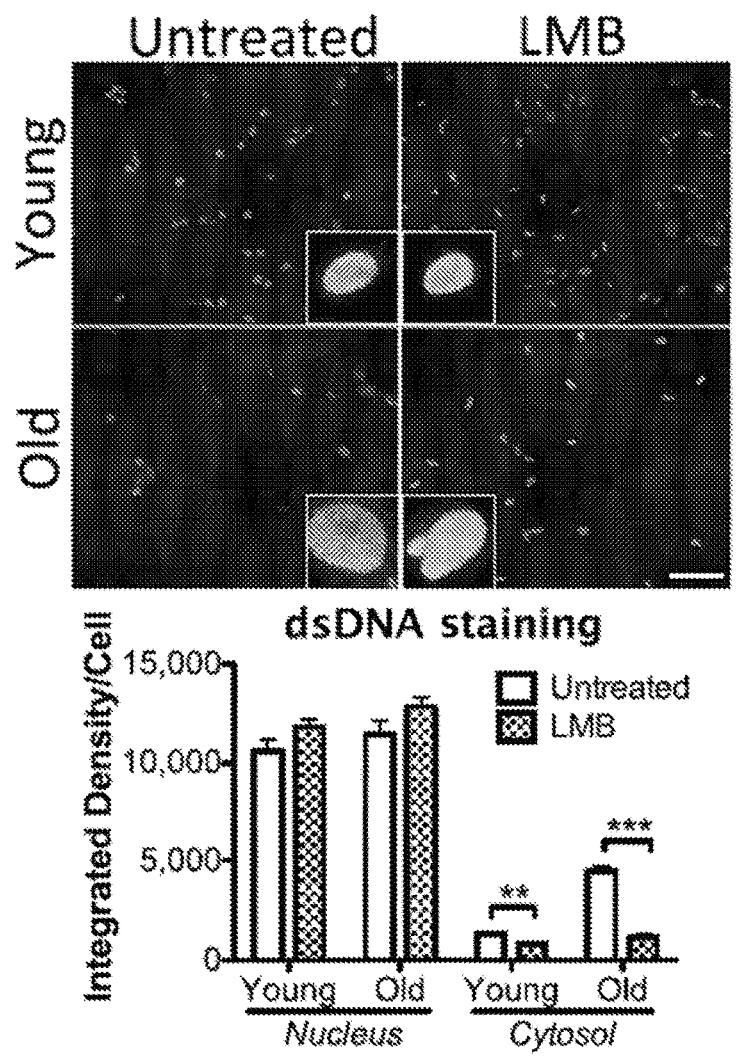
Figure 1E:
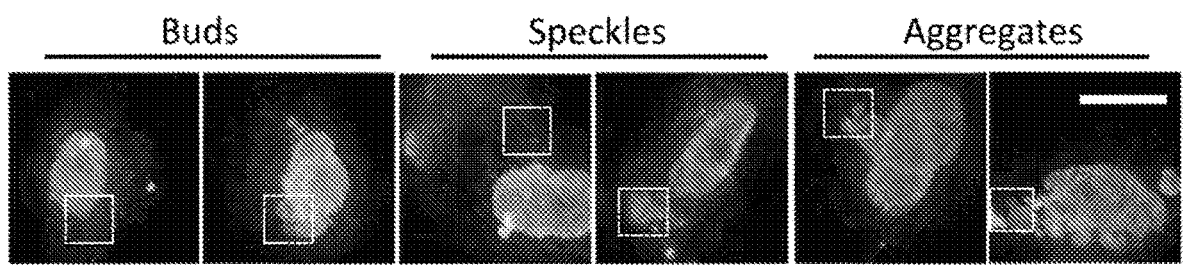
Figure 6B:
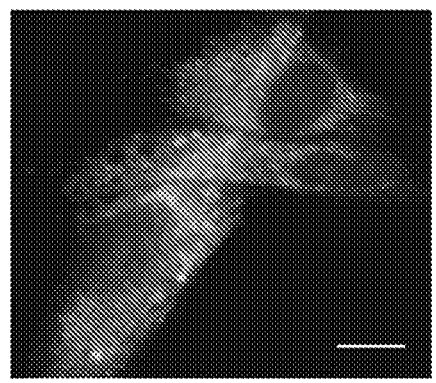
FIG. 6B shows old MCR5 cells live-stained with MitoTracker Orange (Molecular Probe M7510, 1 mM, 45 min, 37° C.), then fixed, permeabilized and stained with anti-dsDNA antibody. DAPI, counterstain; scale bar, 20 μm.

Excess mitochondrial DNA or mitochondria are not likely to be a source of the excess DNA in old cells since MitoTracker did not co-localize with excess DNA (FIG. 6B), though escape of DNA from mitochondria was not excluded. However, blocking of nuclear transport to the cytosol with leptomycin B (LMB) led to a dramatic reduction in cytosolic DNA in old cells (FIG. 1D), along with some increase in dsDNA staining in nuclei of LMB-treated cells (likely due to blockage of export). Dual staining of dsDNA and a nuclear envelope marker NUP98 (nucleoporin 98) revealed patterns of nuclear DNA egress in old cells in the form of buds at the nuclear perimeter and speckles and large aggregates in the cytosol (which are patterns observed in a prior study) (FIG. 1E). Distribution of NUP98 was uneven or disrupted and nuclear lobulations could be severe (FIG. 1E, right panel). Both results support the nuclear origin of extranuclear DNA in these (likely nonphagocytic) fibroblasts.

Figure 6C:
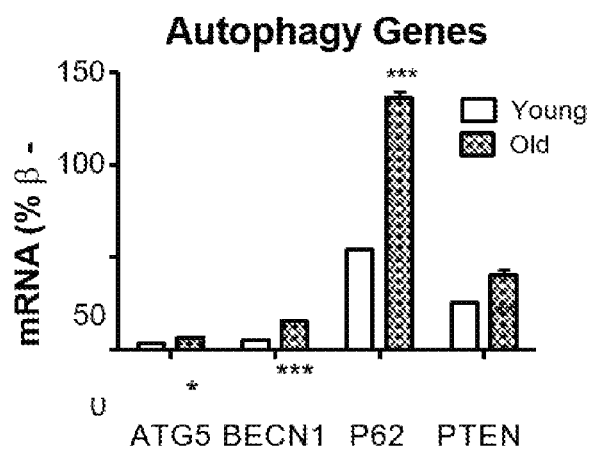
FIG. 6C shows transcript expression of autophagy genes in young and old MRC5 cells assessed by RT-qPCR.
Figure 6D:
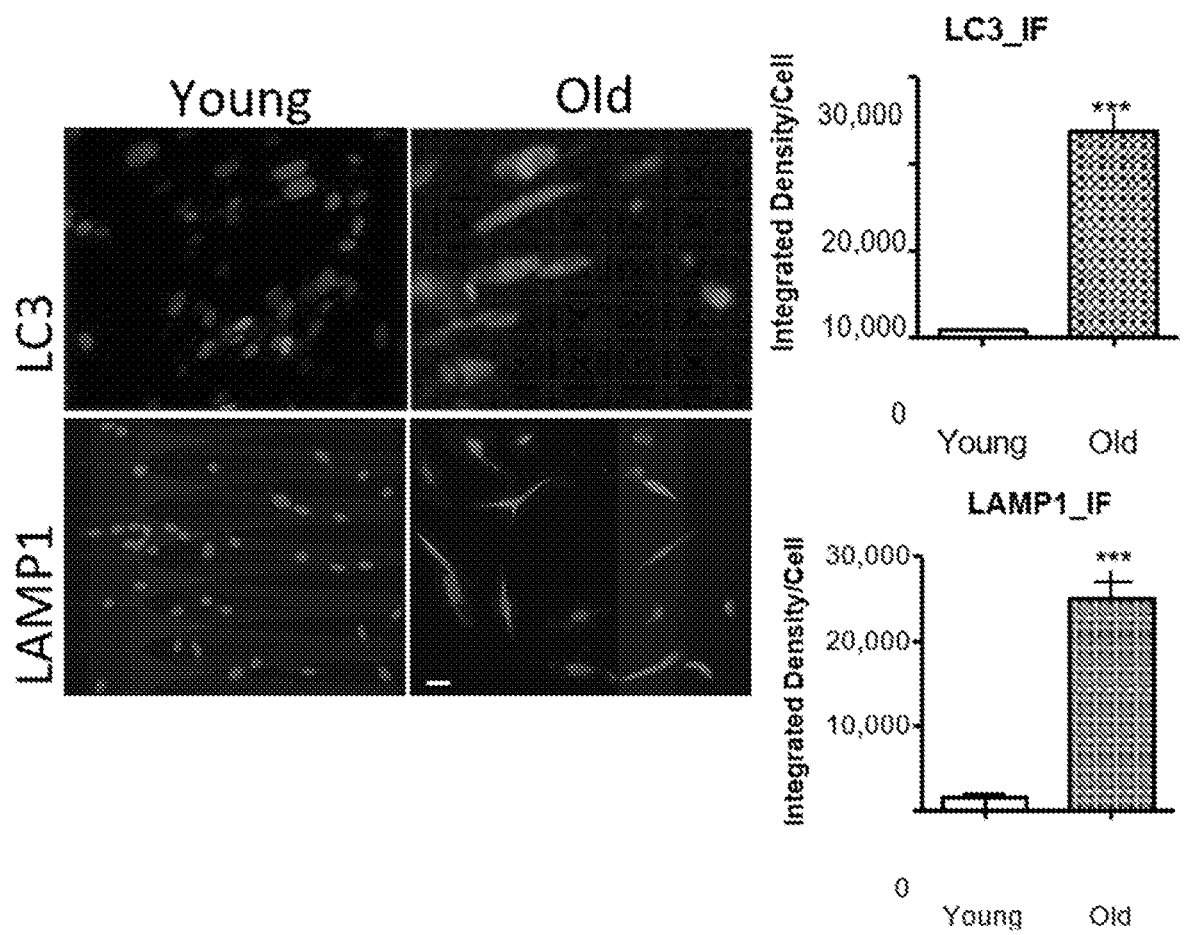
FIG. 6D shows IF staining and quantitation of anti-LC3 (top panel) and anti-LAMP1 (bottom panel) in young and old MRC5 cells, DAPI, counterstain. Quantitation based on 5 random fields of 10× images; scale bar, 20 μm.
Figure 6E:
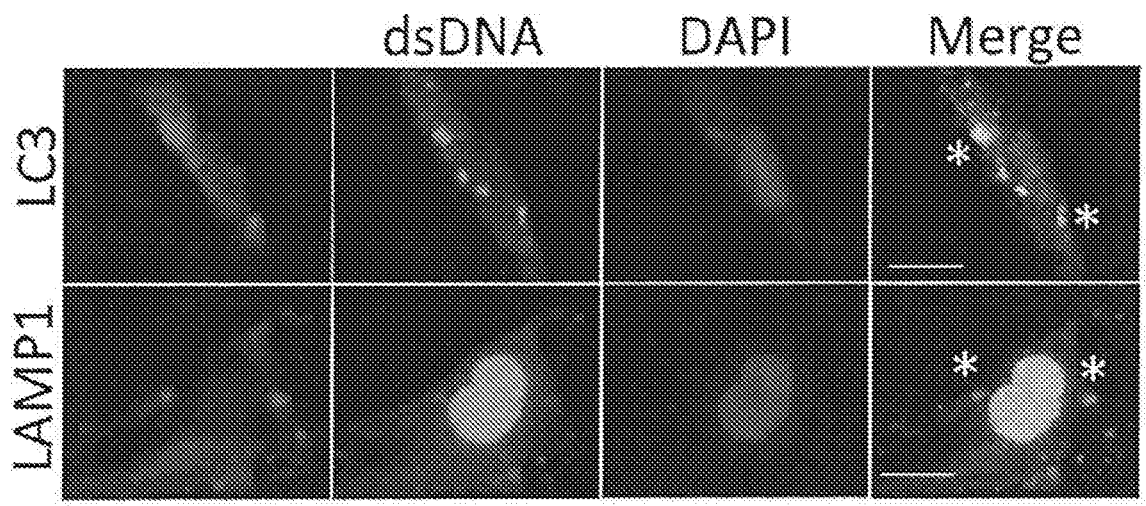
FIG. 6E shows representative two-color confocal images of anti-LC3 (top panel) and anti-LAMP1 (bottom panel) with PicoGreen (for dsDNA) in MRC5 old cells. Asterisks highlight signal co-localization areas; DAPI, counterstain; scale bar, 20 μm.
Figure 6F:
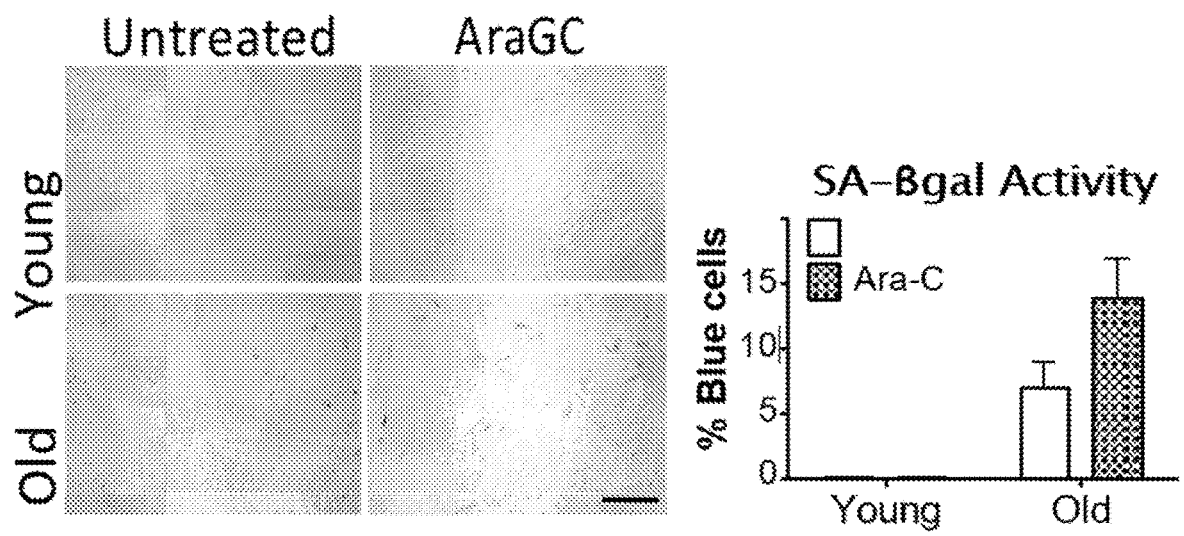
FIG. 6F shows SA-βgal activity and quantitation in young and old MRC5 cells, treated without or with 10 μM AraGC for 24 h. Scale bar, 50 μm.
Figure 6G:
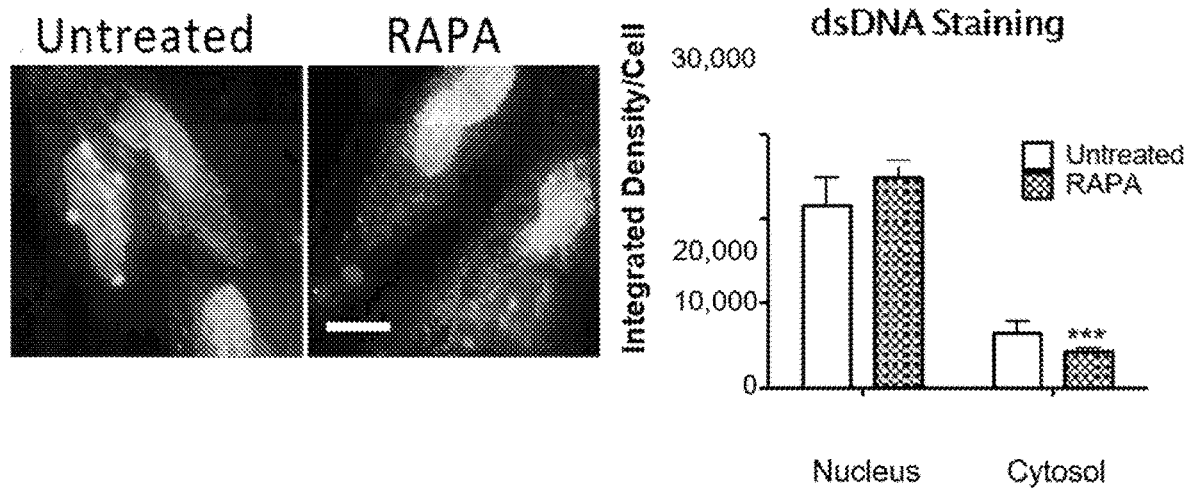
FIG. 6G shows IF staining and quantitation of anti-LC3 and anti-dsDNA in old MRC5 cells untreated or treated with rapamycin (RAPA, 100 nm, 24 h), DAPI, counterstain. Scale bar, 20 μm. Significance determined by t-test; p<0.05, *, p<0.01, , p<0.005, *, p<0.0001, ****.

An increased expression of autophagy genes was found in old cells compared with young cells, including ATG5, BECLIN1, and transcription regulators P62 and PTEN (FIG. 6C), and the protein products of autophagosome marker LC3 and lysosomal protein LAMP1 (FIG. 6D). Indeed, extranuclear DNA co-localized with LC3 and LAMP1 in old cells (FIG. 6E), representing association of the autophagosome-lysosomal pathway. The co-localization of DNA and LC3 is not consistent with an extracellular source of DNA, such as exosomes or apoptotic cells and debris. A high percentage of SA-β-gal+ cells was also found in aged MRC5 cells that further increased upon induced damaged by Ara-C, but none in young cells (FIG. 6F), consistent with this marker reflecting lysosomal abundance. Supporting these results, inducing autophagy in old cells with rapamycin reduced the amount of cytosolic DNA accumulation (FIG. 6G). It was concluded that cells of older replicative age have increased levels of extranuclear DNA fragments that are being transported from the nucleus and processed via autophagy.

Innate Immune Expression Profiles in Old Cells

Figure 2A:
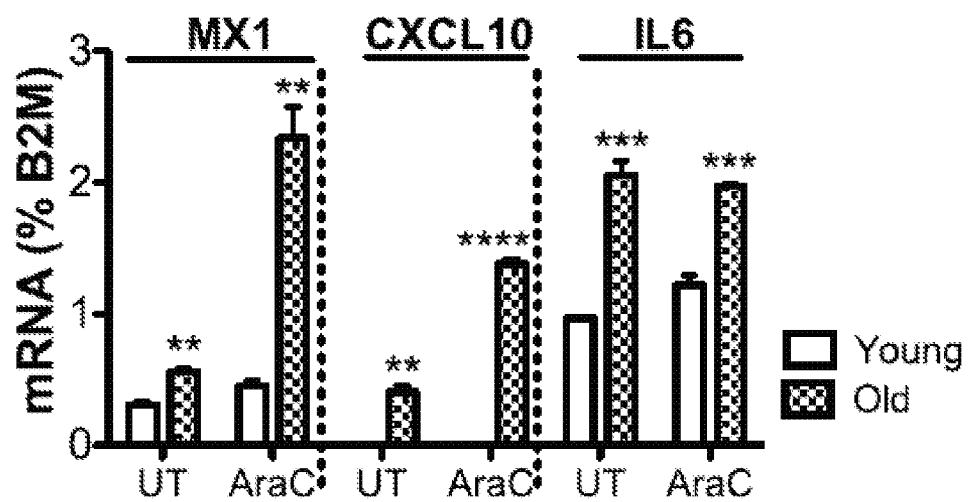
FIGS. 2A-2G provide data showing innate immune activation in old cells.
Figure 2B:
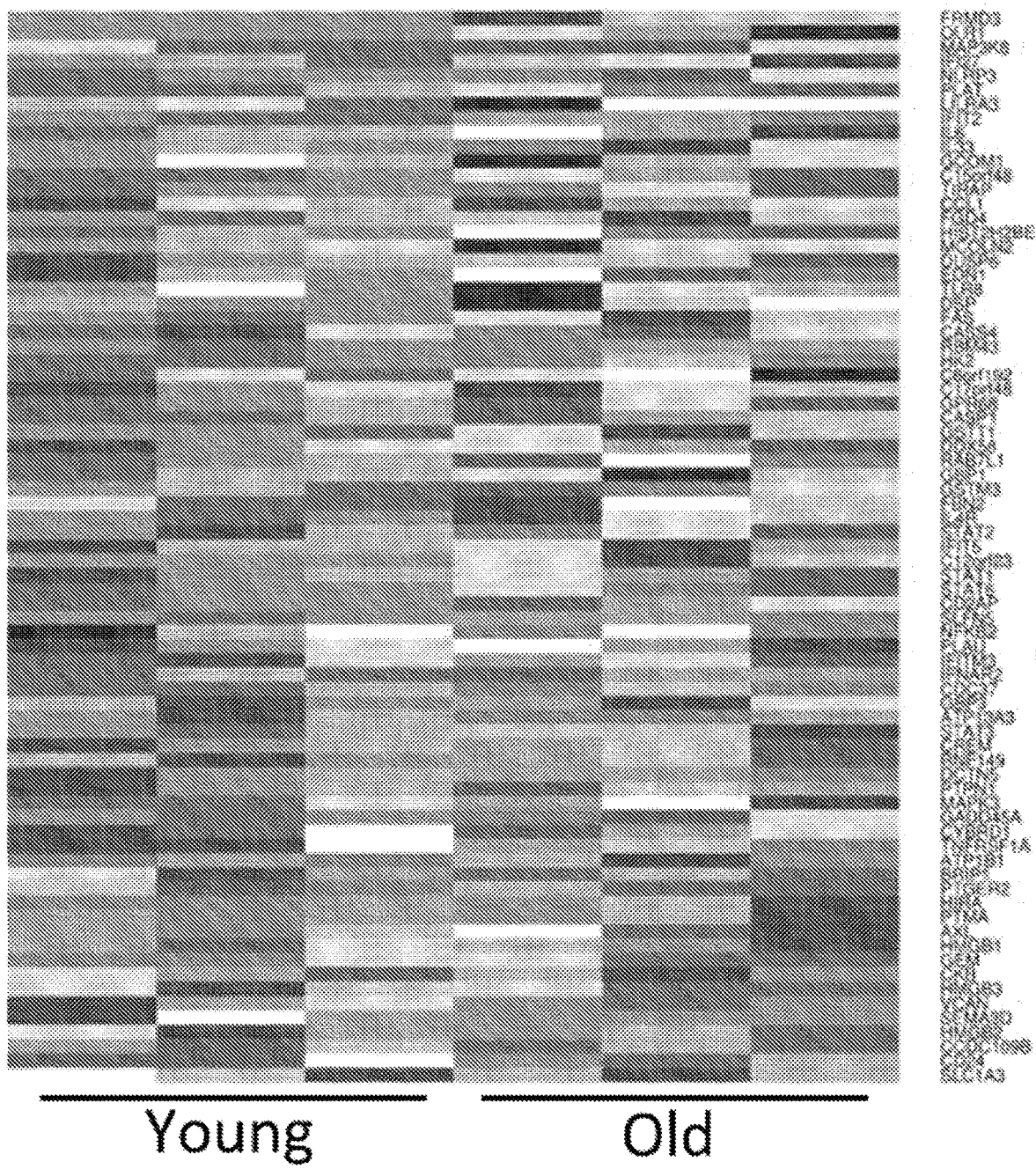
Figure 2C:
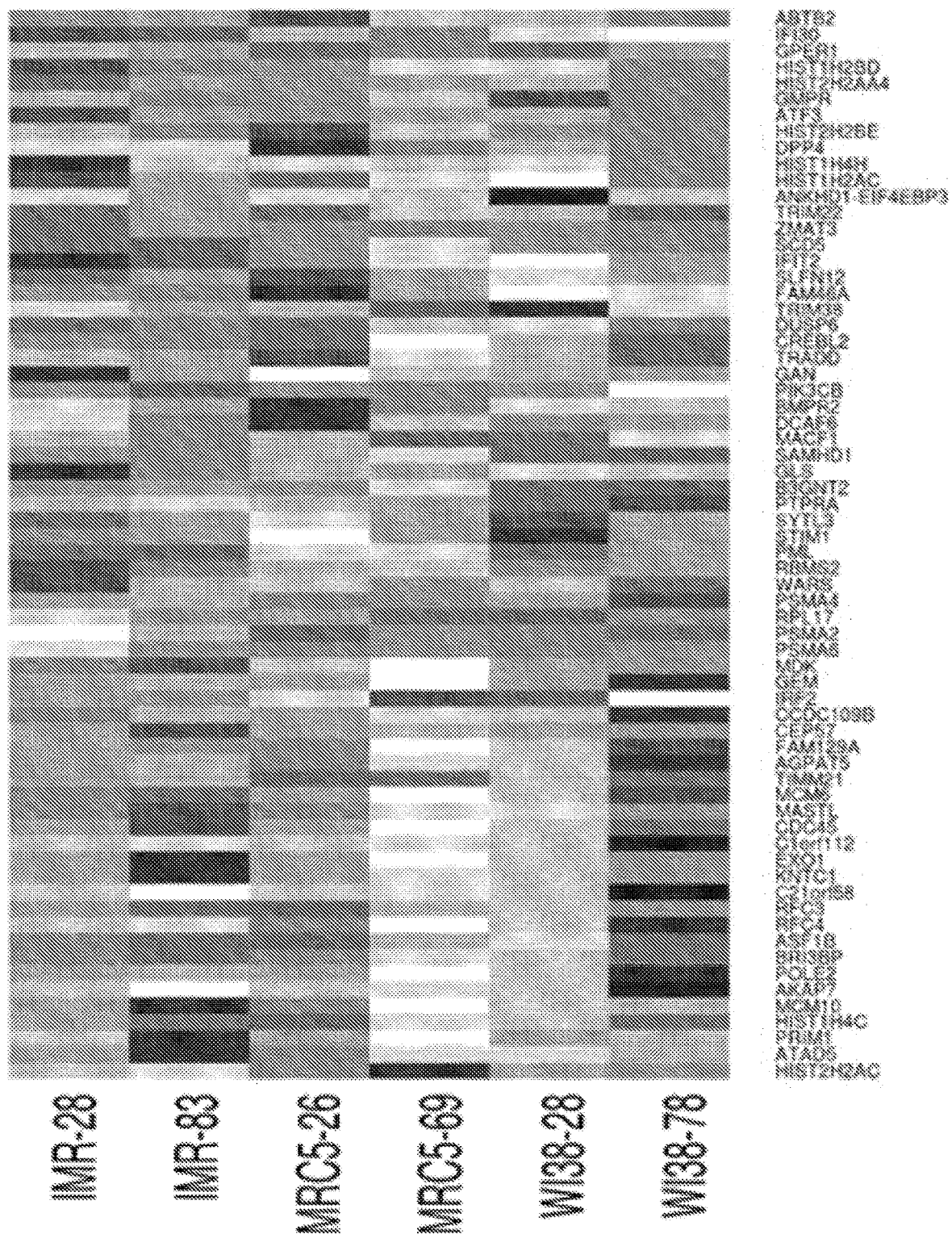
Figures 7C, 7D:
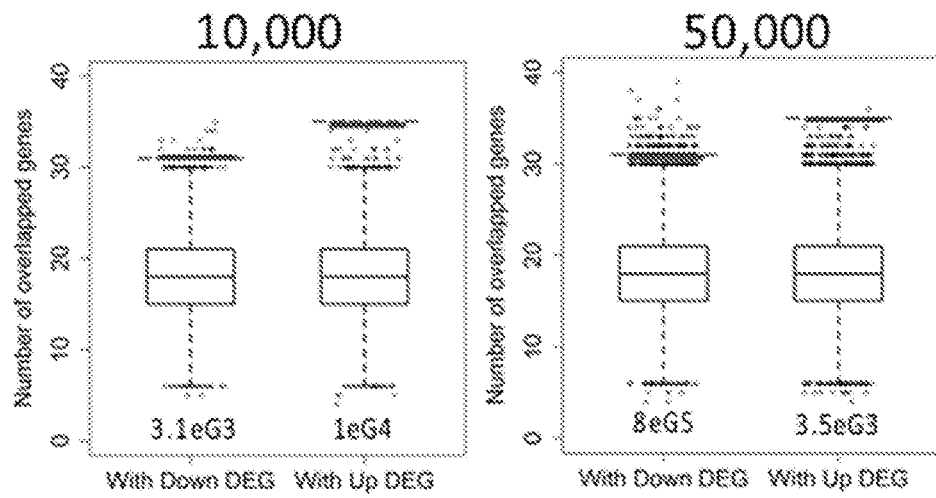
FIG. 7C shows a hypergeometric probability test for up-regulated overlapping genes in FIG. 7B.
FIG. 7D provides boxplots showing permutation test of overlapping genes in FIG. 7B by random sampling (lei=10,000, right=50,000 samples). Horizontal lines represent actual frequencies above predicted means in up- or down-regulated genes.

Accumulated extranuclear DNA can provoke an increased expression of type I IFN and inflammatory cytokines and genes via the STING pathway. Despite undetectable levels of IFN-α and IFN-β (and IFN-λ) transcripts, it was confirmed by RT-qPCR that there were higher basal levels of type I IFN-inducible and inflammatory genes MX1, CXCL10, and IL-6 in old MRC5 cells compared with young cells, which were further increased upon Ara-C treatment (FIG. 2A). This suggests stronger activation of immune responses and higher sensitivity to damage in old than in young cells. To focus on innate immune activation, transcripts of 413 innate and inflammation-related genes were measured using a custom human NanoString multiplex panel. 59 significantly upregulated genes were observed in old MRC5 cells (FIG. 2B), which overlapped with the type I IFN (e.g., IFIT2, IFIT5, IFNAR2, STAT1, STAT2) and IL-6-JAK-STAT3 (e.g., IL-6, STAT3, STAT6) pathways. Downregulated genes were also observed that included HMGB1, 2, and 3 (nonhistone nuclear proteins of the Alarmin family that trigger immune responses) (FIG. 7A, full gene list). To examine the aging transcriptome more broadly for essential innate immune components, RNA sequencing (RNA-seq) was performed of young and old cells from three common human diploid fibroblasts: IMR90 and WI38 together with MRC5. Differentially expressed genes (DEGs) were identified in old versus young cells: 683 upregulated and 698 downregulated DEGs. Using a curated set of 625 type I IFN-regulated genes in fibroblasts (Interferome v2.01; (Rusinova et al., 2013)), a significant overlap of 35 upregulated and 31 downregulated DEGs was found in old cells (FIG. 2C; FIG. 7B, gene list; FIG. 7C, significance p<0.0001 by hypergeometric test; FIG. 7D, actual>predicted frequencies by permutation test), with some heterogeneity across cell lines (FIG. 7E).

Figure 2D:
Figure 2E:

Gene Set Enrichment Analysis (GSEA) revealed that old cells, across all three cell lines, were enriched in genes that are part of the "IFN-α response," "IL-6-JAK-STAT3 signaling," "inflammatory response," and "TNF-α signaling" (FIG. 2D; FIG. 7F, other hallmarks with False Discovery Rate FDR<0.25)—each Hallmark gene set is minimally redundant to represent the denoted pathway. IFN response and IL-6 represent the two arms of inflammatory responses downstream of DNA sensing (TBK1-IRF3 axis and IKK-NF-κB axis, respectively (Li & Chen, 2018)). Using only 54 STING-interacting factors (FIG. 7G, pathwaycommons.org), unsupervised hierarchical clustering separated young and old cells, with 15% of these genes significantly upregulated in old cells including IL1A, F3, IKBKB, TSLP, SAMHD1, DTX4, DDX41, and IL4R (FIG. 2E).

Role of Autophagy and Sensing in Old Cell Innate Immune Activation

Figure 2F:
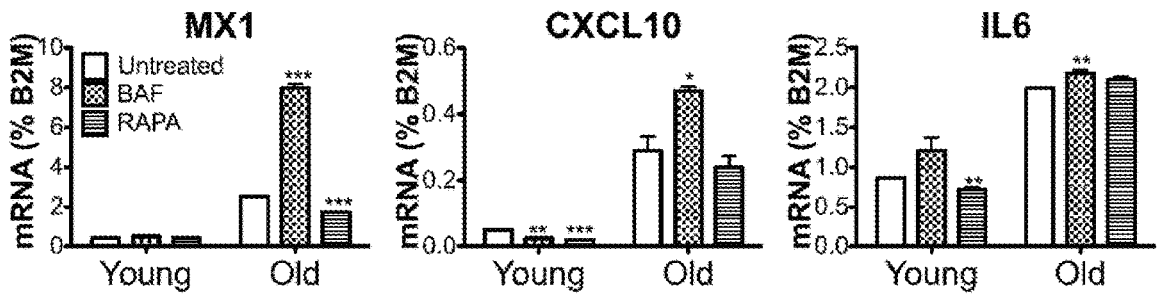
Figure 2G:
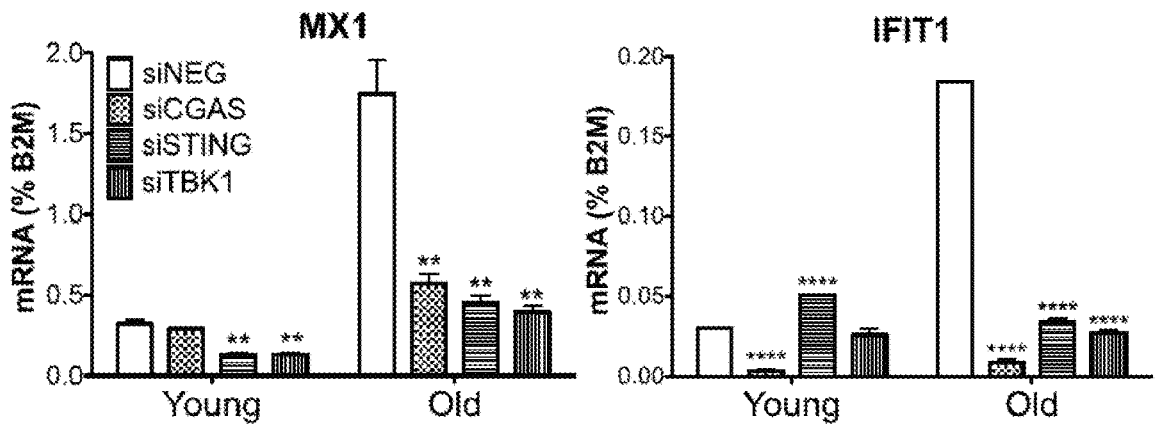
Figure 7H:
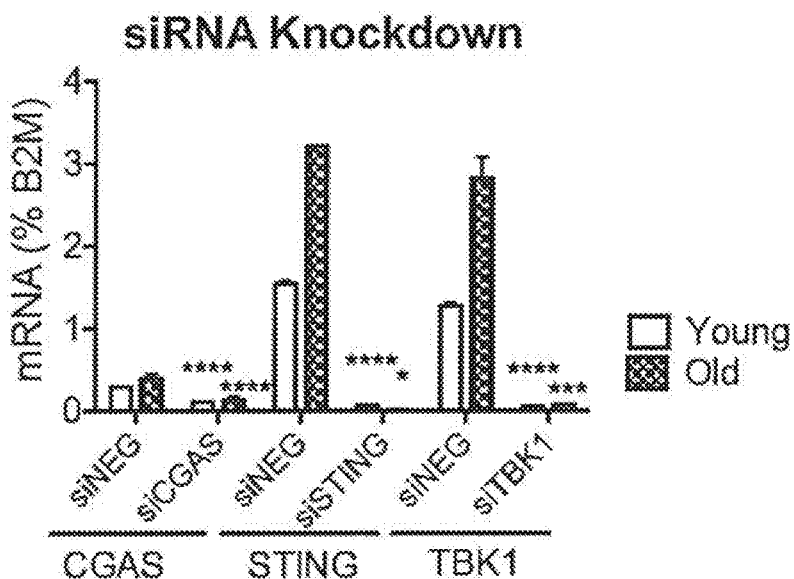
FIG. 7H shows an assessment of siRNA knockdown efficiency for cGAS, STING and TBK1 in young and old MRC5 cells by RT-qPCR.
Figure 7I:
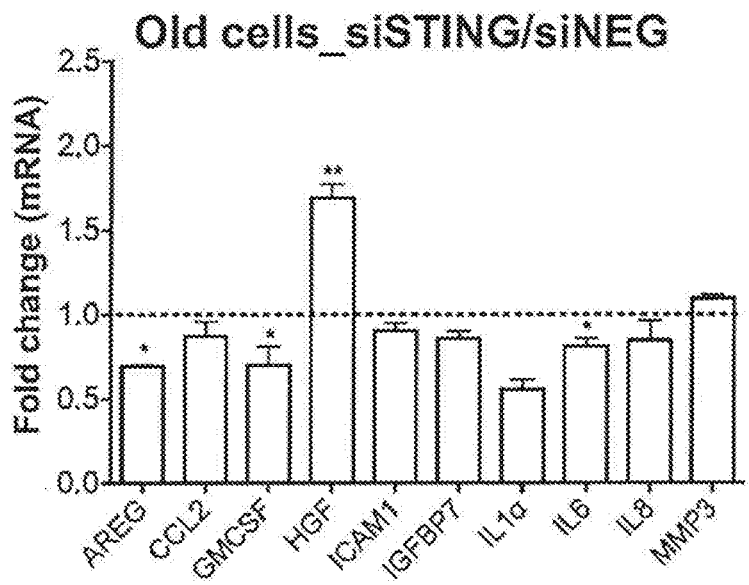
FIG. 7I shows fold change mRNA expression (siSTING/siNEG) of SASP factors in oldMRC5 cells by RT-qPCR. Significance determined by t-test; p<0.05, *, p<0.01, , p<0.005, *, p<0.0001, ****; if not indicated.

Consistent with the original model of extranuclear DNA being processed by autophagy and stimulating the STING pathway, it was found that old cells treated with bafilomycin A1 (which blocks lysosomal fusion to autophagosomes) showed increased levels of MX1 and CXCL10, while cells treated with rapamycin (that stimulates autophagy) reduced MX1 expression (FIG. 2F). This is consistent with the finding that LC3 and LAMP1 are associated with exported DNA in aged cells (Figure E and G). Furthermore, when genes in the cGAS-STING-TBK1 axis were knocked down by siRNAs (FIG. 7H, knockdown efficiency), expression of IFNI-inducible MX1 and IFIT1 (FIG. 2G) and 3 of 10 detectable SASP factors (FIG. 7I) was reduced. Overall, these results indicate a heightened innate immune response in old cells, which is cGAS/STING-dependent and is affected by autophagy and lysosomal activity.

Figure 3A:
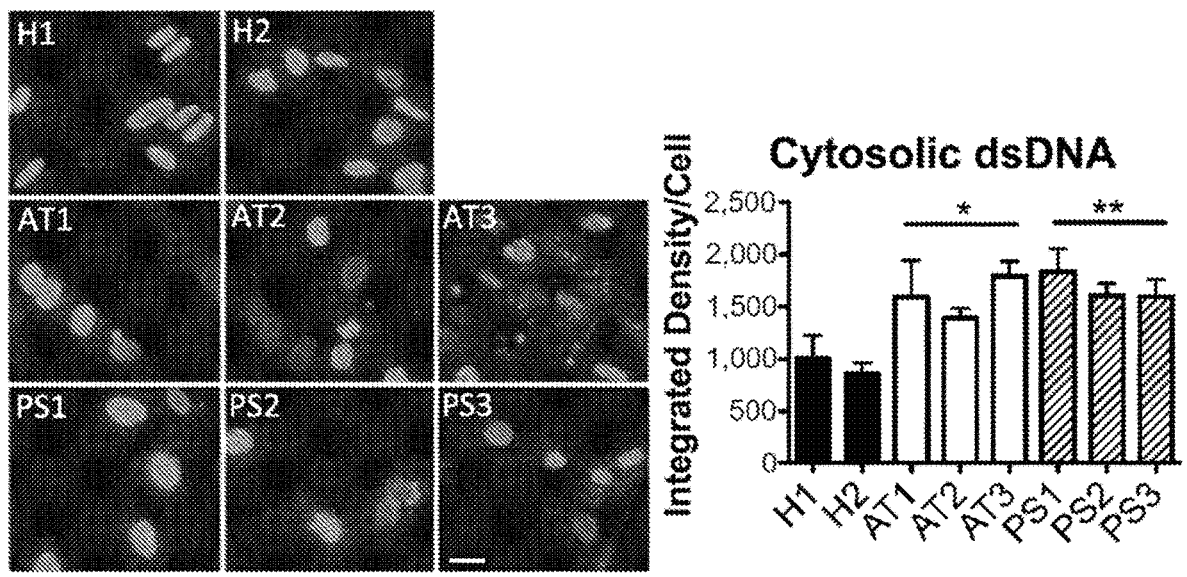
Figure 3C:
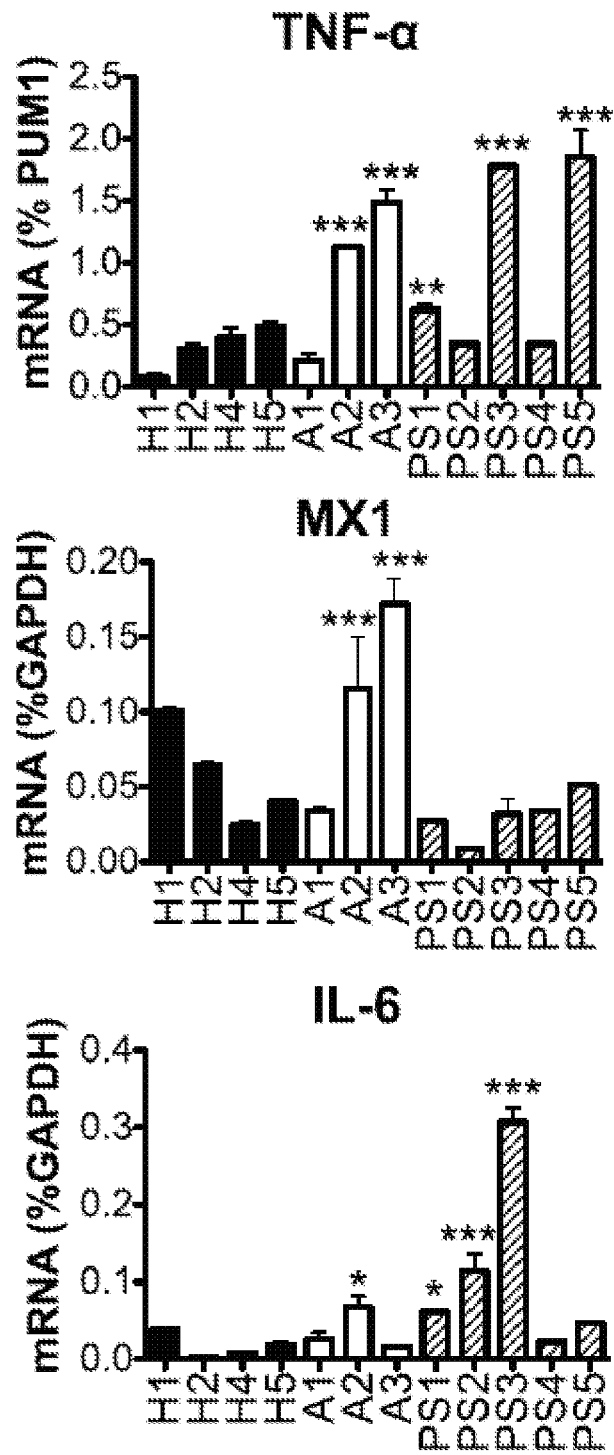
Figure 8A:
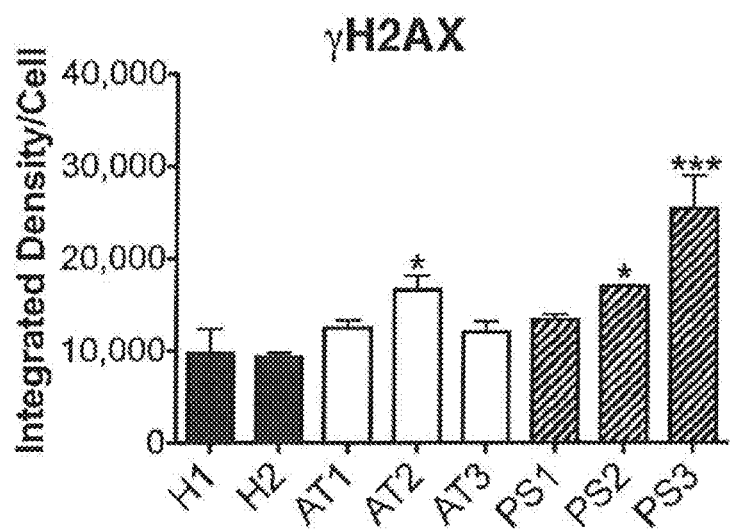
FIG. 8A shows quantitation of γGH2AX IF staining in healthy (H), ataxia (AT) and progeria (PS) skin fibroblasts. Numbers represent different fibroblasts of each phenotype. Significance by 1-way ANOVA between groups, p<0.0001; and that of AT2, PS2 and PS3 vs. H1 or H2 by Tukey's test as indicated.

Cytosolic DNA Accumulates and Inflammatory Pathways are Activated in Cells from Premature Aging Syndromes It is possible that cytosolic DNA is a cell-intrinsic inflammatory ligand that might extend to cells from humans with aging diseases. The focus was on two genetic disorders, ataxia telangiectasia (AT), a severe neurodegenerative syndrome caused by gene defects in ATM (ataxia telangiectasia mutated) which is essential for DSB repair, and Hutchinson-Gilford progeria (HGPS or PS), which exhibits premature aging symptoms due to a mutation in LAMIN A (LMNA) that maintains nuclear architecture. Mutations of either disease gene could lead to excess cytosolic DNA as a result of increased DNA damage (in AT) or leaky nuclear envelope (in PS). Prominent extranuclear dsDNA accumulation was found in the form of nuclear buds, speckles, and large fragments by anti-dsDNA IF staining in different AT and PS skin fibroblasts of patients but not healthy donors (FIG. 3A). DNA accumulation in both conditions also correlated with increased DSBs marked by γ-H2AX (FIG. 8A). The innate immune profiles of the healthy and disease fibroblasts (H1, 4, 5; AT1-3; PS1-5) were then examined by RNA-seq. GSEA showed AT having 5 of 11 enriched gene sets in immune processes, including IFN-α, TNF-α, and IL-6 responses, while PS showed increased IL-6 signaling as the top enriched gene set (FIG. 3B). By RT-qPCR, higher expression of TNF-α, an important cytokine in inflammation (Fagiolo et al., 1993; Roubenoff et al., 2003), was observed in cells from both diseases and it was confirmed that AT and PS cells differentially upregulated genes downstream of the two innate immune arms (MX1 for the TBK1-IRF3 arm, and IL-6 for IKK-NF-κB) (FIG. 3C, ****p<0.0001, 1-way ANOVA), consistent with GSEA. The increased innate immune responses are suggestive of activation of DNA sensing as a result of accumulated cytosolic DNA.

STING-Mediated Induction of Inflammation and p16 in AT and PS Cells

Figure 3D:
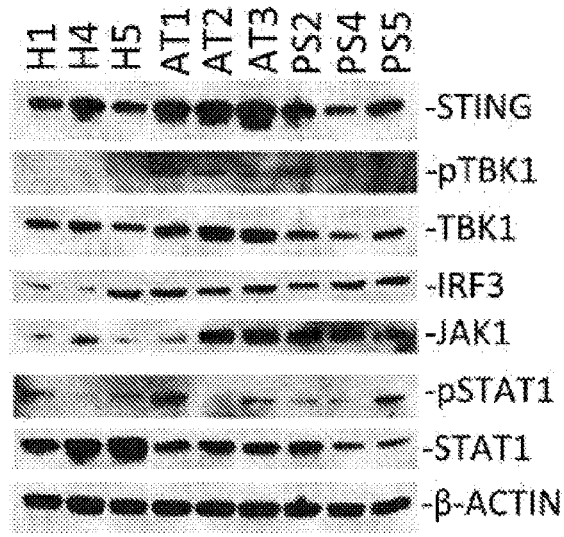
Figure 3E:
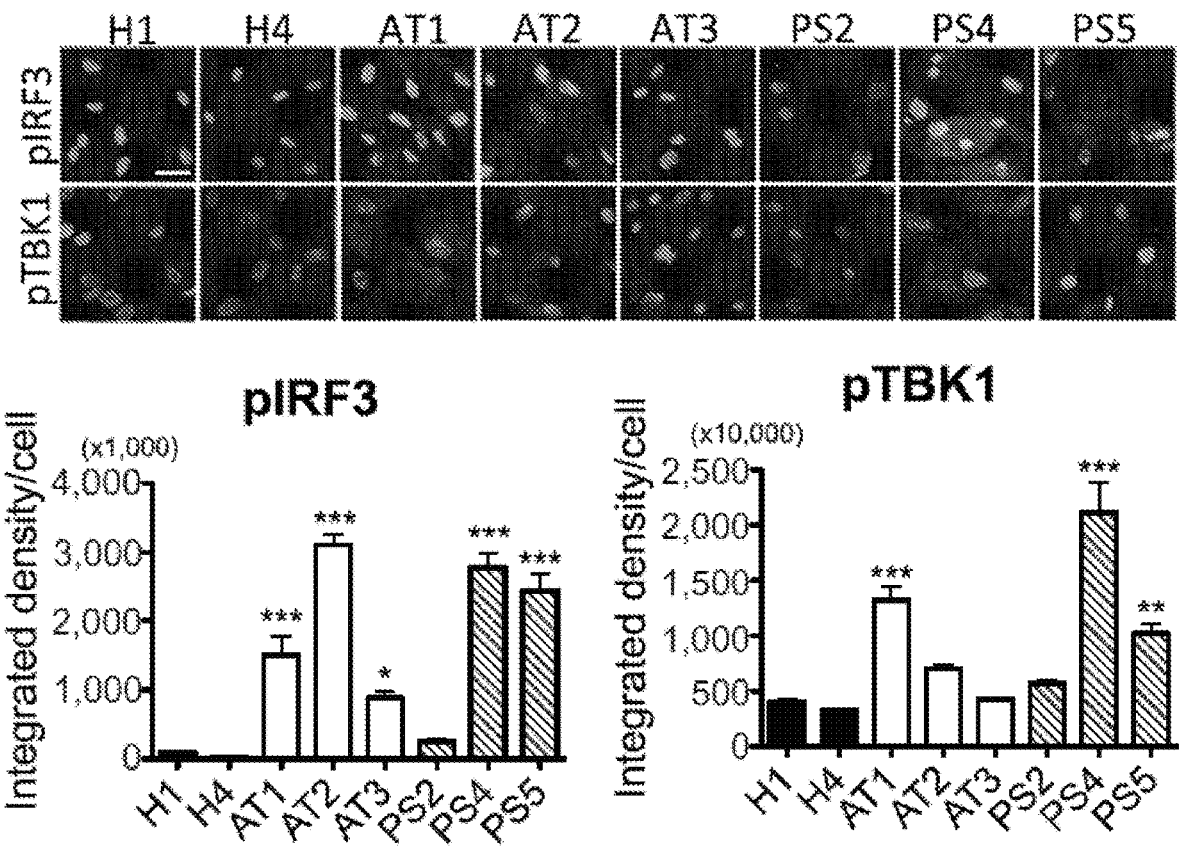
Figure 3F:
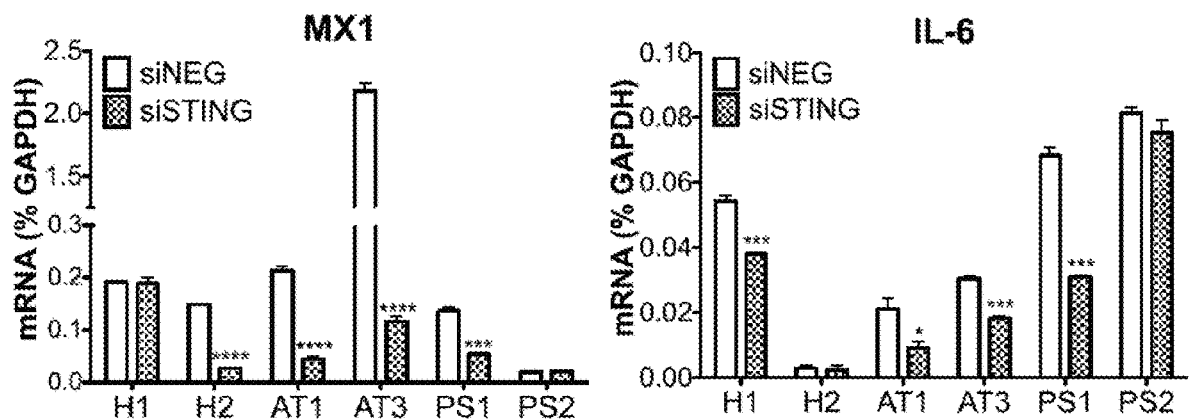
Figure 3G:
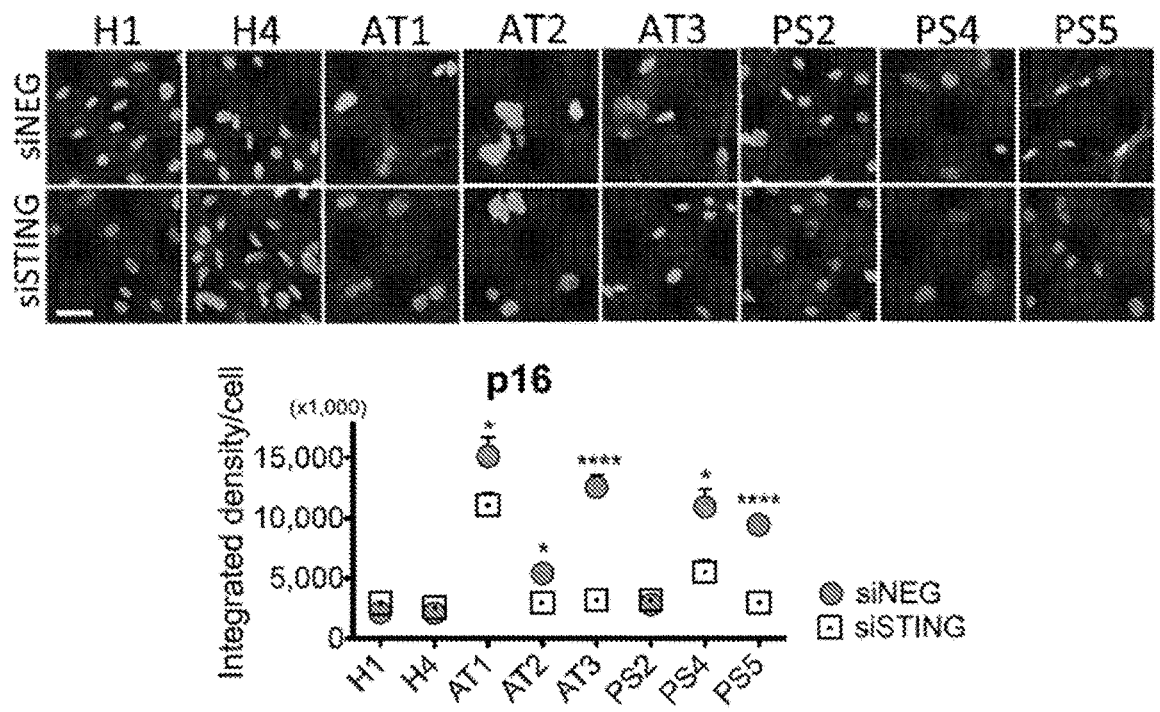
Figure 8B:
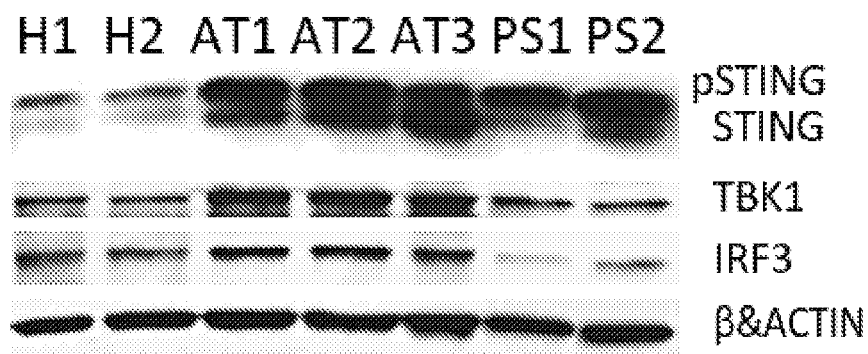
FIG. 8B provides an immunoblot showing DNA sensing mediators in H, AT and PS cells. Double bands in total STING are visible in disease cells. β-ACTIN was used as a loading control.
Figure 8C:
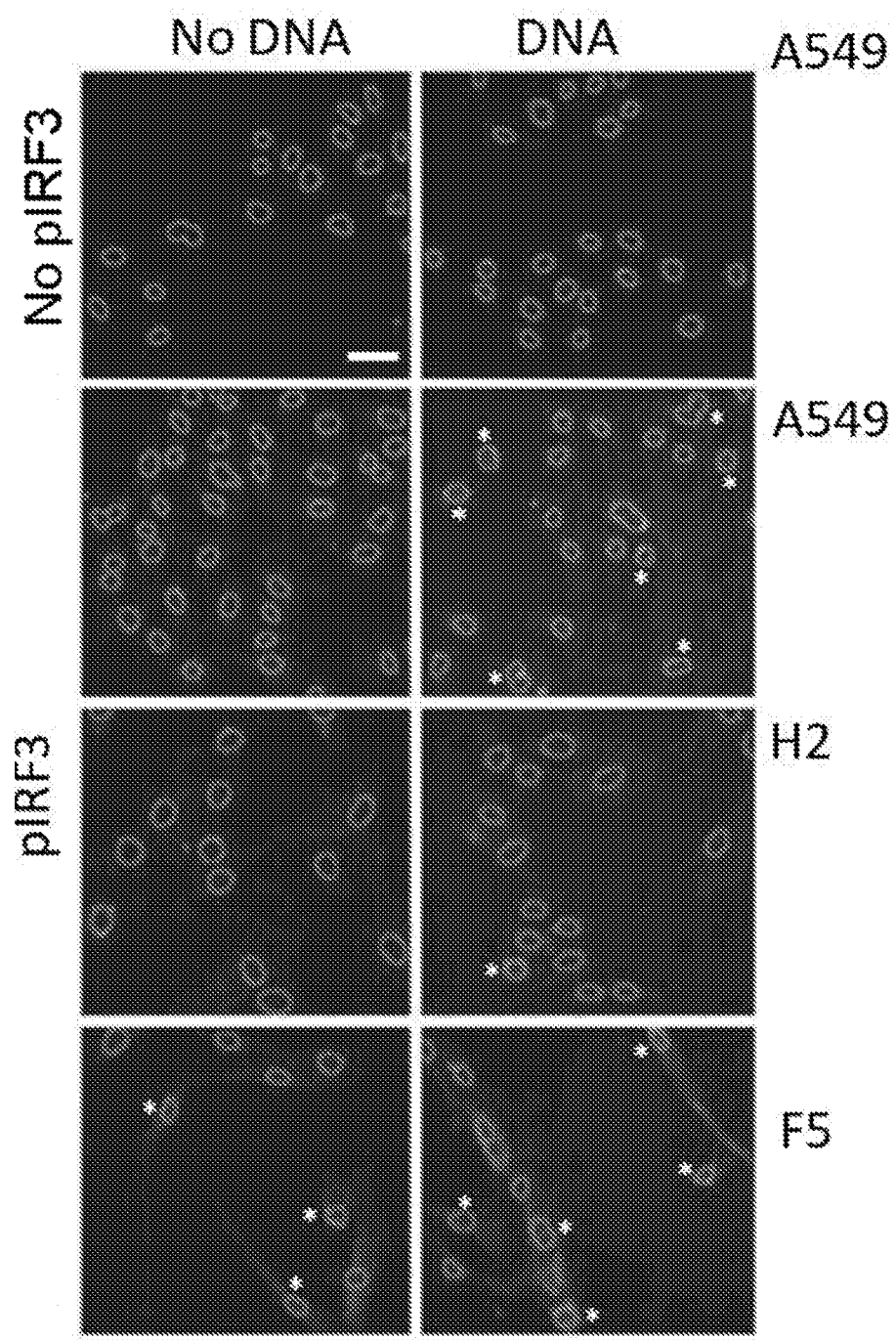
FIG. 8C shows A549 cells (human epithelial) and human fibroblasts from parents transfected with or without GAPDH DNA generated by PCR or ISD (interferon stimulatory DNA) fragments respectively (both 4 μg/ml, 4 h), using TransIT-LT1 transfection reagent (Mirus Bio, TransIT:DNA=3:1). Top panel shows background staining with secondary anti-rabbit antibody (AF568, red) alone. Light grey nuclear boundaries are based on DAPI staining. Asterisks highlight nuclear pIRF3 staining; scale bar, 20 μm.
Figure 8D:
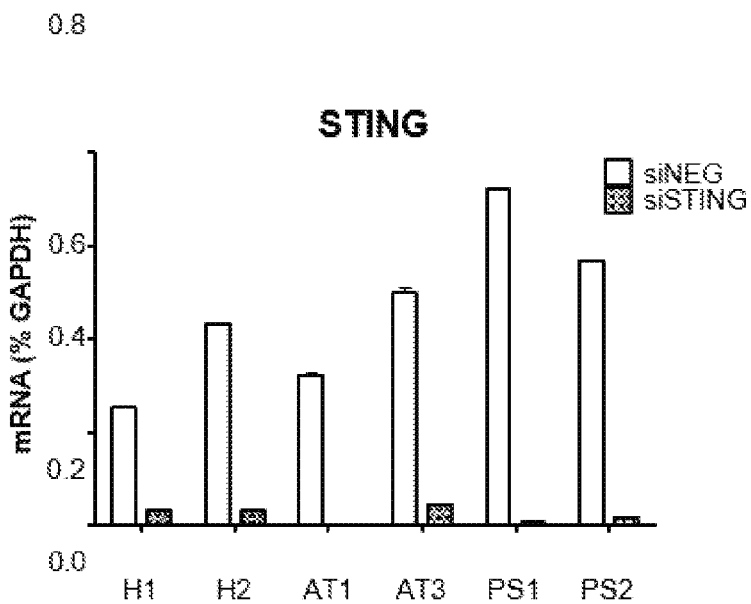
FIG. 8D shows STING knockdown efficiency in H, AT and PS cells validated by RT-qPCR.

Indeed, dramatic elevation of total STING abundance and concomitant increase in its downstream effectors pTBK1, TBK1, IRF3, and JAK1 (and pSTAT1 in some cells) was observed by immunoblotting in AT cells (FIG. 3D). An increase in STING was also found in some PS cells (FIG. 8B, additional PS cells). Phospho-IRF3 was not detected by immunoblotting, but could be visualized by IF staining. Nuclear pIRF3 staining upon DNA stimulation was consistent with known pIRF3 responses (FIG. 8C). In disease cells (AT1, AT2, AT3, PS4, and PS5), cytosolic and nuclear patterns of pIRF3 distribution were observed (FIG. 3E). A previous study reported similar pIRF3-containing signaling complexes accumulating in enlarged juxtanuclear recycling endosomes (Gorbea, Rechsteiner, Vallejo, & Bowles, 2013). Elevated levels of pIRF3 in disease cells were associated with an increase in pTBK1 IF signals (FIG. 3E, **p<0.0001 for both pIRF3 and pTBK1, 1-way ANOVA). When STING was knocked down by transfected siRNAs (FIG. 8D, knockdown efficiency), expression of MX1 and IL-6 was abrogated in AT cells (which also had higher STING protein levels), but the effect in PS cells was more variable (FIG. 3F). To further test if DNA sensing is causal in the senescent phenotype of disease cells, STING was knocked down and significant reduction of the senescence marker p16 was found in all AT and PS cells tested, except PS2 (FIG. 3G). Basal levels of p16 in AT1, AT2, AT3, PS4, and PS5 were all significantly higher than those in healthy controls (*p<0.005, Tukey's test). These results support a role for the STING pathway in inducing genes involved in inflammation and senescence in aging diseases with accumulated DNA.

DNA Burden Impacts Age-Related Inflammation

Figure 4A:
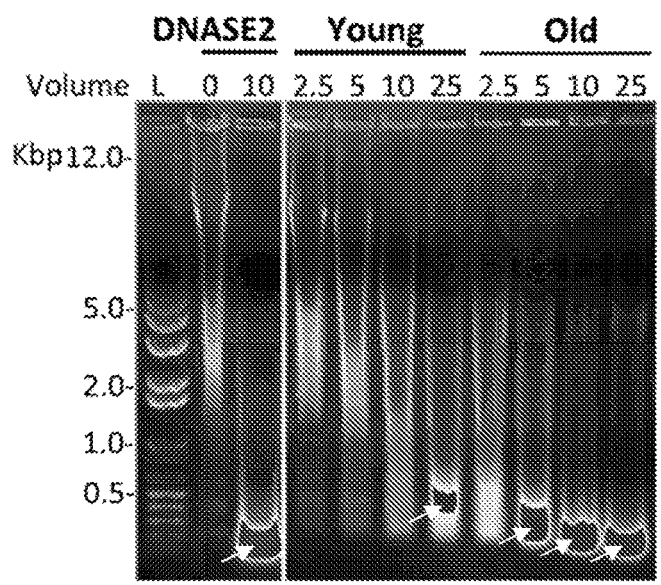
Figure 4B:
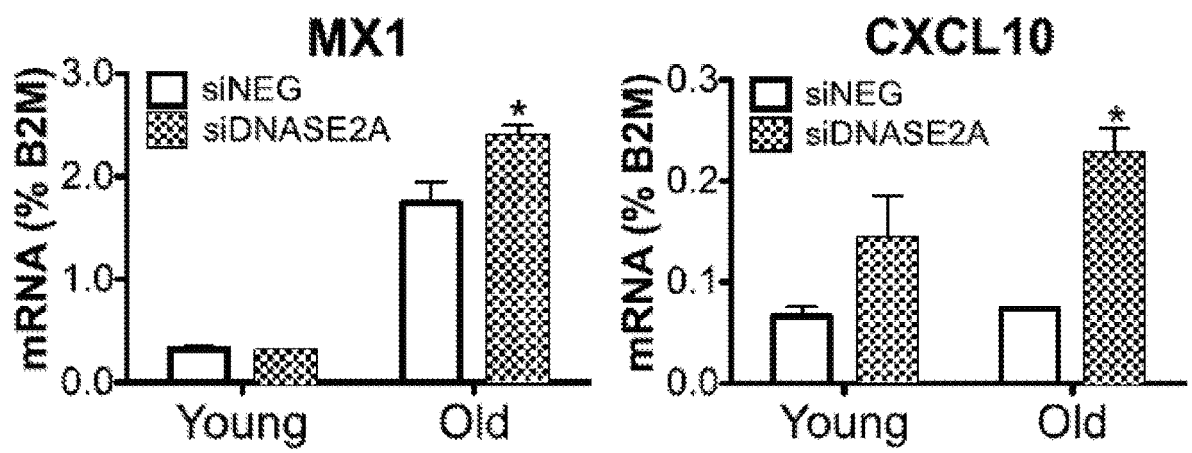
Figure 4E:
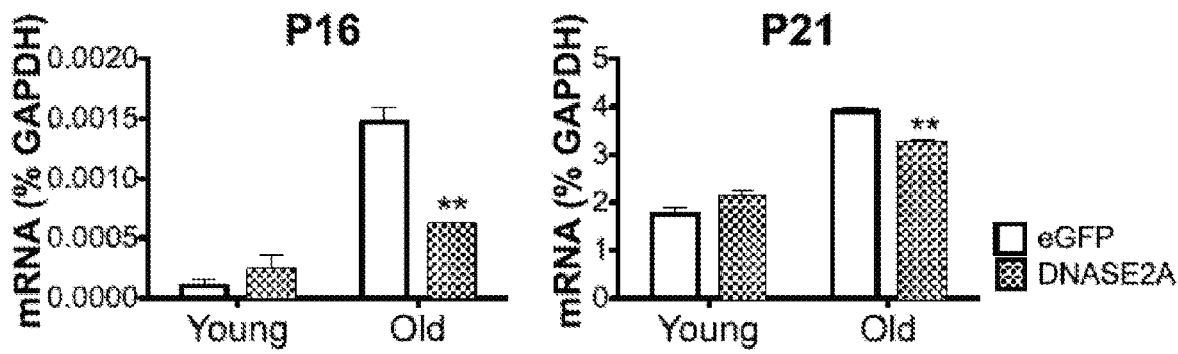
Figure 9A:
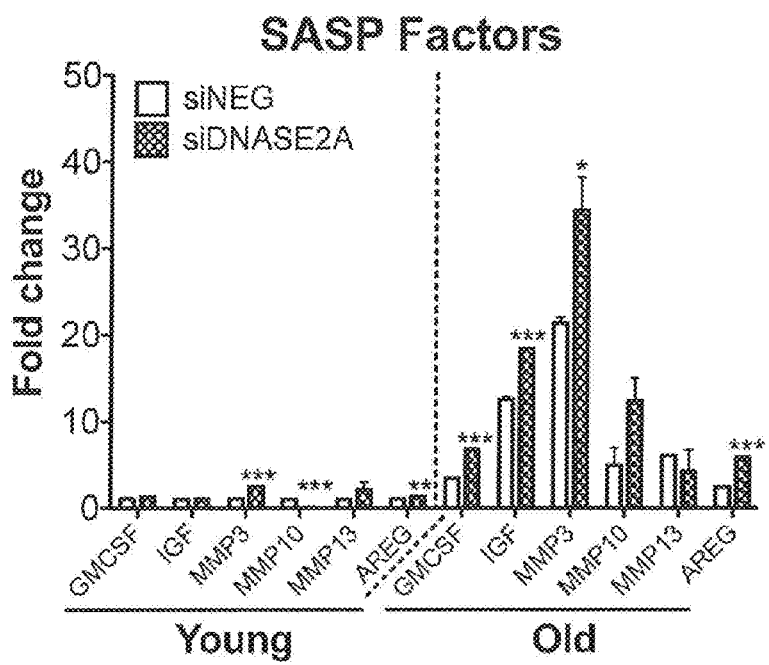
FIG. 9A shows fold change (siDNASE2A/siNEG) of transcript expression of SASP factors in young and old MRC5 cells with DNASE2A knocked down by transfected siRNAs; siNEG, non-targeting control. Expression values assessed by RT-qPCR, significance relative to siNEG values.
Figure 9B:
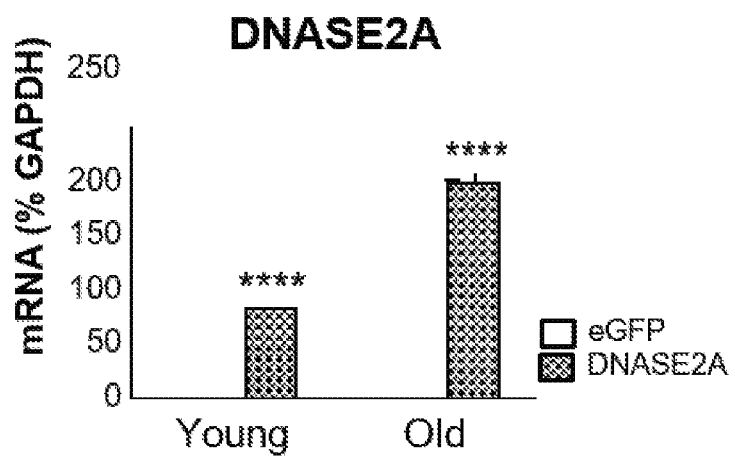
FIG. 9B shows assessment of human DNASE2A expression in young and old MRC5 cells after transduction with DNASE2A ORF or control eGFP by RT-qPCR. Significance is based on expression in eGFP controls. DNASE2A levels in eGFP controls was readily detectable but barely visible in scale shown. Significance by t-test, *, p<0.05; , p<0.01; *, p<0.005; ****, p<0.001.

On a per cell basis, lysates from old cells showed a stronger capacity to degrade dsDNA than young cells, reflecting an elevated clearance of excess DNA by lysosomal DNASE2A (FIG. 4A). It was reasoned that increased DNA degradation might restore the younger cell phenotype or even revert the process of senescence. As expected, knocking down DNASE2A in MRC5 cells worsened inflammation in old cells, resulting in increased MX1 and CXCL10 (FIG. 4B), and heightened SASP factors such as GM-CSF, IGFBP7, and MMP3 (FIG. 9A). The DNA degrading enzyme was then overexpressed in cells by a constitutive lentiviral vector encoding the DNASE2A open reading frame (ORF). DNASE2A transduced in old MRC5 cells (FIG. 9B, expression by RT-qPCR) significantly reduced cytosolic and even nuclear DNA (FIG. 4C), SA-β-gal activity (FIG. 4D), and expression of MX1 and genes controlling cell cycle (p16, p21) (FIG. 4E). Cell growth was unable to be revived in old cells by increasing DNA degradation alone in these specific experiments. It was concluded that excess DNA strongly impacts the senescence response in vitro, and that its removal can alleviate inflammation in old cells.

Dnase2a Deficiency Recapitulates Cellular Senescence

Figure 5A:
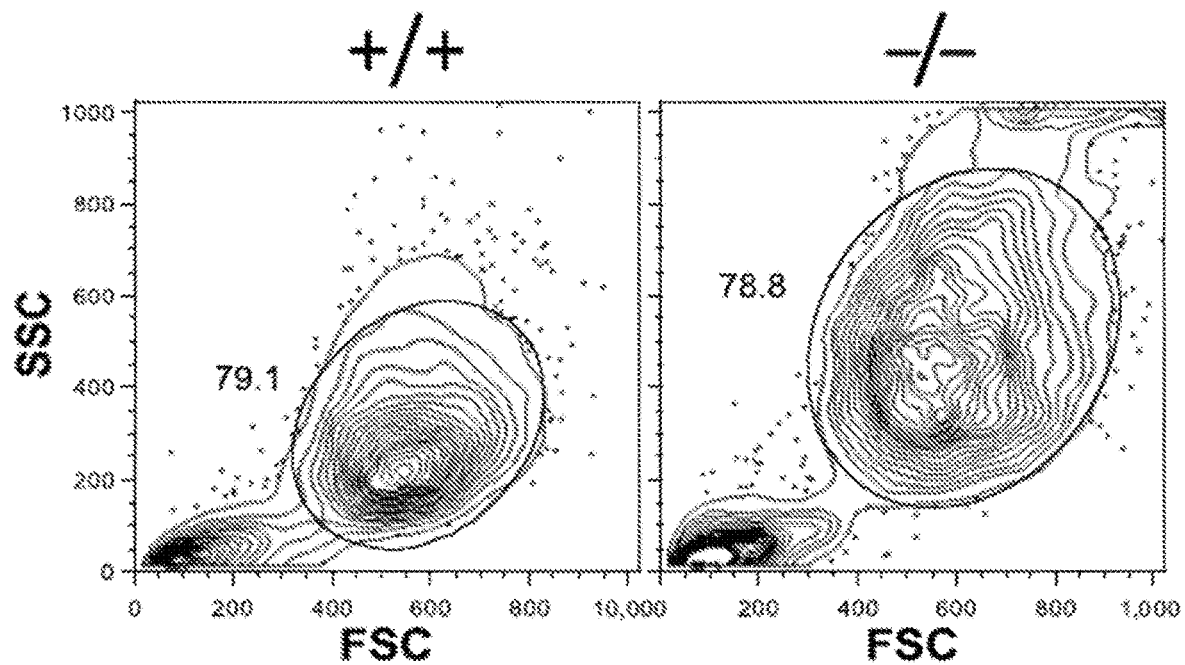
FIGS. 5A-5H provide data showing Dnase2a deficiency recapitulates cellular senescence.
Figure 5B:
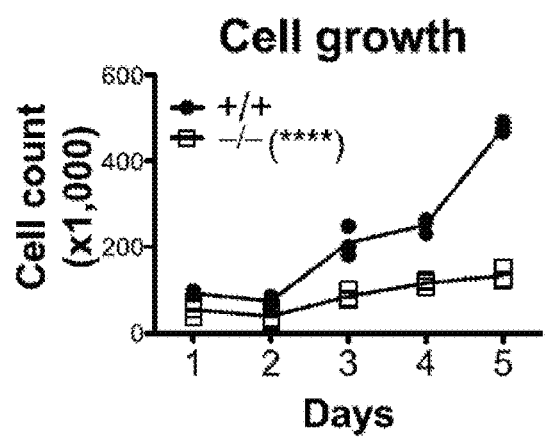
Figure 5C:
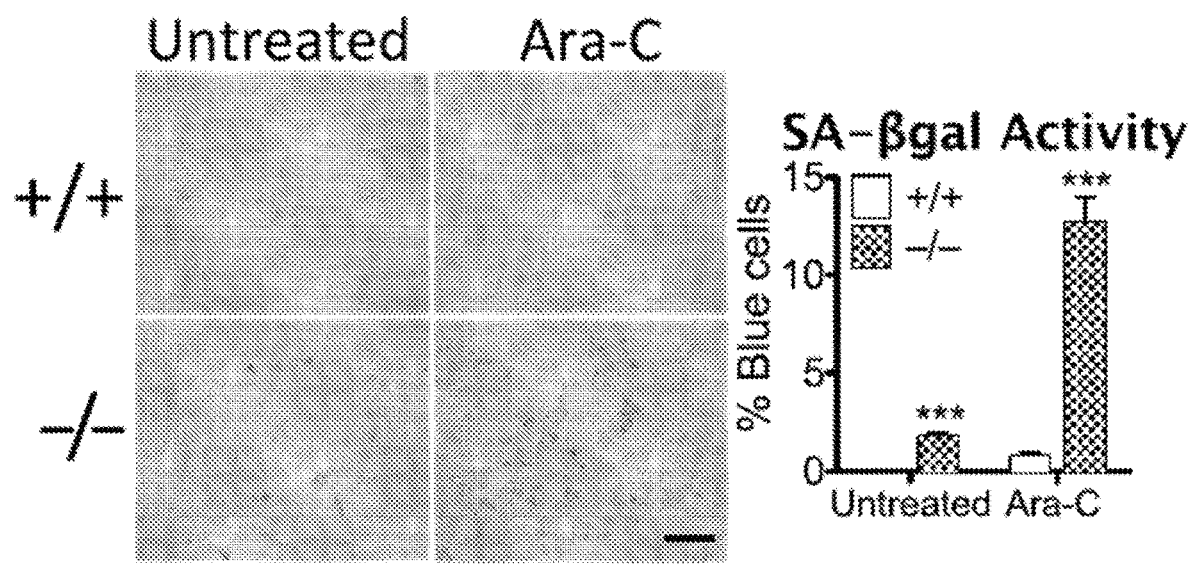
Figure 5D:
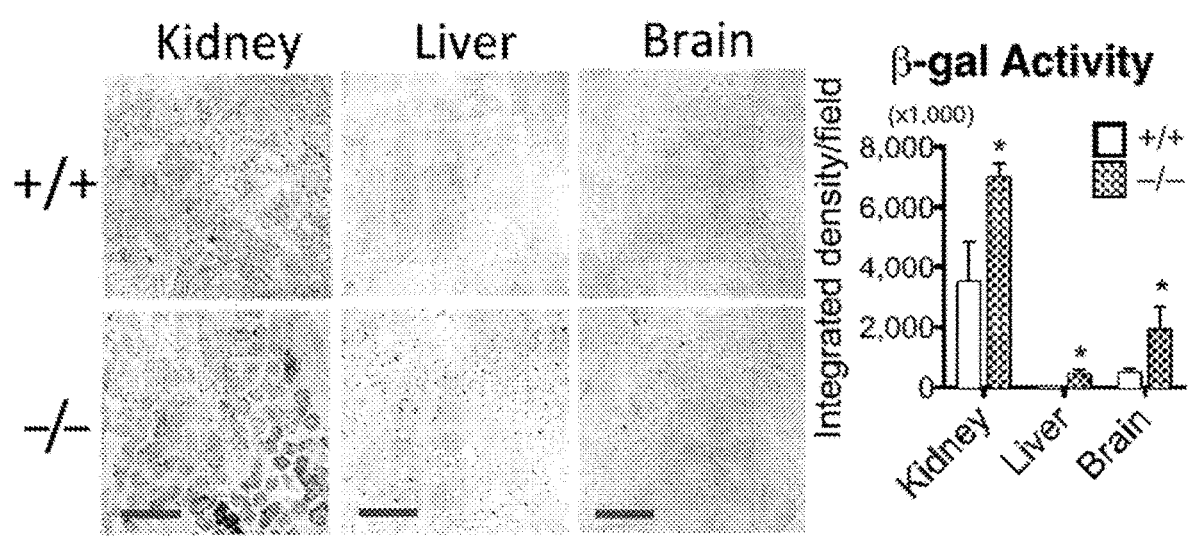
Figure 5E:
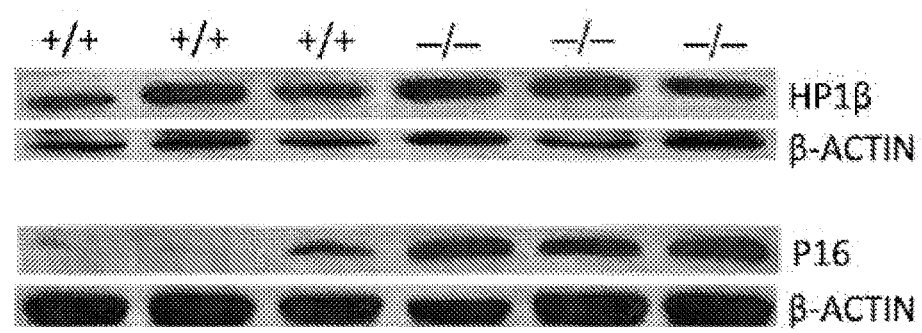
Figure 5F:
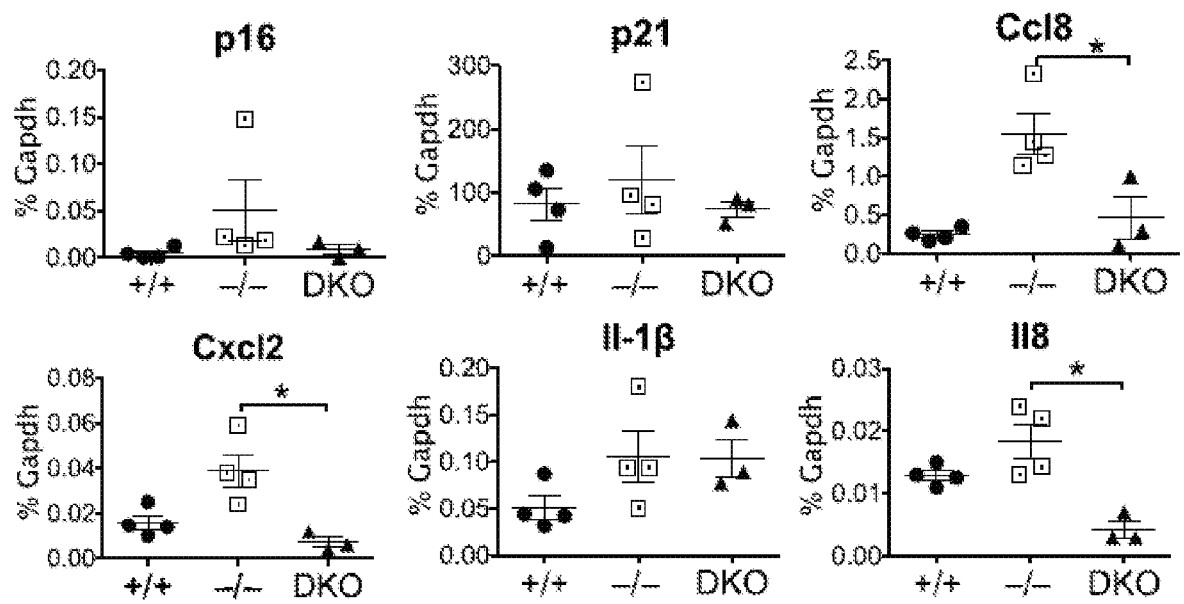
Figure 5G:
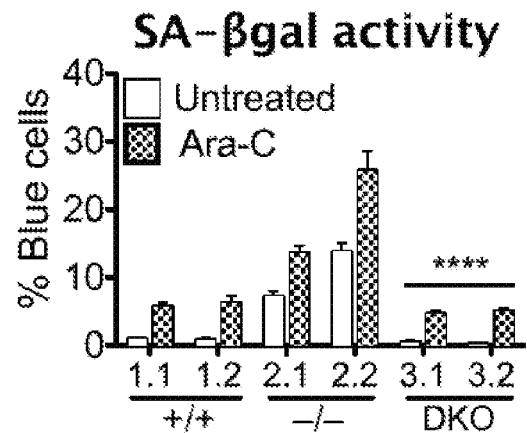
Figure 5H:
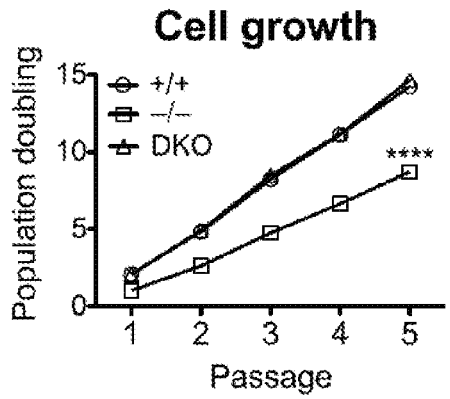
Figure 10A:
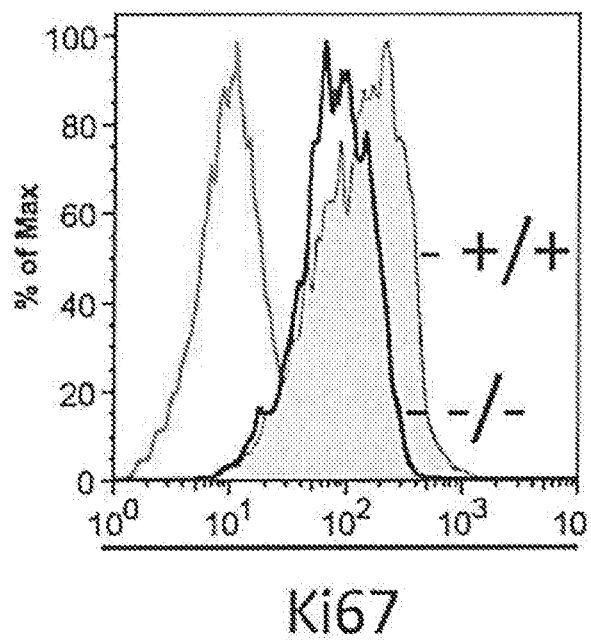
FIG. 10A shows cell proliferation of Dnase2a+/+ and Dnase2a–/– MLFs assessed by Ki67 staining using flow cytometry; Dnase2a+/+, shaded histogram, Dnase2a–/–, black open histogram; isotype control, light grey open histogram.
Figure 10B:
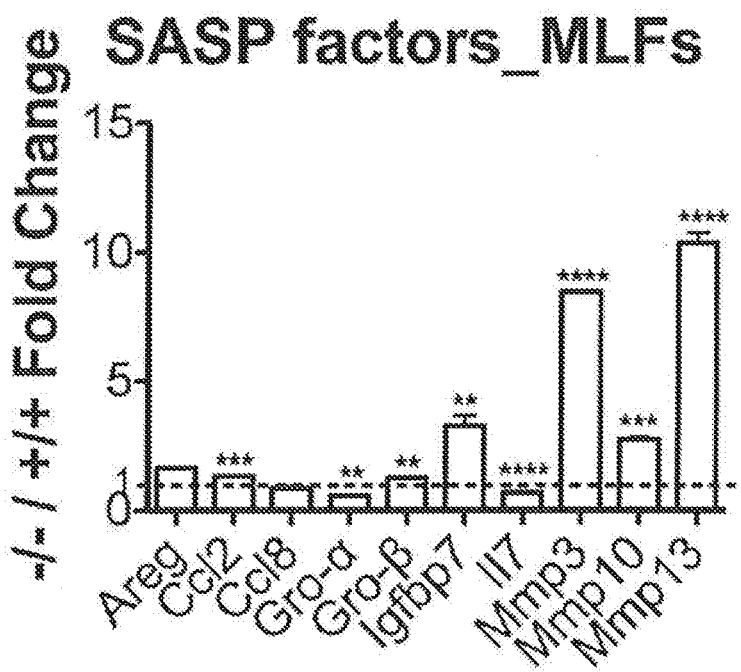
FIG. 10B shows fold change of transcript expressions of SASP factors in Dnase2a–/– vs. Dnase2a+/+ MLFs by RT-qPCR. Representative of 2 independent experiments shown.
Figure 10C:
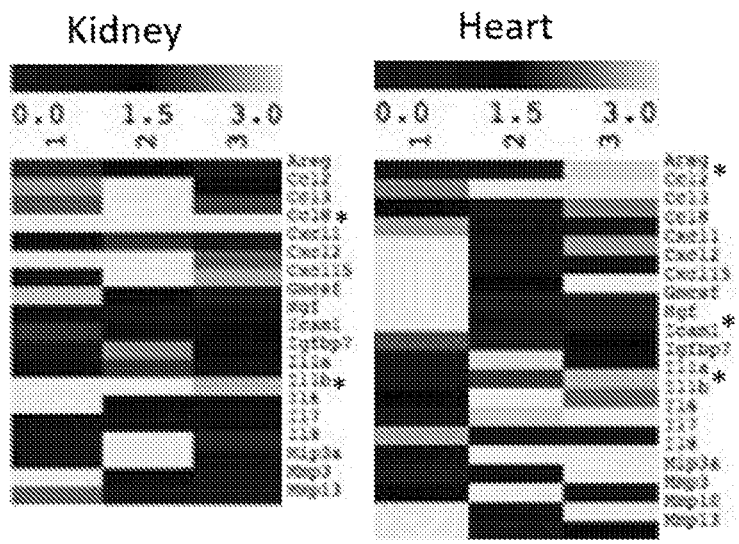
FIG. 10C is a heat map showing fold change of gene expression of SASP factors in Dnase2a–/– to Dnase2a+/+ kidney and heart tissues from 3 pairs of age and sex-matched littermates. Asterisks indicate significant genes.
Figure 10D:
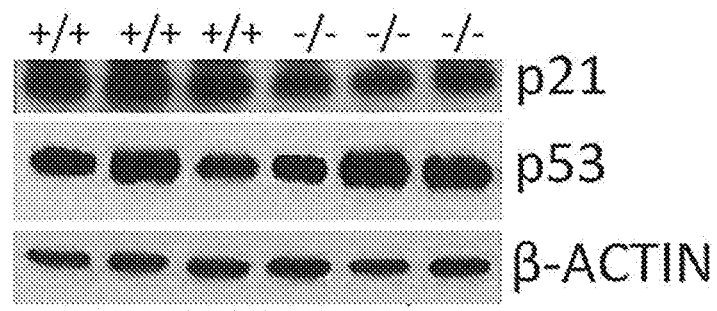
FIG. 10D is an immunoblot of p21 and p53 in kidney tissues from 3 pairs of age and sex-matched Dnase2a+/+ and Dnase2a–/– littermates.
Figure 10E:
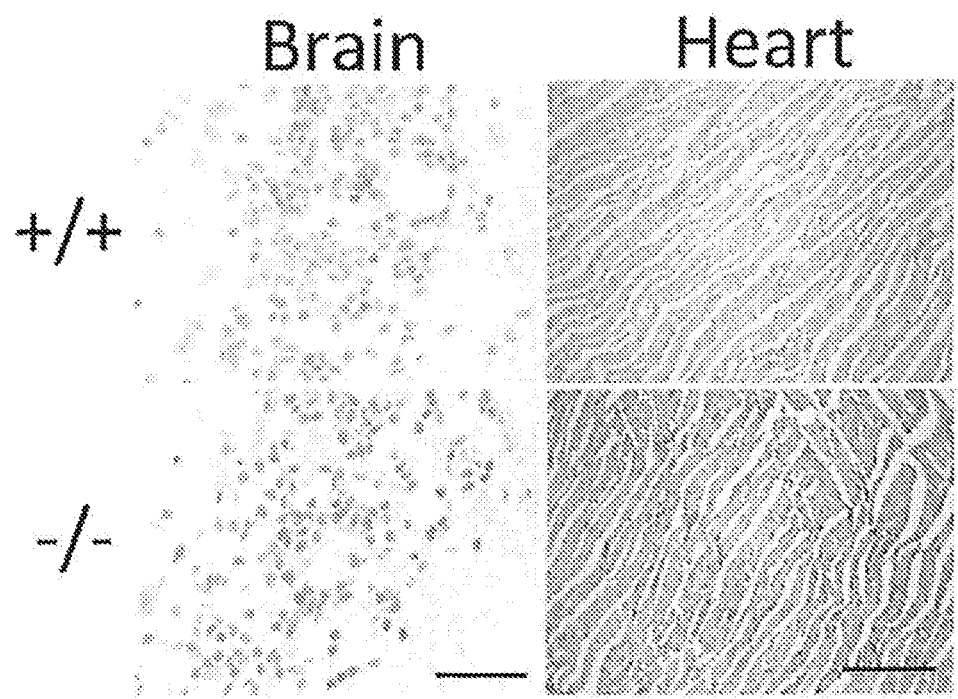
FIG. 10E shows immunohistochemical staining of p16 in brain and heart tissues from Dnase2a+/+ and Dnase2a–/– mice by DAB chromogen. Positive signals appear in dark grey, representative of 2 independent experiments; scale bar, 200 μm. Significance by t-test if not indicated.

The results discussed above were consistent with a model for DNA-induced inflammation and senescence in old cells and premature aging disease cells. It was next investigated whether DNA levels or STING-mediated sensing of intrinsic DNA affect senescence. A genetic mouse model in which the transport of excess nuclear DNA to the lysosomes for degradation by DNASE2A was used. To test whether DNA accumulation resulting from Dnase2a deficiency can promote a senescent phenotype, cellular features of senescence were examined including cell morphology, growth rates and response to stimuli. Compared with Dnase2a$^{+/+}$ cells, Dnase2a$^{-/-}$ mouse lung fibroblasts (MLFs) showed increased size and granularity by flow cytometry (FIG. 5A), and slower growth by cell count (FIG. 5B) or the proliferation marker Ki67 (FIG. 10A). SASP factors were upregulated in Dnase2a$^{-/-}$ MLFs (FIG. 10B) and tissues, including kidney and heart (FIG. 10C), compared to Dnase2a$^{+/+}$ mice as assessed by RT-qPCR. Dnase2a$^{-/-}$ cells also showed a higher percentage of cells with SA-β-gal activity in baseline or in response to Ara-C treatment, compared to Dnase2a$^{+/+}$ cells (FIG. 5C)—resembling the phenotype seen in response to DNA damage in old human cells (FIG. 6F). In various tissues, such as kidney, liver, and brain, SA-β-gal activity was stronger in Dnase2a$^{-/-}$ than Dnase2a$^{+/+}$ mice (FIG. 5D). Increased SA-β-gal activity also correlated with higher protein expression of the aging markers heterochromatin protein 10 (HP10) and p16 in the kidney of Dnase2a$^{-/-}$ mice (FIG. 5E), though concomitant increase in p53 failed to elevate p21 expression (FIG. 10D), suggesting additional regulation of this downstream effector. Higher p16 levels were similarly observed in less actively renewed tissues of brain and heart in Dnase2a$^{-/-}$ mice by immunohistochemical staining (FIG. 10E). The requirement for DNA sensing using Dnase2a$^{-/-}$; Sting$^{-/-}$ double KO (DKO) mice was examined and reduced gene expression of p16 and SASP factors such as Ccl8, Cxcl12, and Il8 were found in kidney tissues (FIG. 5F). DKO MLFs also showed lower SA-β-gal activity especially upon Ara-C treatment, compared with Dnase2a$^{-/-}$ cells (FIG. 5G), and importantly, regained proliferation like Dnase2a$^{+/+}$ cells (FIG. 5H). The rescued phenotype in DKO thus supports the central role of STING in promoting senescence upon excess cytosolic DNA accumulation.

Discussion

The data demonstrated above support the concept that sensing and degradation of self-DNA impact inflammation in cells undergoing replicative senescence or cells derived from aging diseases. First, in late passage cells, DNA exported from the nucleus through a leptomycin B-sensitive pathway was observed and it was shown that inflammatory cytokines were induced through the STING pathway. Second, it was found that inflammation could be reduced by overexpression of DNASE2A. Finally, using a mouse model, it was found that excess DNA burden led to STING-dependent inflammation and senescence phenotype with reduced proliferation in mouse cells ex vivo and mouse tissues in vivo. The data support a model in which extra-nuclear DNA triggers inflammation and senescence in vivo and in several cellular models of aging.

Modulating any step in the process of: DNA damage, transport, sensing and degradation may be therapeutically useful. Beyond conventional anti-inflammatory drugs (such as aspirin and NSAIDs), reducing DNA in the cytosolic environment could reduce inflammation and act as a novel therapeutic strategy for treating degenerative and aging-associated diseases, especially laminopathies with nuclear DNA found in the cytosol, and interferonopathies caused by loss of degradation components (Rodero et al., 2017).

Experimental Procedures

Cell Lines and Culture

IMR90, MRC5, and WI38 cells were cultured in DMEM plus 15% FBS, 1% penicillin/streptomycin, L-glutamate and sodium bicarbonate under 3% $O_2$ and 6% $CO_2$ at 37° C. to limit oxidative stress from atmospheric oxygen. Cells were split at 80%-90% confluence and PD calculated as log 2 (no. at split/no. plated). Young cells were <PD30 and old cells were from splits >10 days in culture (often last 3 splits before permanent growth arrest), for example PD67-70 in MRC5 cells. Human diploid fibroblast cultures derived from donor, AT and PS patient skins were obtained from Coriell Institute (Camden, N.J., USA), and maintained in DMEM, 15% FBS, 1% penicillin/streptomycin and L-glutamate under 5% $CO_2$ at 37° C. Healthy donor cells were H1: AG04392, PD17-30; H2: AG04433, PD12-28; H4: AG04525, PD13-25; H5: AG06555, PD19-35; AT cells are AT1: AG02496, PD unknown; AT2: AG03058, PD12-19; AT3: AG04405, PD9-18; and PS cells are PS1: AG10578, PD6-13; PS2: AG11513, PD9-16; PS3: AG03513, PD15-21; PS4: AG00989, PD27-34; PS5: AG019732, PD28-35. Splits of actively dividing passages were used, when H cells took 4-7 days, AT and PS cells 8-14 days.

Immunofluorescence Cell Staining and Quantitation

Cells were cultured in Lab-Tek II 8-well chamber slides, fixed with 4% PFA (10 min), permeabilized with 0.5% Triton X-100 (5 min), then blocked and stained with antibodies against: dsDNA (Santa Cruz, 1:500), 7H2AX, NUP98, pTBK1 (both Cell Signaling, 1:200), LC3 (Novus Biologicals, 1:200) or biotin-LAMP1 (BioLegend, 1:200), followed by fluorescent secondary antibodies (45 min). Methanol fixation was used for anti-pIRF3 (Cell Signaling, 1:200) staining.

Nuclear and cytosolic DNA signals from 5 of 10× or 20× images (~50-200 cells per image) were quantified using Fiji. Region of interest (ROI) was defined in each image and threshold set to measure fluorescence above background. Nuclear ROI was defined by DAPI staining and its intensity subtracted from total fluorescence to determine cytoplasmic signal. Quantitative fluorescence was presented as integrated density per cell with cell number determined by particle count of DAPI.

DNASE2A Overexpression

The human DNASE2A open reading frame (ORF) or control eGFP were cloned into a constitutive pLX304 vector with blasticidin resistance. Plasmid DNA was purified and transfected into 293 cells for packaging of lentiviruses, and viruses produced were used to infect human fibroblasts. Blasticidin selection was at 10 µg/ml, 24-48 hr.

Mice

Inducible Dnase2a KO mouse was received from Dr. Shigekazu Nagata (Kyoto University, Japan). WT and KO littermates were injected i.p. with 1.5 µg/weight (g) of poly I:C three times at 12-16 weeks of age to induce deletion of Dnase2a. Mice were housed in a specific pathogen-free facility at Massachusetts General Hospital. The MGH Subcommittee on Research and Animal Care approved all protocols and procedures for animal studies in accordance with the institutional animal ethics guidelines. Mouse tissues were fixed with 4% paraformaldehyde (PFA) overnight, dehydrated by 30% sucrose and frozen in OCT medium for cryo-sectioning.

Reagents

Ara-C, bafilomycin A1 and rapamycin were from Sigma-Aldrich (St. Louis, Mo.); SA β-gal Staining Kit was from Cell Signaling (Danvers, Mass.); TUNEL Apo-Green detection reaction mixture was from Biomake (Houston, Tex.).

Microscopy

IF (10×, 20×) or bright-field images (5×, 10×) were captured using Zeiss Axio Imager M2 upright microscope, Axiocam 506 and ZEN Blue software or by Axio Scan.Z1 with ZEN scan software.

NanoString Profiling and Data Normalization

Lysates in RLT buffer were hybridized for 12-24 hours with custom nCounter Gene Expression CodeSets. Hybridized RNA transcripts in a multiplex reaction were counted by the Nanostring nCounter system (Nanostring; SeaZle, WA). Results for multiple probes detecting the same gene were averaged and rounded to the nearest integer. Four reference genes (PHLDA1, SPRY2, SEMA3A and C9orf30) were selected based on uniform expression and used as "housekeeping" genes. Significant genes differentially expressed were determined by NanoStringDiff R package (version 1.4.0), using a Benjamin and Hochberg adjusted p value (FDR) threshold of 0.01.

RNA Sequencing and Analysis

RNA was isolated with RNeasy® Plus Mini Kit (Qiagen, MD). 1 ng RNA was used as template to generate full-length cDNA and sequencing libraries using the Smart-Seq2 protocol as previously described. Libraries were sequenced on a NextSeq 500 (Illumina) to an average depth of 12.4 million paired-end reads of length 38 bases each. Reads were mapped to the Gencode_v19 human transcriptome using Bowtie 2 and expression of all genes quantified using RSEM to yield an expression matrix (genes×samples) of inferred gene counts. Differential expression was calculated with EBSeq version 1.10.0, using the EBTest function with ten iterations following normalization using the MedianNorm function. Three rows were removed from the gene count table prior to analysis; ENSG00000225840, a Y chromosome rRNA pseudogene with high levels of aberrant mapping, and two mitochondrial rRNA genes (MT-RNR1 and MT-RNR2).

Gene ontology functional enrichment was assessed using Overrepresentation Enrichment Analysis on the WebGestalt online tool, comparing significantly differentially expressed genes (posterior probability of differential expression>0.95) against reference gene set containing all genes with non-zero transcript levels. Gene set enrichment analysis was run on the GenePattern platform. 1000 gene-set permutations were used, working from the MSigDB Hallmark gene set collection.

Knockdown Experiments Cells were transfected with 150 nM of siGENOME pool siRNA (Dharmacon, CO) targeting cGAS, STING, TBK1, DNASE2A or non-targeting control, using Lipofectamine™ RNAiMAX (Life Technologies). Knockdown efficiency was confirmed by RT-qPCR.

Immunoblotting

Cells were lysed in RIPA buffer (Boston Bioproducts, Worcester, Mass.) supplemented with Complete mini protease inhibitor cocktails (Roche, Indianapolis, Ind.) and protein concentration determined by Bio-Rad protein assay (Hercules, Calif.). 10-30 µg of protein was separated by SDS-PAGE in 10 or 12% mini-PROTEAN® precast gel (Bio-Rad) and transferred to PVDF membrane. Membrane was then blocked with 5% non-fat dry milk and immunoblotted with the following antibodies:

STING Cell Signaling #13647, 1:1000
TBK1 Cell Signaling #3504, 1:1000
pTBK1 Cell Signaling #5483, 1:1000
IRF3 Cell Signaling #4302, 1:1000
HP-1β Cell Signaling #2613, 1:1000
JAK1 Cell Signaling #3332, 1:1000
STAT1 Cell Signaling #9172, 1:1000
pSTAT1 Cell Signaling #9167, 1:1000
β-ACTIN Abcam ab6276, 1:10,000
Mouse p16 Abcam ab211542, 1:1000
Mouse p21 Santa Cruz sc-6246, 1:1000
Mouse p53 Santa Cruz sc-98, 1:1000

Cell Proliferation

Duplicate wells of 100,000 cells were plated in 6-well plates and counted daily for 5 days by trypan blue to exclude dead cells. Cells were trypsinized to split and re-plate upon 80-90% confluence (on day 3 or 4) to allow sufficient growth space. Both split wells were included in final count. Alternatively, cells were stained with PE conjugated Ki-67 antibody (Biolegend 652404) and analyzed by flow cytometry.

To assess cell growth over longer duration, triplicate wells were plated and counted at confluence. Equal numbers of cells were then serially plated at each split. Cell growth was then calculated as cumulative PD at each passage.

DNA Digestion Assay

Two million MRC5 young and old cells were pelleted and lysed in 80 µl of 20 mM Tris-HCl with protease inhibitors, pH=7.5. Different volumes of lysates were incubated with 50 µg of calf thymus DNA in a total volume of 45 µl of 25 mM of sodium acetate (pH=4.7) for 15 min at room temperature. Digested DNA products were loaded onto 0.7% agarose gel and visualized by ethidium bromide. Dilutions of porcine DNASE2 (Sigma D4138) were used as positive control.

Real-Time RT-qPCR 0.25-1 µg of total RNA was reverse-transcribed with High Capacity cDNA Reverse Transcription kit (Applied Biosystems). Quantitative PCR was then performed using LightCyler® 480 SYBR Master I reagents (Roche) on LightCyler® 96 instrument. Transcript levels were normalized to B2M or GAPDH. Primer pairs used are listed below.

| HUMAN PRIMERS | 5'-3' SEQUENCE |
|---|---|
| ATG5-F | AAAGATGTGCTTCGAGATGTGT (SEQ ID NO: 3) |
| ATG5-R | CACTTTGTCAGTTACCAACGTCA (SEQ ID NO: 4) |
| BECN1-F | CCATGCAGGTGAGCTTCGT (SEQ ID NO: 5) |
| BECN1-R | GAATCTGCGAGAGACACCATC (SEQ ID NO: 6) |
| P62-F | TGCCCAGACTACGACTTGTG (SEQ ID NO: 7) |
| P62-R | AGTGTCCGTGTTTCACCTTCC (SEQ ID NO: 8) |
| PTEN-F | TGGATTCGACTTAGACTTGACCT (SEQ ID NO: 9) |
| PTEN-R | TGGCGGTGTCATAATGTCTTTC (SEQ ID NO: 10) |
| cGAS-F | TAACCCTGGCTTTGGAATCAAAA (SEQ ID NO: 11) |
| cGAS-R | TGGGTACAAGGTAAAATGGCTTT (SEQ ID NO: 12) |
| STING-F | GGTCACCGCTCCAAATATGTAG (SEQ ID NO: 13) |
| STING-R | CAGTAGTCCAAGTTCGTGCGA (SEQ ID NO: 14) |
| TBK1-F | AGCGGCAGAGTTAGGTGAAA (SEQ ID NO: 15) |
| TBK1-R | TGAGTGCCTTCTTGATGTGC (SEQ ID NO: 16) |
| MX1-F | GTTTCCGAAGTGGACATCGCA (SEQ ID NO: 17) |
| MX1-R | CTGCACAGGTTGTTCTCAGC (SEQ ID NO: 18) |
| IFIT1-F | TTGATGACGATGAAATGCCTGA (SEQ ID NO: 19) |
| IFIT1-R | CAGGTCACCAGACTCCTCAC (SEQ ID NO: 20) |
| IL6-F | AAATTCGGTACATCCTCGACGG (SEQ ID NO: 21) |
| IL6-R | GGAAGGTTCAGGTTGTTTTCTGC (SEQ ID NO: 22) |
| CXCL10-F | CCAAGTGCTGCCGTCATTTTC (SEQ ID NO: 23) |
| CXCL10-R | GGCTCGCAGGGATGATTTCAA (SEQ ID NO: 24) |
| DNASE2A-F | TCGCCTTCCTGCTCTACAAT (SEQ ID NO: 25) |
| DNASE2A-R | CCCATCTTCGAGAACTGAGC (SEQ ID NO: 26) |
| AREG-F | GTGGTGCTGTCGCTCTTGATA (SEQ ID NO: 27) |
| AREG-R | CCCCAGAAAATGGTTCACGCT (SEQ ID NO: 28) |
| GMCSF-F | TTCTGCTTGTCATCCCCTTT (SEQ ID NO: 29) |
| GMCSF-R | CTTCTGCCATGCCTGTATCA (SEQ ID NO: 30) |
| IGFBP7-F | CGAGCAAGGTCCTTCCATAGT (SEQ ID NO: 31) |
| IGFBP7-R | GGTGTCGGGATTCCGATGAC (SEQ ID NO: 32) |
| MMP3-F | AGTCTTCCAATCCTACTGTTGCT (SEQ ID NO: 33) |
| MMP3-R | TCCCCGTCACCTCCAATCC (SEQ ID NO: 34) |
| MMP10-F | TGCTCTGCCTATCCTCTGAGT (SEQ ID NO: 35) |
| MMP10-R | TCACATCCTTTTCGAGGTTGTAG (SEQ ID NO: 36) |
| MMP13-F | ACTGAGAGGCTCCGAGAAATG (SEQ ID NO: 37) |
| MMP13-R | GAACCCCGCATCTTGGCTT (SEQ ID NO: 38) |
| P16-F | GGGTTTTCGTGGTTCACATCC (SEQ ID NO: 39) |
| P16-R | CTAGACGCTGGCTCCTCAGTA (SEQ ID NO: 40) |
| P21-F | TGTCCGTCAGAACCCATGC (SEQ ID NO: 41) |
| P21-R | AAAGTCGAAGTTCCATCGCTC (SEQ ID NO: 42) |
| B2M-F | CTCCGTGGCCTTAGCTGTG (SEQ ID NO: 43) |
| B2M-R | TTTGGAGTACGCTGGATAGCCT (SEQ ID NO: 44) |
| GAPDH-F | ACAACTTTGGTATCGTGGAAGG (SEQ ID NO: 45) |
| GAPDH-R | GCCATCACGCCACAGTTTC (SEQ ID NO: 46) |
| MOUSE | 5'-3' SEQUENCE |
| p16GF | GAACTCTTTCGGTCGTACCC (SEQ ID NO: 47) |
| p16GR | CGAATCTGCACCGTAGTTGA (SEQ ID NO: 48) |
| p21GF | CCTGGTGATGTCCGACCTG (SEQ ID NO: 49) |
| p21GR | CCATGAGCGCATCGCAATC (SEQ ID NO: 50) |
| Ccl18GF | TCTACGCAGTGCTTCTTTGCC (SEQ ID NO: 51) |
| Ccl18GR | AAGGGGGATCTTCAGCTTTAGTA (SEQ ID NO: 52) |
| Cxcl2GF | GCGCCCAGACAGAAGTCATAG (SEQ ID NO: 53) |
| Cxcl2GR | AGCCTTGCCTTTGTTCAGTATC (SEQ ID NO: 54) |
| ll1bGF | CCAGCTTCAAATCTCACAGCAG (SEQ ID NO: 55) |
| ll1bGR | CTTCTTTGGGTATTGCTTGGGATC (SEQ ID NO: 56) |
| ll8GF | TCGAGACCATTTACTGCAACAG (SEQ ID NO: 57) |
| ll8GR | CATTGCCGGTGGAAATTCCTT (SEQ ID NO: 58) |
| Dnase2GF | GCTCAGCTGGGGACTCTAC (SEQ ID NO: 59) |
| Dnase2G | GGTCTGGCCGAAGGTTTGA (SEQ ID NO: 60) |
| GapdhGF | AGGTCGGTGTGAACGGATTTG (SEQ ID NO: 61) |
| GapdhGR | TGTAGACCATGTAGTTGAGGTCA (SEQ ID NO: 62) |

Statistical Analyses Statistical analyses were performed using GraphPad PRISM 4 or as described. Values were expressed as mean±sem. Samples were analyzed using Student's t-test or as indicated, with $p<0.05$ deemed statistically significant and denoted by *; $p<0.05$, *; $p<0.01$, ; $p<0.005$, *; $p<0.0001$, ****.

REFERENCES

1. Almine, J. F., O'Hare, C. A., Dunphy, G., Haga, I. R., Naik, R. J., Atrih, A., . . . Unterholzner, L. (2017). IFI16 and cGAS cooperate in the activation of STING during DNA sensing in human keratinocytes. *Nature Communications*, 8, 14392. https://doi.org/10.1038/ncomms14392.
2. Bartkova, J., Rezaei, N., Lionros, M., Karakaidos, P., Kletsas, D., Issaeva, N., . . . Gorgoulis, V. G. (2006). Oncogene-induced senescence is part of the tumorigenesis barrier imposed by DNA damage checkpoints. *Nature*, 444(7119), 633-637. https://doi.org/10.1038/nature05268.
3. Baruch, K., Deczkowska, A., David, E., Castellano, J. M., Miller, O., Kertser, A., . . . Schwartz, M. (2014). Aging-induced type I interferon response at the choroid plexus negatively affects brain function. *Science,* 346(6205), 89-93. https://doi.org/10.1126/science.1252945.

4. Coppé, J. P., Patil, C. K., Rodier, F., Krtolica, A., Beausejour, C. M., Parrinello, S., . . . Campisi, J. (2010). A human-like senescence-associated secretory phenotype is conserved in mouse cells dependent on physiological oxygen. *PLoS One,* 5(2), e9188. https://doi.org/10.1371/journal.pone.0009188.

5. De Vos, W. H., Houben, F., Kamps, M., Malhas, A., Verheyen, F., Cox, J., Broers, J. L. (2011). Repetitive disruptions of the nuclear envelope invoke temporary loss of cellular compartmentalization in laminopathies. *Human Molecular Genetics,* 20(21), 4175-4186. https://doi.org/10.1093/hmg/ddr344.

6. Di Leonardo, A., Linke, S. P., Clarkin, K., & Wahl, G. M. (1994). DNA damage triggers a prolonged p53-dependent G1 arrest and long-term induction of Cip1 in normal human fibroblasts. *Genes & Development,* 8(21), 2540-2551. https://doi.org/10.1101/gad.8.21.2540

7. Don, Z., Ghosh, K., Vizioli, M. G., Zhu, J., Sen, P., Wangensteen, K. J., Berger, S. L. (2017). Cytoplasmic chromatin triggers inflammation in senescence and cancer. *Nature,* 550(7676), 402-406. https://doi.org/10.1038/nature24050.

8. Duan, X., Ponomareva, L., Veeranki, S., Panchanathan, R., Dickerson, E., & Choubey, D. (2011). Differential roles for the interferon-inducible IFI16 and AIM2 innate immune sensors for cytosolic DNA in cellular senescence of human fibroblasts. *Molecular Cancer Research,* 9(5), 589-602. https://doi.org/10.1158/1541-7786.MCR-10-0565.

9. Fagiolo, U., Cossarizza, A., Scala, E., Fanales-Belasio, E., Ortolani, C., Cozzi, E., . . . Paganelli, R. (1993). Increased cytokine production in mononuclear cells of healthy elderly people. *European Journal of Immunology,* 23(9), 2375-2378. https://doi.org/10.1002/eji.1830230950.

10. Glück, S., Guey, B., Gulen, M. F., Wolter, K., Kang, T. W., Schmacke, N. A., Ablasser, A. (2017). Innate immune sensing of cytosolic chromatin fragments through cGAS promotes senescence. *Nature Cell Biology,* 19(9), 1061-1070. https://doi.org/10.1038/ncb3586.

11. Goldman, R. D., Shumaker, D. K., Erdos, M. R., Eriksson, M., Goldman, A. E., Gordon, L. B., . . . Collins, F. S. (2004). Accumulation of mutant lamin A causes progressive changes in nuclear architecture in Hutchinson-Gilford progeria syndrome. *Proceedings of the National Academy of Sciences,* 101(24), 8963-8968. https://doi.org/10.1073/pnas.0402943101.

12. Gorbea, C., Rechsteiner, M., Vallejo, J. G., & Bowles, N. E. (2013). Depletion of the 26S proteasome adaptor Ecm29 increases Toll-like receptor 3 signaling. *Science Signalling,* 6(295), ra86. https://doi.org/10.1126/scisignal.2004301.

13. Hartlova, A., Erttmann, S. F., Raffi, F. A., Schmalz, A. M., Resch, U., Anugula, S., . . . Gekara, N. O. (2015). DNA damage primes the type I interferon system via the cytosolic DNA sensor STING to promote anti-microbial innate immunity. *Immunity,* 42(2), 332-343. https://doi.org/10.1016/j.immuni.2015.01.012.

14. Hatch, E. M., Fischer, A. H., Deerinck, T. J., & Hetzer, M. W. (2013). Catastrophic nuclear envelope collapse in cancer cell micronuclei. *Cell,* 154(1), 47-60. https://doi.org/10.1016/j.cell.2013.06.007.

15. Herzner, A. M., Hagmann, C. A., Goldeck, M., Wolter, S., Kubler, K., Wittmann, S., . . . Schlee, M. (2015). Sequence-specific activation of the DNA sensor cGAS by Y-form DNA structures as found in primary HIV-1 cDNA. *Nature Immunology,* 16(10), 1025-1033. https://doi.org/10.1038/ni.3267.

16. Ivanov, A., Pawlikowski, J., Manoharan, I., van Tuyn, J., Nelson, D. M., Rai, T. S., . . . Adams, P. D. (2013). Lysosome-mediated processing of chromatin in senescence. *Journal of Cell Biology,* 202(1), 129-143. https://doi.org/10.1083/jcb.201212110.

17. Katlinskaya, Y. V., Katlinski, K. V., Yu, Q., Ortiz, A., Beiting, D. P., Brice, A., . . . Fuchs, S. Y. (2016). Suppression of Type I Interferon Signaling Overcomes Oncogene-Induced Senescence and Mediates Melanoma Development and Progression. *Cell Reports,* 15(1), 171-180. https://doi.org/10.1016/j.celrep.2016.03.006.

18. Kerur, N., Veettil, M. V., Sharma-Walia, N., Bottero, V., Sadagopan, S., Otageri, P., & Chandran, B. (2011). IFI16 acts as a nuclear pathogen sensor to induce the inflammasome in response to Kaposi Sarcoma-associated herpesvirus infection. *Cell Host & Microbe,* 9(5), 363-375. https://doi.org/10.1016/j.chom.2011.04.008.

19. Lan, Y. Y., Londono, D., Bouley, R., Rooney, M. S., & Hacohen, N. (2014). Dnase2a deficiency uncovers lysosomal clearance of damaged nuclear DNA via autophagy. *Cell Reports,* 9(1), 180-192. https://doi.org/10.1016/j.celrep.2014.08.074.

20. Le, O. N., Rodier, F., Fontaine, F., Coppé, J. P., Campisi, J., DeGregori, J., Beausejour, C. M. (2010). Ionizing radiation-induced long-term expression of senescence markers in mice is independent of p53 and immune status. *Aging Cell,* 9(3), 398-409. https://doi.org/10.1111/j.1474-9726.2010.00567.x.

21. Li, T., & Chen, Z. J. (2018). The cGAS-cGAMP-STING pathway connects DNA damage to inflammation, senescence, and cancer. *Journal of Experimental Medicine,* 215(5), 1287-1299. https://doi.org/10.1084/jem.20180139.

22. Liang, Q., Seo, G. J., Choi, Y. J., Kwak, M. J., Ge, J., Rodgers, M. A., Jung, J. U. (2014). Crosstalk between the cGAS DNA sensor and Beclin-1 autophagy protein shapes innate antimicrobial immune responses. *Cell Host & Microbe,* 15(2), 228-238. https://doi.org/10.1016/j.chom.2014.01.009.

23. Lu, T., Pan, Y., Kao, S. Y., Li, C., Kohane, I., Chan, J., & Yankner, B. A. (2004). Gene regulation and DNA damage in the ageing human brain. *Nature,* 429(6994), 883-891. https://doi.org/10.1038/nature02661.

24. Nougayrede, J. P., Homburg, S., Taieb, F., Boury, M., Brzuszkiewicz, E., Gottschalk, G., . . . Oswald, E. (2006). *Escherichia coli* induces DNA double-strand breaks in eukaryotic cells. *Science,* 313(5788), 848-851. https://doi.org/10.1126/science.1127059.

25. Parrinello, S., Samper, E., Krtolica, A., Goldstein, J., Melov, S., & Campisi, J. (2003). Oxygen sensitivity severely limits the replicative lifespan of murine fibroblasts. *Nature Cell Biology,* 5(8), 741-747. https://doi.org/10.1038/ncb1024.

26. Raab, M., Gentili, M., de Belly, H., Thiam, H. R., Vargas, P., Jimenez, A. J., Piel, M. (2016). ESCRT III repairs nuclear envelope ruptures during cell migration to limit DNA damage and cell death. *Science,* 352 (6283), 359-362. https://doi.org/10.1126/science.aad7611.

27. Rodero, M. P., Tesser, A., Bartok, E., Rice, G. I., Della Mina, E., Depp, M., Crow, Y. J. (2017). Type I interferon-mediated autoinflammation due to DNase II deficiency. *Nature Communications,* 8(1), 2176. https://doi.org/10.1038/s41467-017-01932-3.

28. Roubenoff, R., Parise, H., Payette, H. A., Abad, L. W., D'Agostino, R., Jacques, P. F., . . . Harris, T. B. (2003). Cytokines, insulin-like growth factor 1, sarcopenia, and mortality in very old community-dwelling men and women: The Framingham Heart Study. *American Journal of Medicine,* 115(6), 429-435. https://doi.org/10.1016/j.amjmed.2003.05.001
29. Rube, C. E., Fricke, A., Widmann, T. A., Furst, T., Madry, H., Pfreundschuh, M., & Rube, C. (2011). Accumulation of DNA damage in hematopoietic stem and progenitor cells during human aging. *PLoS One,* 6(3), e17487. https://doi.org/10.1371/journal.pone.0017487.
30. Rusinova, I., Forster, S., Yu, S., Kannan, A., Masse, M., Cumming, H., Hertzog, P. J. (2013). Interferome v2.0: An updated database of annotated interferon-regulated genes. *Nucleic Acids Research,* 41(D1), D1040-D1046. https://doi.org/10.1093/nar/gks1215.
31. Sedelnikova, O. A., Horikawa, I., Zimonjic, D. B., Popescu, N. C., Bonner, M., & Barrett, J. C. (2004). Senescing human cells and ageing mice accumulate DNA lesions with unrepairable double-strand breaks. *Nature Cell Biology,* 6(2), 168-170. https://doi.org/10.1038/ncb1095.
32. Singh, T., & Newman, A. B. (2011). Inflammatory markers in population studies of aging. *Ageing Research Reviews,* 10(3), 319-329. https://doi.org/10.1016/j.arr.2010.11.002.
33. Speese, S. D., Ashley, J., Jokhi, V., Nunnari, J., Barria, R., Li, Y., . . . Budnik, (2012). Nuclear envelope budding enables large ribonucleoprotein particle export during synaptic Wnt signaling. *Cell,* 149(4), 832-846. https://doi.org/10.1016/j.cell.2012.03.032.
34. Takahashi, A., Loo, T. M., Okada, R., Kamachi, F., Watanabe, Y., Wakita, M., . . . Hara, E. (2018). Downregulation of cytoplasmic DNases is implicated in cytoplasmic DNA accumulation and SASP in senescent cells. *Nature Communications,* 9(1), 1249. https://doi.org/10.1038/s41467-018-03555-8.
35. Vargas, J. D., Hatch, E. M., Anderson, D. J., & Hetzer, M. W. (2012). Transient nuclear envelope rupturing during interphase in human cancer cells. *Nucleus,* 3(1), 88-100. https://doi.org/10.4161/nucl.18954.
36. Wang, C., Jurk, D., Maddick, M., Nelson, G., Martin-Ruiz, C., & von Zglinicki, T. (2009). DNA damage response and cellular senescence in tissues of aging mice. *Aging Cell,* 8(3), 311-323. https://doi.org/10.1111/j.1474-9726.2009.00481.x.
37. Yang, H., Wang, H., Ren, J., Chen, Q., & Chen, Z. J. (2017). cGAS is essential for cellular senescence. *Proceedings of the National Academy of Sciences,* 114(23), E4612-E4620. https://doi.org/10.1073/pnas.1705499114.
38. Yu, Q., Katlinskaya, Y. V., Carbone, C. J., Zhao, B., Katlinski, K. V., Zheng, H., . . . Fuchs, S. Y. (2015). DNA-damage-induced type I interferon promotes senescence and inhibits stem cell function. *Cell Reports,* 11 (5), 785-797. https://doi.org/10.1016/j.celrep.2015.03.069.
39. Wang, H. et al. NanoStringDiff: a novel statistical method for differential expression analysis based on NanoString nCounter data. *Nucleic Acids Res.* gkw677 (2016).
40. Picelli, S. et al. Full-length RNA-seq from single cells using Smart-seq2. *Nat. Protoc.* 9, 171-181 (2014).
41. Langmead, B. & Salzberg, S. L. Fast gapped-read alignment with Bowtie 2. *Nat. Methods* 9, 357-359 (2012).
42. Li, B. & Dewey, C. N. RSEM: accurate transcript quantification from RNA-Seq data with or without a reference genome. *BMC Bioinformatics* 12, 1-16 (2011).
43. Leng, N. et al. EBSeq: an empirical Bayes hierarchical model for inference in RNA-seq experiments. *Bioinformatics* 29, 1035-1043 (2013).
44. Wang, J., Duncan, D., Shi, Z. & Zhang, B. WEB-based GEne SeT AnaLysis Toolkit (WebGestalt): update 2013. *Nucleic Acids Res.* 41, W77-W83 (2013).
45. Subramanian, A. et al. Gene set enrichment analysis: A knowledge-based approach for interpreting genome-wide expression profiles. *Proc. Natl. Acad. Sci.* 102, 15545-15550 (2005).
46. Michael Reich et al. GenePattern 2.0. *Nat. Genet.* 38, 500-501 (2006).
47. Liberzon, A. et al. The Molecular Signatures Database Hallmark Gene Set Collection. *Cell Syst.* 1, 417-425 (2015).

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for treating an aging-associated condition in a subject, comprising:
   administering a DNase enzyme to the subject,
   wherein the aging-associated condition is a laminopathy, an interferonopathy, ataxia telangiectasia (A-T), Hutchison-Gilford progeria, or aging-associated inflammation and cellular senescence that is induced or enhanced by treatment with a chemotherapeutic agent.

2. The method of claim 1, wherein the DNase enzyme is administered by systemic or local administration.

3. The method of claim 1, wherein the DNase enzyme is administered by gene therapy.

4. The method of claim 1, wherein the DNase enzyme is a lysosomal nuclease enzyme.

5. The method of claim 1, wherein the DNase enzyme is DNASE2A or a derivative of DNASE2A.

6. The method of claim 5, wherein the derivative of DNASE2A is functionally enhanced relative to DNASE2A.

7. The method of claim 1, wherein said chemotherapeutic agent is a DNA damaging agent, optionally cytarabine (ara-C).

8. The method of claim 1, wherein the subject is identified as having elevated levels of extranuclear DNA and/or SA-β-gal activity relative to a control.

9. The method of claim 1, wherein the subject is identified as having elevated levels of:

(i) one or more autophagy genes, optionally ATG5, BECLIN1, P62, or PTEN;
   (ii) one or more autophagosome marker, optionally LC3;
   (iii) one or more lysosomal protein, optionally LAMP1; and/or
   (iv) one or more inflammatory genes, optionally MX1, CXCL10, or IL-6 relative to a control.

10. A method for treating an aging-associated condition in a subject, comprising:
    identifying a subject as having elevated levels of extranuclear DNA relative to a control; and
    administering a DNase enzyme to the subject.

11. A method for treating an aging-associated condition in a subject, comprising:
    identifying a subject as having elevated levels of SA-β-gal activity relative to a control; and
    administering a DNase enzyme to the subject.

12. The method of claim 8, wherein the control is a sample from a subject who does not have an aging-associated condition.

13. The method of claim 8, wherein the control is a predetermined value.

14. The method of claim 1, wherein the subject is a human.

* * * * *